United States Patent
Gill et al.

(10) Patent No.: US 9,187,434 B2
(45) Date of Patent: Nov. 17, 2015

(54) SUBSTITUTED 1,5-BENZODIAZEPINONES COMPOUNDS

(71) Applicant: BRISTOL-MYERS SQUIBB COMPANY, Princeton, NJ (US)

(72) Inventors: Patrice Gill, Levittown, PA (US); Claude A. Quesnelle, Skillman, NJ (US); Mark G. Saulnier, Higganum, CT (US); Ashvinikumar V. Gavai, Princeton Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/429,964

(22) PCT Filed: Sep. 20, 2013

(86) PCT No.: PCT/US2013/060781
§ 371 (c)(1),
(2) Date: Mar. 20, 2015

(87) PCT Pub. No.: WO2014/047369
PCT Pub. Date: Mar. 27, 2014

(65) Prior Publication Data
US 2015/0274679 A1 Oct. 1, 2015

Related U.S. Application Data

(60) Provisional application No. 61/703,931, filed on Sep. 21, 2012.

(51) Int. Cl.
*C07D 401/04* (2006.01)
*C07D 243/24* (2006.01)
*C07D 243/14* (2006.01)
*A61K 31/5513* (2006.01)
*A61K 45/06* (2006.01)

(52) U.S. Cl.
CPC .......... *C07D 243/14* (2013.01); *A61K 31/5513* (2013.01); *A61K 45/06* (2013.01); *C07D 401/04* (2013.01)

(58) Field of Classification Search
CPC ............................ C07D 401/04; C07D 243/24
See application file for complete search history.

(56) References Cited

U.S. PATENT DOCUMENTS

| | | | |
|---|---|---|---|
| 4,981,847 A | 1/1991 | Sato et al. | |
| 5,322,842 A | 6/1994 | Sato et al. | |
| 5,324,726 A | 6/1994 | Bock et al. | |
| 5,852,010 A | 12/1998 | Graham et al. | |
| 5,998,407 A | 12/1999 | Graham et al. | |
| 6,331,408 B1 | 12/2001 | Zaczek et al. | |
| 6,495,540 B2 | 12/2002 | Thompson | |
| 6,503,901 B1 | 1/2003 | Thompson et al. | |
| 6,503,902 B2 | 1/2003 | Olson et al. | |
| 6,509,333 B2 | 1/2003 | Olson | |
| 6,525,044 B2 | 2/2003 | Olson et al. | |
| 6,544,978 B2 | 4/2003 | Wu et al. | |
| 6,632,812 B2 | 10/2003 | Han et al. | |
| 6,653,303 B1 | 11/2003 | Wu et al. | |
| 6,713,476 B2 | 3/2004 | Yang et al. | |
| 6,737,038 B1 | 5/2004 | Zaczek et al. | |
| 6,756,511 B2 | 6/2004 | Castro Pineiro et al. | |
| 6,759,404 B2 | 7/2004 | Olson et al. | |
| 6,794,381 B1 | 9/2004 | Olson et al. | |
| 6,878,363 B2 | 4/2005 | Zaczek et al. | |
| 6,900,199 B2 | 5/2005 | Han et al. | |
| 6,958,329 B2 | 10/2005 | Olson | |
| 6,960,576 B2 | 11/2005 | Olson et al. | |
| 6,962,913 B2 | 11/2005 | Olson et al. | |
| 6,984,626 B2 | 1/2006 | Nadin et al. | |
| 7,001,901 B2 | 2/2006 | Yang | |
| 7,053,081 B2 | 5/2006 | Olson et al. | |
| 7,053,084 B1 | 5/2006 | Olson | |
| 7,101,870 B2 | 9/2006 | Olson et al. | |
| 7,105,509 B2 | 9/2006 | Castro Pineiro et al. | |

(Continued)

FOREIGN PATENT DOCUMENTS

EP 0669334 8/1995
WO WO 97/36879 10/1997

(Continued)

OTHER PUBLICATIONS

U.S. Appl. No. 14/627,573, filed Feb. 20, 2015, Gavai et al.
Groth, C., et al., "Therapeutic approaches to modulating Notch signaling: Current challenges and future prospects," Seminars in Cell & Developmental Biology, (2012), doi:10.1016/j.semcdb2012.01.016; available online Mar. 7, 2012.
Seiffert, D., et al., "Presenilin-1 and -2 Are Molecular Targets for gamma-Secretase Inhibitors," The Journal of Biological Chemistry, vol. 275, No. 44, pp. 34086-34091 (2000).
Beher, D., et al., "Pharmacological Knock-down of the Presenilin 1 Heterodimer by a Novel gamma-Secretase Inhibitor," The Journal of Biological Chemistry, vol. 276, No. 48, pp. 45394-45402 (2001).
Iben, L.G., et al., "Signal Peptide Peptidase and gamma-Secretase Share Equivalent Inhibitor Binding Pharmacology," The Journal of Biological Chemistry, vol. 282, No. 51, pp. 36829-36836 (2007).

(Continued)

*Primary Examiner* — Bruck Kifle
(74) *Attorney, Agent, or Firm* — Gary D. Greenblatt

(57) ABSTRACT

Disclosed are compounds of Formula (I): wherein: $R_1$ is $CH_2CH_2CF_3$; $R_2$ is $CH_2CH_2CF_3$, $CH_2$(cyclopropyl), or phenyl; $R_3$ is H or $CH_3$; Ring A is phenyl or pyridinyl; and $R_x$, $R_y$, $R_a$, $R_b$, y, and z are defined herein. Also disclosed are methods of using such compounds to inhibit the Notch receptor, and pharmaceutical compositions comprising such compounds. These compounds are useful in treating, preventing, or slowing the progression of diseases or disorders in a variety of therapeutic areas, such as cancer.

9 Claims, No Drawings

(56) References Cited

U.S. PATENT DOCUMENTS

| | | |
|---|---|---|
| 7,112,583 B2 | 9/2006 | Olson et al. |
| 7,125,866 B1 | 10/2006 | Glick et al. |
| 7,153,491 B2 | 12/2006 | Zaczek et al. |
| 7,160,875 B2 | 1/2007 | Flohr et al. |
| 7,276,495 B2 | 10/2007 | Han et al. |
| 7,276,496 B2 | 10/2007 | Olson et al. |
| 7,304,049 B2 | 12/2007 | Olson |
| 7,304,055 B2 | 12/2007 | Olson et al. |
| 7,304,056 B2 | 12/2007 | Olson et al. |
| 7,342,008 B2 | 3/2008 | Olson et al. |
| 7,354,914 B2 | 4/2008 | Olson |
| 7,375,099 B2 | 5/2008 | Galley et al. |
| 7,390,802 B2 | 6/2008 | Han et al. |
| 7,390,896 B2 | 6/2008 | Olson et al. |
| 7,423,033 B2 | 9/2008 | Olson et al. |
| 7,456,172 B2 | 11/2008 | Olson |
| 7,456,278 B2 | 11/2008 | Olson |
| 7,498,324 B2 | 3/2009 | Han et al. |
| 7,528,249 B2 | 5/2009 | Olson et al. |
| 7,544,679 B2 | 6/2009 | Flohr et al. |
| 7,582,624 B2 | 9/2009 | Carter et al. |
| 7,655,647 B2 | 2/2010 | Han et al. |
| 7,718,795 B2 | 5/2010 | Olson |
| 8,629,136 B2 | 1/2014 | Gavai et al. |
| 8,822,454 B2 | 9/2014 | Gavai et al. |
| 8,999,918 B2 | 4/2015 | Gavai et al. |
| 2007/0185094 A1 | 8/2007 | Lattmann et al. |
| 2009/0181944 A1 | 7/2009 | Boylan et al. |
| 2014/0357805 A1 | 12/2014 | Gavai et al. |

FOREIGN PATENT DOCUMENTS

| | | |
|---|---|---|
| WO | WO 01/74796 | 10/2001 |
| WO | WO 01/90084 | 11/2001 |
| WO | WO 2007/067048 | 6/2007 |
| WO | WO 2009/023453 | 2/2009 |
| WO | WO 2014/047370 | 3/2014 |
| WO | WO 2014/047374 | 3/2014 |
| WO | WO 2014/047390 | 3/2014 |
| WO | WO 2014/047391 | 3/2014 |
| WO | WO 2014/047392 | 3/2014 |
| WO | WO 2014/047393 | 3/2014 |
| WO | WO 2014/047397 | 3/2014 |

OTHER PUBLICATIONS

Meredith, Jere, "Characterization of APP Activity and Notch Toxicity with gamma-Secretase Inhibitors," 8th International AD/PD Meeting, Salzberg, Austria, Mar. 17, 2007.

Prasad, C.V.C., et al., "Discovery of (S)-2-((S)-2(3,5-difluorophenyl)-2-hydroxyacetamido)-N-((S,Z)-3-methyl-4-oxo-4,5-dihydro-3H-benzo[d][1,2]diazepin-5-yl)propanamide (BMS-433796): A gamma-secretase inhibitor with A beta lowering activity in a transgenic mouse model of Alzheimer's disease," Bioorganic & Medicinal Chemistry Letters 17 pp. 4006-4011 (2007).

Jun, H.T., et al., "Top NOTCH Targets: Notch Signaling in Cancer," Drug Development Research, 69, pp. 319-328 (2008).

Meredith, J.E., et al., gamma-Secretase activity is not involved in presenilin-mediated regulation of beta-catenin, Biochemical and Biophysical Research Communications 299 pp. 744-750 (2002).

Shih, L., et al., Notch Signaling, gamma-Secretase Inhibitors, and Cancer Therapy, Cancer Res. 67, pp. 1879-1882 (2007).

Olson, Richard, "Optimizing gamma-secretase Inhibitors for safety and efficacy," 8th International AD/PD Meeting, Mar. 14-18, 2007, Salzberg, Austria.

PCT/US2013/060781 International Search Report mailed Dec. 11, 2013.

PCT/US2013/060781 Preliminary Report on Patentability issued Mar. 24, 2015.

SUBSTITUTED 1,5-BENZODIAZEPINONES COMPOUNDS

This application is a national phase application under 35 U.S.C. §371 of International Patent Application No. PCT/US2013/060781, filed Sep. 20, 2013, which claims priority to U.S. Provisional Application 61/703,931, filed Sep. 21, 2012, which are expressly incorporated fully herein by reference.

DESCRIPTION

The present invention generally relates to benzodiazepinone compounds useful as Notch inhibitors. The invention further pertains to pharmaceutical compositions comprising at least one compound according to the invention that is useful for the treatment of conditions related to the Notch pathway, such as cancer and other proliferative diseases.

Notch signaling has been implicated in a variety of cellular processes, such as cell fate specification, differentiation, proliferation, apoptosis, and angiogenesis. (Bray, *Nature Reviews Molecular Cell Biology*, 7:678-689 (2006); Fortini, *Developmental Cell*, 16:633-647 (2009)). The Notch proteins are single-pass heterodimeric transmembrane molecules. The Notch family includes 4 receptors, NOTCH 1-4, which become activated upon binding to ligands from the DSL family (Delta-like 1, 3, 4 and Jagged 1 and 2).

The activation and maturation of NOTCH requires a series of processing steps, including a proteolytic cleavage step mediated by gamma secretase, a multiprotein complex containing Presenilin 1 or Presenilin 2, nicastrin, APH1, and PEN2. Once NOTCH is cleaved, NOTCH intracellular domain (NICD) is released from the membrane. The released NICD translocates to the nucleus, where it functions as a transcriptional activator in concert with CSL family members (RBPSUH, "suppressor of hairless", and LAG1). NOTCH target genes include HES family members, such as HES-1. HES-1 functions as transcriptional repressors of genes such as HERP1 (also known as HEY2), HERP2 (also known as HEY1), and HATH1 (also known as ATOH1).

The aberrant activation of the Notch pathway contributes to tumorigenesis. Activation of Notch signaling has been implicated in the pathogenesis of various solid tumors including ovarian, pancreatic, as well as breast cancer and hematologic tumors such as leukemias, lymphomas, and multiple myeloma. The role of Notch inhibition and its utility in the treatment of various solid and hematological tumors are described in Miele, L. et al., *Current Cancer Drug Targets*, 6:313-323 (2006); Bolos, V. et al., *Endocrine Reviews*, 28:339-363 (2007); Shih, I-M. et al., *Cancer Research*, 67:1879-1882 (2007); Yamaguchi, N. et al., *Cancer Research*, 68:1881-1888 (2008); Miele, L., *Expert Review Anticancer Therapy*, 8:1197-1201 (2008); Purow, B., *Current Pharmaceutical Biotechnology*, 10:154-160 (2009); Nefedova, Y. et al., *Drug Resistance Updates*, 11:210-218 (2008); Dufraine, J. et al., *Oncogene*, 27:5132-5137 (2008); and Jun, H. T. et al., *Drug Development Research*, 69:319-328 (2008).

There remains a need for compounds that are useful as Notch inhibitors and that have sufficient metabolic stability to provide efficacious levels of drug exposure. Further, there remains a need for compounds useful as Notch inhibitors that can be orally or intravenously administered to a patient.

U.S. Pat. No. 7,053,084 B1 discloses succinoylamino benzodiazepine compounds useful for treating neurological disorders such as Alzheimer's Disease. The reference discloses that these succinoylamino benzodiazepine compounds inhibit gamma secretase activity and the processing of amyloid precursor protein linked to the formation of neurological deposits of amyloid protein.

Applicants have found potent compounds that have activity as Notch inhibitors and have sufficient metabolic stability to provide efficacious levels of drug exposure upon intravenous or oral administration. These compounds are provided to be useful as pharmaceuticals with desirable stability, bioavailability, therapeutic index, and toxicity values that are important to their drugability.

SUMMARY OF THE INVENTION

The present invention fills the foregoing need by providing 1,5-benzodiazepinone compounds that are useful as selective inhibitors of Notch signaling pathway.

The present invention also provides pharmaceutical compositions comprising a pharmaceutically acceptable carrier; and at least one compound of Formula (I).

The present invention also provides a method of treating a disease or disorder associated with the activity of the Notch receptor, the method comprising administering to a mammalian patient at least one compound of Formula (I).

The present invention also provides processes and intermediates for making the compounds of Formula (I).

The present invention also provides the compounds of Formula (I) for use in therapy.

The present invention also provides the use of the compounds of Formula (I) for the manufacture of a medicament for the treatment of cancer.

The compounds of Formula (I) and compositions comprising the compounds are Notch inhibitors that may be used in treating, preventing or curing various Notch receptor-related conditions. Pharmaceutical compositions comprising these compounds are useful in treating, preventing, or slowing the progression of diseases or disorders in a variety of therapeutic areas, such as cancer.

These and other features of the invention will be set forth in expanded form as the disclosure continues.

DETAILED DESCRIPTION

The first aspect of the present invention provides at least one compound of Formula (I):

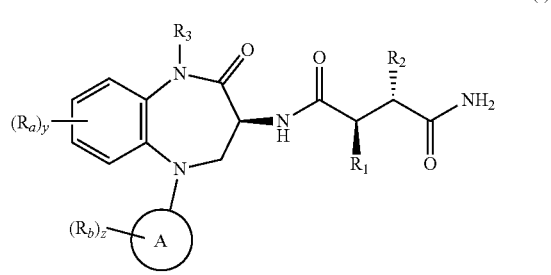

or at least one prodrug thereof, wherein:
$R_1$ is —$CH_2CH_2CF_3$;
$R_2$ is —$CH_2CH_2CF_3$, —$CH_2$(cyclopropyl), or phenyl;
$R_3$ is H or —$CH_3$;
Ring A is phenyl or pyridinyl;
each $R_a$ is independently F, Cl, —CN, —$CHF_2$, or cyclopropyl;

each $R_b$ is independently F, Cl, —CN, —CH$_3$, —CHF$_2$, —CF$_3$, or cyclopropyl;
y is zero, 1, or 2; and
z is zero, 1, or 2.

One embodiment provides at least one compound of Formula (I) wherein $R_3$ is H and $R_1$, $R_2$, $R_a$, $R_b$, y, and z are defined in the first aspect. Included in this embodiment are compounds in which $R_2$ is —CH$_2$CH$_2$CF$_3$. Also included in this embodiment are compounds in which $R_2$ is —CH$_2$CH$_2$CF$_3$ and Ring A is phenyl.

One embodiment provides at least one compound of Formula (I) wherein $R_2$ is —CH$_2$CH$_2$CF$_3$ and $R_1$, $R_3$, $R_a$, $R_b$, y, and z are defined in the first aspect. Included in this embodiment are compounds in which $R_3$ is H, Ring A is phenyl, and y is zero or 1. Also included in this embodiment are compounds in which $R_3$ is H, Ring A is pyridinyl, and y is zero or 1.

One embodiment provides at least one compound of Formula (I) wherein $R_2$ is —CH$_2$(cyclopropyl) and $R_1$, $R_3$, $R_a$, $R_b$, y, and z are defined in the first aspect. Included in this embodiment are compounds in which $R_3$ is H, Ring A is phenyl, and y is zero or 1. Also included in this embodiment are compounds in which $R_3$ is H, Ring A is pyridinyl, and y is zero or 1.

One embodiment provides at least one compound of Formula (I) wherein $R_2$ is phenyl and $R_1$, $R_3$, $R_a$, $R_b$, y, and z are defined in the first aspect. Included in this embodiment are compounds in which $R_3$ is H, Ring A is phenyl, and y is zero or 1. Also included in this embodiment are compounds in which $R_3$ is H, Ring A is pyridinyl, and y is zero or 1.

One embodiment provides at least one compound of Formula (I) having the structure:

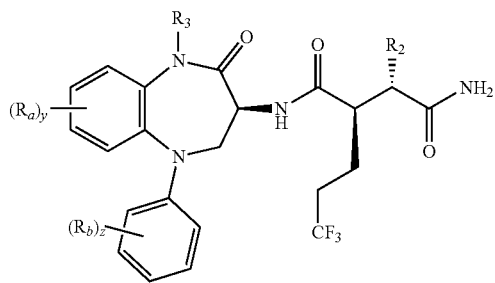

wherein Ring A is phenyl and $R_2$, $R_3$, $R_a$, $R_b$, y, and z are defined in the first aspect.

One embodiment provides a compound of Formula (I), wherein $R_3$ is H; and $R_1$, $R_2$, $R_a$, $R_b$, y, and z are defined in the first aspect. Included in this embodiment are compounds in which $R_3$ is deuterium (D) or tritium (T).

One embodiment provides a compound of Formula (I) wherein $R_3$ is —CH$_3$; and $R_1$, $R_2$, $R_a$, $R_b$, y, and z are defined in the first aspect. $R_3$ includes methyl groups in which one or more hydrogen atoms are isotopically substituted with deuterium (D) and/or tritium (T). In one example of this embodiment, $R_3$ is —CD$_3$. Also included in this embodiment are compounds in which $R_2$ is —CH$_2$CH$_2$CF$_3$.

One embodiment provides a compound of Formula (I) selected from: (2R,3S)—N-((3S)-6-chloro-1-(3-cyclopropylphenyl)-4-oxo-2,3,4,5-tetrahydro-1H-1,5-benzodiazepin-3-yl)-2,3-bis(3,3,3-trifluoropropyl)succinamide (1); (2R,3R)—N-((3S)-1-(3-cyanophenyl)-6-(difluoromethyl)-4-oxo-2,3,4,5-tetrahydro-1H-1,5-benzodiazepin-3-yl)-3-phenyl-2-(3,3,3-trifluoropropyl)succinamide(2); (2R,3S)—N-((3S)-1-(3-chlorophenyl)-4-oxo-2,3,4,5-tetrahydro-1H-1,5-benzodiazepin-3-yl)-2,3-bis(3,3,3-trifluoropropyl)succinamide (3); (2R,3S)—N-((3S)-1-(4-chlorophenyl)-4-oxo-2,3,4,5-tetrahydro-1H-1,5-benzodiazepin-3-yl)-2,3-bis(3,3,3-trifluoropropyl)succinamide (4); (2R,3S)—N-((3S)-1-(3-cyclopropylphenyl)-4-oxo-2,3,4,5-tetrahydro-1H-1,5-benzodiazepin-3-yl)-2,3-bis(3,3,3-trifluoropropyl)succinamide (5); (2R,3S)—N-((3S)-1-(4-fluorophenyl)-4-oxo-2,3,4,5-tetrahydro-1H-1,5-benzodiazepin-3-yl)-2,3-bis(3,3,3-trifluoropropyl)succinamide (6); (2R,3S)—N-((3S)-1-(3-chlorophenyl)-6-cyclopropyl-4-oxo-2,3,4,5-tetrahydro-1H-1,5-benzodiazepin-3-yl)-2,3-bis(3,3,3-trifluoropropyl)succinamide (7); (2R,3R)—N-((3S)-6-cyano-4-oxo-1-(3-(trifluoromethyl)phenyl)-2,3,4,5-tetrahydro-1H-1,5-benzodiazepin-3-yl)-3-phenyl-2-(3,3,3-trifluoropropyl)succinamide (8); (2R,3R)—N-((3S)-1-(3-chloro-5-cyanophenyl)-6-(difluoromethyl)-4-oxo-2,3,4,5-tetrahydro-1H-1,5-benzodiazepin-3-yl)-3-phenyl-2-(3,3,3-trifluoropropyl)succinamide (9); (2R,3S)—N-((3S)-1-(3-cyanophenyl)-6-(difluoromethyl)-4-oxo-2,3,4,5-tetrahydro-1H-1,5-benzodiazepin-3-yl)-2,3-bis(3,3,3-trifluoropropyl)succinamide (10); (2R,3R)—N-((3S)-1-(3-cyano-5-methylphenyl)-6-(difluoromethyl)-4-oxo-2,3,4,5-tetrahydro-1H-1,5-benzodiazepin-3-yl)-3-phenyl-2-(3,3,3-trifluoropropyl)succinamide (11); (2R,3S)—N-((3S)-6-(difluoromethyl)-1-(3-(difluoromethyl)phenyl)-4-oxo-2,3,4,5-tetrahydro-1H-1,5-benzodiazepin-3-yl)-2,3-bis(3,3,3-trifluoropropyl)succinamide (12); (2R,3R)—N-(1-(3-cyano-5-fluorophenyl)-6-(difluoromethyl)-4-oxo-2,3,4,5-tetrahydro-1H-1,5-benzodiazepin-3-yl)-3-phenyl-2-(3,3,3-trifluoropropyl)succinamide (13); (2R,3S)-3-(cyclopropylmethyl)-N-((3S)-6-fluoro-4-oxo-1-(3-(trifluoromethyl)phenyl)-2,3,4,5-tetrahydro-1H-1,5-benzodiazepin-3-yl)-2-(3,3,3-trifluoropropyl)succinamide (14); (2R,3S)-3-(cyclopropylmethyl)-N-((3S)-1-(3-cyclopropylphenyl)-6-fluoro-4-oxo-2,3,4,5-tetrahydro-1H-1,5-benzodiazepin-3-yl)-2-(3,3,3-trifluoropropyl)succinamide (15); (2R,3S)-3-(cyclopropylmethyl)-N-((3S)-1-(3,4-dichlorophenyl)-6-fluoro-4-oxo-2,3,4,5-tetrahydro-1H-1,5-benzodiazepin-3-yl)-2-(3,3,3-trifluoropropyl)succinamide (16); (2R,3S)—N-((3S)-1-(3-cyanophenyl)-6-fluoro-4-oxo-2,3,4,5-tetrahydro-1H-1,5-benzodiazepin-3-yl)-2,3-bis(3,3,3-trifluoropropyl)succinamide (17); (2R,3R)—N-((3S)-1-(3-cyanophenyl)-6-fluoro-4-oxo-2,3,4,5-tetrahydro-1H-1,5-benzodiazepin-3-yl)-3-phenyl-2-(3,3,3-trifluoropropyl)succinamide (18); (2R,3S)—N-((3S)-6-chloro-1-(4-chlorophenyl)-4-oxo-2,3,4,5-tetrahydro-1H-1,5-benzodiazepin-3-yl)-3-(cyclopropylmethyl)-2-(3,3,3-trifluoropropyl)succinamide (19); (2R,3S)—N-((3S)-6-chloro-4-oxo-1-(3-(trifluoromethyl)phenyl)-2,3,4,5-tetrahydro-1H-1,5-benzodiazepin-3-yl)-2,3-bis(3,3,3-trifluoropropyl)succinamide (20); (2R,3S)—N-((3S)-6-chloro-4-oxo-1-(3-(trifluoromethyl)phenyl)-2,3,4,5-tetrahydro-1H-1,5-benzodiazepin-3-yl)-3-(cyclopropylmethyl)-2-(3,3,3-trifluoropropyl)succinamide (21); (2R,3R)—N-((3S)-6-chloro-4-oxo-1-(3-(trifluoromethyl)phenyl)-2,3,4,5-tetrahydro-1H-1,5-benzodiazepin-3-yl)-3-phenyl-2-(3,3,3-trifluoropropyl)succinamide (22); (2R,3S)—N-((3S)-6-chloro-1-(3-cyanophenyl)-4-oxo-2,3,4, 5-tetrahydro-1H-1,5-benzodiazepin-3-yl)-2,3-bis(3,3,3-trifluoropropyl)succinamide (23); (2R,3R)—N-((3S)-6-chloro-1-(3-cyanophenyl)-4-oxo-2,3,4,5-tetrahydro-1H-1,5-benzodiazepin-3-yl)-3-phenyl-2-(3,3,3-trifluoropropyl)succinamide (24); (2R,3S)—N-((3S)-6-chloro-1-(3-cyanophenyl)-4-oxo-2,3,4,5-tetrahydro-1H-1,5-benzodiazepin-3-yl)-3-(cyclopropylmethyl)-2-(3,3,3-trifluoropropyl)succinamide (25); (2R,3S)—N-((3S)-6-chloro-1-(2-cyanophenyl)-4-oxo-2,3,4,5-tetrahydro-1H-1,5- benzodiazepin-3-yl)-3-(cyclopropylmethyl)-2-(3,3,3-trifluoropropyl)succinamide (26); (2R,3R)—N-((3S)-6-chloro-1-(3-cyano-5-fluorophenyl)-4-oxo-2,3,4,5-tetrahydro-1H-1,5-benzodiazepin-3-yl)-3-phenyl-2-(3,3,3-trifluoropropyl)succinamide (27); (2R,3S)—N-((3S)-6-chloro-1-(3-cyano-5-fluorophenyl)-4-oxo-2,3,4,5-tetrahydro-1H-1,5-benzodiazepin-3-yl)-3-(cyclopropylmethyl)-2-(3,3,3-trifluoropropyl)succinamide (28); (2R,3S)—N-((3S)-6-chloro-1-(3-cyclopropylphenyl)-4-oxo-2,3,4,5-tetrahydro-1H-1,5-benzodiazepin-3-yl)-3-(cyclopropylmethyl)-2-(3,3,3-trifluoropropyl)succinamide (29); (2R,3R)—N-((3S)-6-chloro-1-(3,4-dichlorophenyl)-4-oxo-2,3,4,5-tetrahydro-1H-1,5-benzodiazepin-3-yl)-3-phenyl-2-(3,3,3-trifluoropropyl)succinamide (30); (2R,3S)—N-((3S)-6-chloro-1-(3-chlorophenyl)-4-oxo-2,3,4,5-tetrahydro-1H-1,5-benzodiazepin-3-yl)-2,3-bis(3,3,3-trifluoropropyl)succinamide (31); (2R,3S)—N-((3S)-6-chloro-1-(3,4-dichlorophenyl)-4-oxo-2,3,4,5-tetrahydro-1H-1,5-benzodiazepin-3-yl)-2,3-bis(3,3,3-trifluoropropyl)succinamide (32); (2R,3S)—N-((3S)-6-chloro-4-oxo-1-(2-pyridinyl)-2,3,4,5-tetrahydro-1H-1,5-benzodiazepin-3-yl)-2,3-bis(3,3,3-trifluoropropyl)succinamide (33); (2R,3R)—N-((3S)-6-chloro-4-oxo-1-(6-(trifluoromethyl)-2-pyridinyl)-2,3,4,5-tetrahydro-1H-1,5-benzodiazepin-3-yl)-3-phenyl-2-(3,3,3-trifluoropropyl)succinamide (34); (2R,3S)—N-((3S)-6-chloro-4-oxo-1-(6-(trifluoromethyl)-2-pyridinyl)-2,3,4,5-tetrahydro-1H-1,5-benzodiazepin-3-yl)-2,3-bis(3,3,3-trifluoropropyl)succinamide (35); (2R,3R)—N-((3S)-6-chloro-4-oxo-1-(4-(trifluoromethyl)-2-pyridinyl)-2,3,4,5-tetrahydro-1H-1,5-benzodiazepin-3-yl)-3-phenyl-2-(3,3,3-trifluoropropyl)succinamide (36); (2R,3S)—N-((3S)-7-fluoro-4-oxo-1-phenyl-2,3,4,5-tetrahydro-1H-1,5-benzodiazepin-3-yl)-2,3-bis(3,3,3-trifluoropropyl)succinamide (37); and (2R,3S)—N-((3S)-7-fluoro-4-oxo-1-(3-(trifluoromethyl)phenyl)-2,3,4,5-tetrahydro-1H-1,5-benzodiazepin-3-yl)-2,3-bis(3,3,3-trifluoropropyl)succinamide (38).

One embodiment provides at least one compound of Formula (I) having a metabolic half life value of at least 45 minutes as measured in the human metabolic stability half-life assay described herein.

One embodiment provides at least one compound of Formula (I) having a metabolic half life value of at least 60 minutes as measured in the human metabolic stability half-life assay described herein.

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe addition more embodiments. It is also to be understood that each individual element of the embodiments is meant to be combined with any and all other elements from any embodiment to describe an additional embodiment.

DEFINITIONS

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

The terms "halo" and "halogen", as used herein, refer to F, Cl, Br, or I.

The term "alkyl" as used herein, refers to both branched and straight chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Any compound that can be converted in vivo to provide the bioactive agent (i.e., the compound of Formula (I)) is a prodrug within the scope and spirit of the invention. The compounds of Formula (I) in which either $R_3$ is $R_x$ or $R_4$ is $R_y$ are useful as prodrugs of the compounds of Formula (I) in which $R_3$ is H or —$CH_3$ and $R_4$ is H.

Various forms of prodrugs are well known in the art and are described in:
a) Wermuth, C. G. et al., *The Practice of Medicinal Chemistry*, Chapter 31, Academic Press (1996);
b) Bundgaard, H. ed., *Design of Prodrugs*, Elsevier (1985);
c) Bundgaard, H., Chapter 5, "Design and Application of Prodrugs", Krogsgaard-Larsen, P. et al., eds., *A Textbook of Drug Design and Development*, pp. 113-191, Harwood Academic Publishers (1991); and
d) Testa, B. et al., *Hydrolysis in Drug and Prodrug Metabolism*, Wiley-VCH (2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to a NOTCH receptor, or effective to treat or prevent proliferative diseases such as cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising the compound of Formula (I); and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 1 to 2000 mg, preferably from about 1 to 500 mg, and more preferably from about 5 to 150 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.005 and about 50 mg/kg body weight and most preferably between about 0.01 to 10 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise the compound of Formula (I), or a prodrug thereof, and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

UTILITY

The compounds of Formula (I) are useful for the treatment of cancer, for example, cancers dependent upon Notch activation. Notch activation has been implicated in the pathogenesis of various solid tumors including ovarian, pancreatic, as well as breast cancer and hematologic tumors such as leukemias, lymphomas, and multiple myeloma.

In one embodiment, a method is provided for treating cancer comprising administering to a mammal in need thereof a compound of Formula (I). The method of this embodiment can be used to treat a variety of cancers, including, but not limited to, bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. For example, the method of this embodiment is used to treat breast cancer, colon cancer, or pancreatic cancer. Preferably, the mammal is a human. For example, a therapeutically effective amount for treating cancer may be administered in the method of the present embodiment.

Routes of administration in the present embodiment include parenteral administration and oral administration.

In one embodiment, a method is provided for treating cancer comprising administering to a mammal in need thereof at least one compound of Formula (I), wherein said cancer is colorectal cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I), wherein said cancer is triple negative breast cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I), wherein said cancer is non-small cell lung cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I), wherein said cancer is pancreatic cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I), wherein said cancer is ovarian cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I), wherein said cancer is melanoma. Preferably, the mammal is a human. For example, a therapeutically effective amount for treating cancer may be administered in the method of the present embodiment. Routes of administration in the present embodiment include parenteral administration and oral administration.

In one embodiment, the use of at least one compound of Formula (I), in the manufacture of a medicament for the treatment of cancer is provided. Preferably, in the present embodiment, cancers subject to treatment include one or more of bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. Suitable medicaments of the present embodiment include medicaments for parenteral administration, such as, for example, solutions and suspensions and medicaments for oral administration, such as, for example, tablets, capsules, solutions, and suspensions.

One embodiment at least one compound of Formula (I), for use in therapy in treating cancer. In the present embodiment, cancers subject to treatment include one or more of bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma.

In one embodiment, a method is provided for treating cancer in a mammal wherein the cancer is dependent upon Notch activation, comprising administering to the patient at least one compound of Formula (I). The method of this embodiment can be used to treat a variety of cancers, including, but not limited to, bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. Preferably, the method of this embodiment is used to treat breast cancer, colon cancer, or pancreatic cancer. Preferably, the mammal is a human. For example, a therapeutically effective amount for treating cancer may be administered in the method of the present embodiment. Suitable routes of administration include parenteral administration and oral administration.

In treating cancer, a combination of chemotherapeutic agents and/or other treatments (e.g., radiation therapy) is often advantageous. The second (or third) agent may have the same or different mechanism of action than the primary therapeutic agent. For example, drug combinations may be employed wherein the two or more drugs being administered act in different manners or in different phases of the cell cycle, and/or where the two or more drugs have nonoverlapping toxicities or side effects, and/or where the drugs being combined each has a demonstrated efficacy in treating the particular disease state manifested by the patient.

In one embodiment, a method is provided for treating cancer comprising administering to a mammal in need thereof at least one compound of Formula (I); and administering one or more additional anticancer agents.

The phrase "additional anticancer agent" refers to a drug selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MET inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

Accordingly, the compounds of the present invention may be administered in combination with other anti-cancer treatments useful in the treatment of cancer or other proliferative diseases. The invention herein further comprises use of at least one compound of Formula (I) in preparing medicaments for the treatment of cancer, and/or it comprises the packaging of a compound of Formula (I) herein together with instructions that the compound be used in combination with other anti-cancer or cytotoxic agents and treatments for the treatment of cancer. The present invention further comprises combinations of at least one compound of Formula (I); and one or more additional agents in kit form, e.g., where they are packaged together or placed in separate packages to be sold together as a kit, or where they are packaged to be formulated together.

In one embodiment, a method is provided for treating cancer comprising administering to a mammal in need thereof at least one compound of Formula (I); administering dasatinib; and optionally, one or more additional anticancer agents.

In one embodiment, a method is provided for treating cancer comprising administering to a mammal in need thereof at least one compound of Formula (I); administering paclitaxel; and optionally, one or more additional anticancer agents.

In one embodiment, a method is provided for treating cancer comprising administering to a mammal in need thereof at least one compound of Formula (I); administering tamoxifen; and optionally, one or more additional anticancer agents.

In one embodiment, a method is provided for treating cancer comprising administering to a mammal in need thereof at least one compound of Formula (I); administering a glucocorticoid; and optionally, one or more additional anticancer agents. An example of a suitable glucocorticoid is dexamethasone.

In one embodiment, a method is provided for treating cancer comprising administering to a mammal in need thereof at least one compound of Formula (I); administering carboplatin; and optionally, one or more additional anticancer agents.

The compounds of the present invention can be formulated or co-administered with other therapeutic agents that are selected for their particular usefulness in addressing side effects associated with the aforementioned conditions. For example, compounds of the invention may be formulated with agents to prevent nausea, hypersensitivity and gastric irritation, such as antiemetics, and $H_1$ and $H_2$ antihistaminics.

In one embodiment, pharmaceutical compositions are provided comprising at least one compound of Formula (I); one or more additional agents selected from a kinase inhibitory agent (small molecule, polypeptide, and antibody), an immunosuppressant, an anticancer agent, an anti-viral agent, anti-inflammatory agent, antifungal agent, antibiotic, or an anti-vascular hyperproliferation compound; and any pharmaceutically acceptable carrier, adjuvant or vehicle.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The specific dose level and frequency of dosage for any particular subject however, may be varied and generally depends on a variety of factors, including, but not limited to, for example, the bioavailability of the specific compound of Formula (I) in the administered form, metabolic stability and length of action of the specific compound of Formula (I), species, body weight, general health, sex, diet of subject, mode and time of administration, rate of excretion, drug combination, and severity of the particular condition. For example, a daily dose of about 0.001 to 100 mg/kg body weight, preferably between about 0.005 and about 50 mg/kg body weight and most preferably between about 0.01 to 10 mg/kg body weight, may be appropriate. The daily dose can be administered in one to four doses per day.

The administration can be continuous, i.e., every day, or intermittently. The terms "intermittent" or "intermittently" as used herein mean stopping and starting at either regular or irregular intervals. For example, intermittent administration includes administration one to six days per week; administration in cycles (e.g., daily administration for two to eight consecutive weeks followed by a rest period with no administration for up to one week); or administration on alternate days.

In one embodiment, the at least one compound of Formula (I) is administered continuously to a patient in need thereof, one or more times daily. For example, a therapeutically effective amount of the compound of Formula (I) is administered to a patient in need thereof, one or more times daily for continuous days.

In one embodiment, the at least one compound of Formula (I) is administered intermittently to a patient in need thereof, one or more times daily. For example, a therapeutically effective amount of the compound of Formula (I) is administered to a patient in need thereof, one or more times daily according to an intermittent schedule.

In one embodiment, the at least one compound of Formula (I) is administered to a patient in need thereof, one or more times daily for continuous days followed by one or more days without administration. Preferably, a therapeutically effective amount of the compound of Formula (I) is administered. Examples of continuous dosing with a drug holiday are cycles of: 7 days on treatment followed by 7 days off treatment; 14 days on treatment followed by 7 days off treatment; and 7 days on treatment followed by 14 days off treatment. A cycle of on treatment/off treatment can be repeated multiple times as required to treat a patient.

In one embodiment, at least one compound of Formula (I) is administered to a patient in need thereof, according to an intermittent dosing schedule. Intermittent dosing schedules are repeating schedules including days in which the patient is administered the compound of Formula (I) and days in which the patient is not administered the compound of Formula (I). Examples of intermittent dosing schedules are: dosing four days each week for three continuous weeks followed by a week without dosing, and repeating on a four week interval; dosing five days each week for two continuous weeks followed by a week without dosing, and repeating on a three week interval; and dosing four days each week for one week followed by two weeks without dosing, and repeating on a three week interval. Preferably, a therapeutically effective amount of the compound of Formula (I) is administered.

In one embodiment, at least one compound of Formula (I) is administered on one day, followed by 6 days of rest, and repeated on a weekly schedule.

In one embodiment, at least one compound of Formula (I) is administered on one day, followed by 6 days of rest, and repeated on a weekly schedule for 1 to 4 weeks, and then followed by one week or rest. For example, the compound of Formula (I) is administered on one day, followed by 6 days of rest for three weeks, and then followed by one week of rest. This four week cycle can be repeated one or more times.

In one embodiment, at least one compound of Formula (I) is administered on two consecutive days, followed by 5 days of rest, and repeated on a weekly schedule.

In one embodiment, at least one compound of Formula (I) is administered on three consecutive days followed by four days of rest, and repeated on a weekly schedule.

In one embodiment, at least one compound of Formula (I) is administered on one day, followed by 10 to 13 days of rest.

In one embodiment, at least one compound of Formula (I) is administered once each day (QD). This embodiment includes once daily oral administration.

In one embodiment, at least one compound of Formula (I) is administered twice each day (BID). This embodiment includes twice daily oral administration.

In one embodiment, at least one compound of Formula (I) is administered on alternate days: one day on followed by one day of rest. This two day cycle can be repeated one or more times.

METHODS OF PREPARATION

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

The synthesis of the compounds of Formula (I) can be made using the methods summarized in Schemes 1 to 5.

Scheme 1

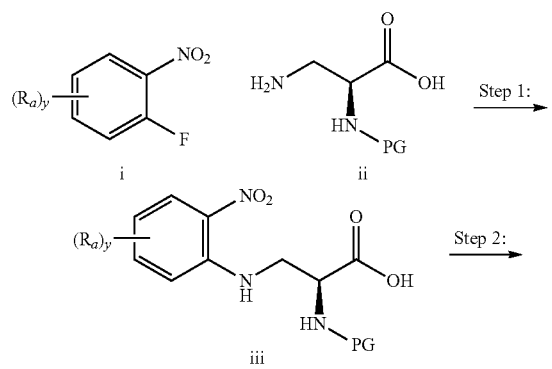

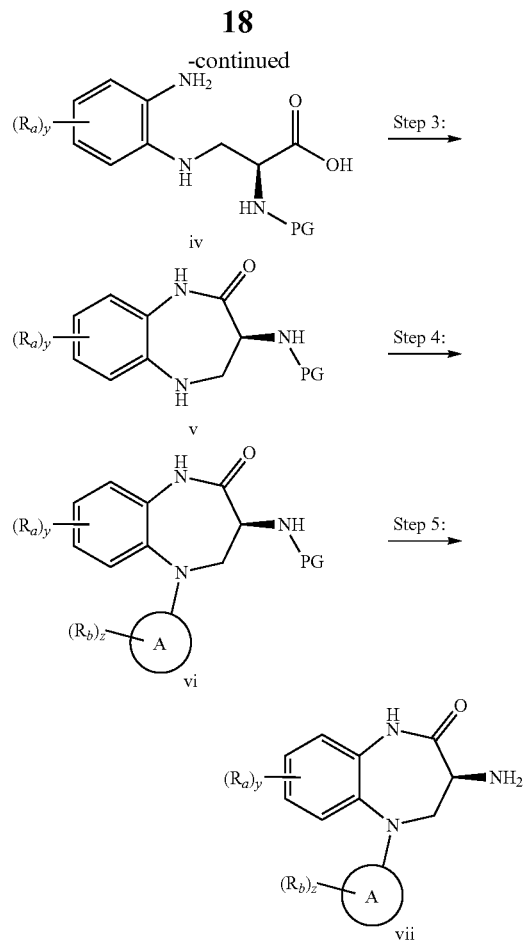

Step 1: The preparation of benzodiazepinones (vii) may be accomplished in multitude of methods known to one skilled in the art. For example, as shown in Scheme 1, the first step may be accomplished by using an appropriately substituted 2-fluoronitrobenzene (i) that may be coupled to a protected amino acid derivative (ii) (PG=protecting group, for example PG=Boc) in the presence of a base such as potassium carbonate in an appropriate solvent (for example ethanol) at an appropriate temperature such as 80° C.

Step 2: The second step of the sequence is a reduction of the nitro moiety. Nitroaromatic (iii) can be reduced in a variety of methods, for example hydrogenation with Pd/C, with iron or other metals in the presence of a hydrogen source such as ammonium chloride in an appropriate solvent such as ethanol, or other methods known to one skill in the art, to provide compound iv.

Step 3: Compound iv can be cyclized to benzodiazepinone v in several ways. For example, Compound iv can be treated with a coupling agent such as TBTU, EDC/HOBt, EDC/HOAt or other similar coupling reagents, in the presence of a base such as triethylamine in an appropriate solvent such as DMF.

Step 4: Compound v can be converted to compound vi using an appropriate coupling partner, such as an appropriately substituted aryl halide, in the presence of a catalyst such as Pd$_2$(dba)$_3$ and a ligand such as 2-(dicyclohexylphosphino)-2',4',6'-triisopropylbiphenyl ("X-Phos"), or a precatalyst such as [PdCl(NH$_2$C$_6$H$_4$C$_6$H$_4$)(XPhos)], with or without additional ligand such as Ruphos, in the presence of a base such as potassium carbonate in an appropriate solvent such as t-BuOH at an appropriate temperature such as 80° C.

Step 5: Compound vii can be obtained by treating compound vi under suitable conditions known to one skilled in the art to remove the protecting group. For example, compound vi can be treated with a strong acid such as TFA in an appropriate solvent such as CH$_2$Cl$_2$. The resulting TFA salts can be used as such, or can be treated in such a manner as to free-base the material, for example by treating with a base such as saturated NaHCO$_3$ solution and extracting compound vii.

per at a low temperature such as −78° C. under an inert atmosphere such as N$_2$ and warmed to room temperature to provide compound (xv).

Step 4: Conversion of compound (xv) to (xvi) may be accomplished by treating it with hydrogen peroxide and lithium hydroxide at an appropriate temperature using a mixture of solvents such as THF/water. If necessary, the diastereomers may be separated at this point via silica gel chroma- Scheme 2

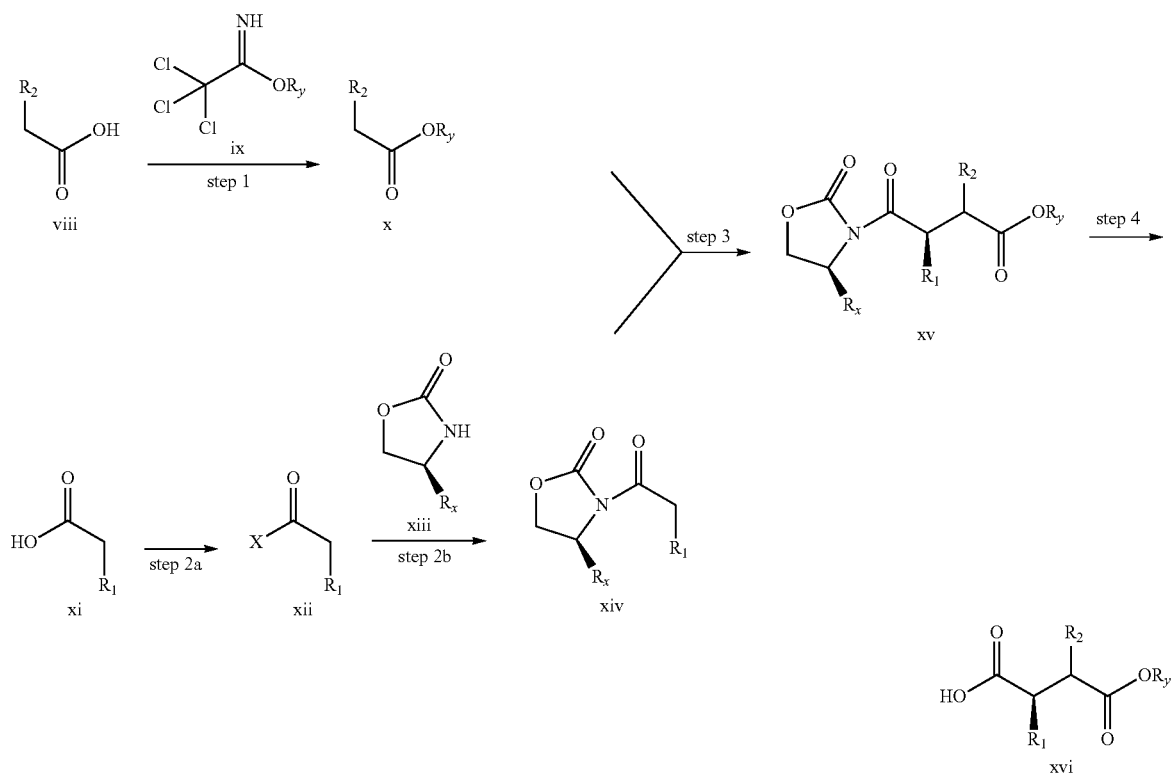

Step 1: The first step of Scheme 2 is accomplished by converting compound (viii) to the ester (x), employing one of the multiple ways known to one skilled in the art, such as treatment with a substituted acetimidate such as compound (ix) in the presence of a reagent such as boron trifluoride etherate at an appropriate temperature in a solvent such as THF.

Step 2: Acid (xi) can be converted to compound (xiv) in multiple ways known to one skilled in the art. For example, treatment of acid (xi) with a reagent such as oxalyl chloride in a solvent such as DCM gives the acid chloride (xii). Compound (xii) can be treated with an oxazolidinone (xiii) under standard conditions to give compound (xiv) (Evans, D. A. et al., *J. Am. Chem. Soc.*, 112:4011 (1990)).

Step 3: Compound (xiv) can be converted to compound (xv) in multiple ways (Baran, P. et al., *J. Am. Chem. Soc.*, 130(34):11546 (2008)). For example, compound (x) is treated with a base such as LDA in a solvent such as toluene, at low temperature such as −78° C. under an inert atmosphere such as N$_2$. The resulting mixture is added to a solution of compound (xiv) treated with lithium chloride and a base such as LDA in a solvent such as toluene under an inert atmosphere such as N$_2$. To the resulting mixture of the enolates of compounds (x) and (xiv) is added bis(2-ethylhexanoyloxy) coptography or preparative HPLC. Alternately, the mixture may be subjected to epimerization conditions, for example by treatment with LDA and diethylaluminum chloride followed by quenching with methanol or acetic acid to enrich the desired diastereomer.

Scheme 3

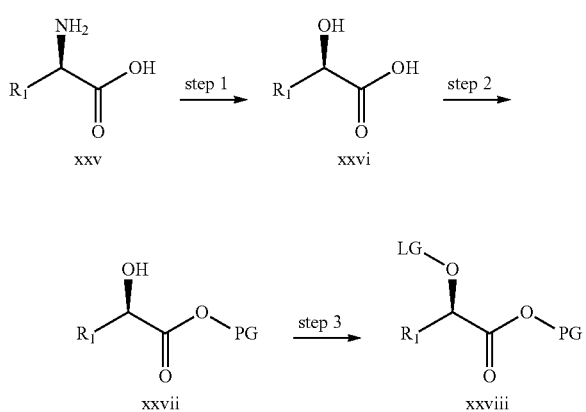

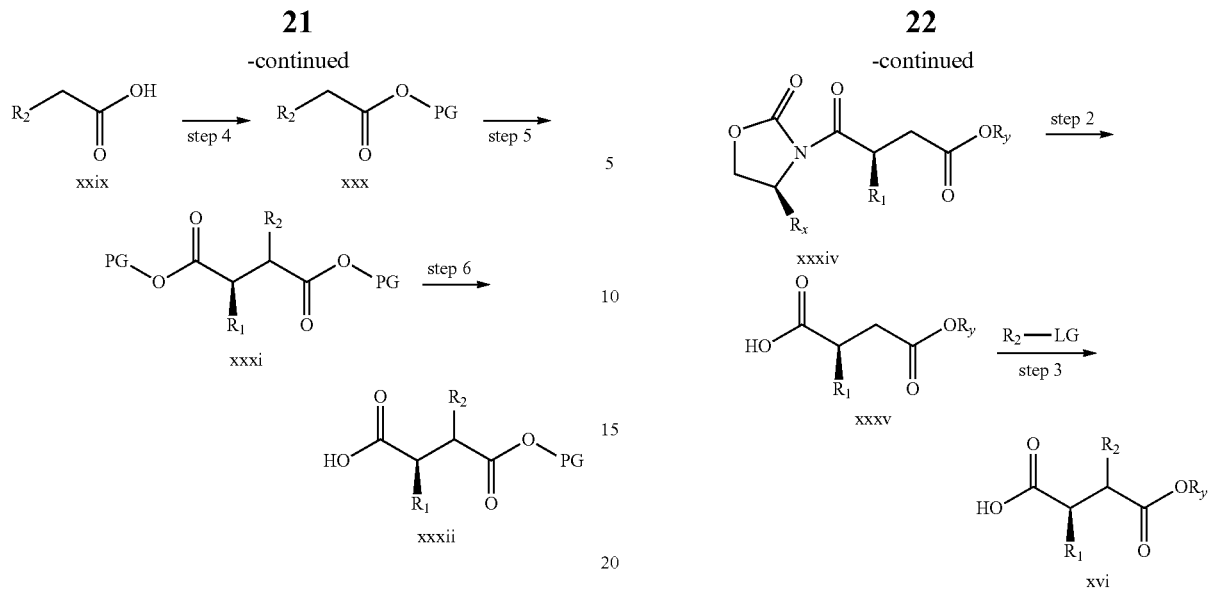

Step 1: The first step of Scheme 5 is accomplished by treating Compound (xxv) with a reagent such as sodium nitrite in an acid such as H₂SO₄ and a solvent such as water to provide Compound xxvi.

Step 2: The acid (xxvi) is converted to compound (xxvii) (PG=protecting group). For example, the acid (xxvi) is treated with an alcohol such as benzyl alcohol in a solvent such as toluene and an acid such as H₂SO₄ to provide Compound xxvii.

Step 3: Compound (xxviii) bearing a suitable leaving group may be prepared by treatment of Compound (xxvii) with a base such as 2,6-lutidine and a reagent such as trifluoromethanesulfonic anhydride in a solvent such as DCM at an appropriate temperature.

Step 4: Compound (xxix) can be converted to Compound (xxx) in multiple ways known to one skilled in the art, with, for example, a substituted acetimidate such as compound (ix) in the presence of a reagent such as boron trifluoride etherate at an appropriate temperature in a solvent such as THF.

Step 5: The preparation of Compound (xxxi) may be effected by treating Compound (xxx) with a base such as LiHMDS in a solvent such as THF at an appropriate temperature such as −78° C. and to the resulting mixture is added Compound (xxviii) in a solvent such as THF.

Step 6: The protecting group of Compound (xxxi) may be removed via many methods known to one skilled in the art. For example, a benzyl group may be removed by subjecting it to hydrogenation conditions using a palladium catalyst such as Pearlman's Catalyst in a solvent such as methanol to provide Compound (xxxii).

Compound (xvi) in Scheme 2 may also be prepared from compound (xxxiii) by synthetic sequence outlined in Scheme 4.

Step 1: The first step of Scheme 4 is accomplished by treating Compound (xxxiii) with a base such as sodium bis(trimethylsilyl)-amide in a solvent such as THF at low temperature such as −78° C. under an inert atmosphere. To the resulting enolate of (xxxiii) is treated with a reagent such as tert-butyl bromoacetate to provide compound (xxxiv).

Step 2: Conversion of compound (xxxiv) to (xxxv) may be accomplished by treating compound (xxxiv) with hydrogen peroxide and lithium hydroxide at an appropriate temperature using a mixture of solvents such as THF/water.

Step 3: Compound (xxxv) can be converted to compound (xvi) by generating the enolate of (xxxv) with a base such as LDA in a solvent such as THF at low temperature such as −78° C. under an inert atmosphere and further treatment with a reagent (R₂-LG) bearing an appropriate leaving group (e.g., LG=triflate).

Scheme 5

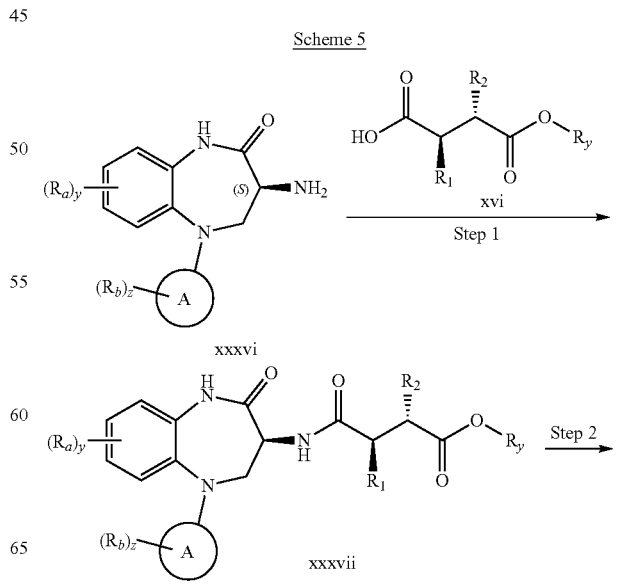

Scheme 4

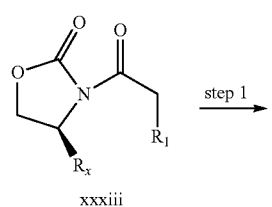

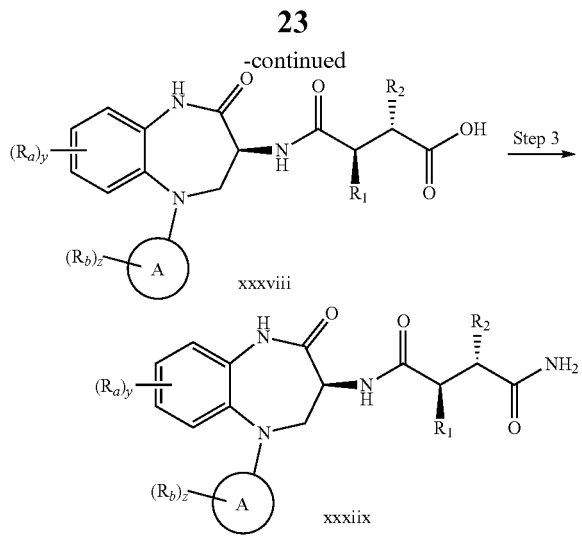

Examples in this invention may be made with the intermediates prepared in the general schemes 1-4, using methods known to one skilled in the art.

Step 1: The first step entails the coupling of an appropriately substituted compound xxxvi with an appropriately substituted mono-protected compound xvi. For example, Compound (xvi) may be coupled with compound xxxvi in the presence of a coupling reagent such as TBTU and a base such as TEA, in a solvent such as DMF to provide compound xxxvii.

Step 2: The conversion of compound xxxvii to compound xxxviii can be accomplished in numerous methods known to one skilled in the art. For example, the tert-butyl ester of compound xxxvii can be treated with an acid such as TFA at an appropriate temperature such as 0° C., in a solvent such as DCM provides compound xxxviii.

Step 3: Conversion of compound xxxviii to compound xxxiix may be accomplished via coupling of compound xxxviii with an appropriate amine source such as ammonia, a carbodiimide such as EDC, HOBT in a solvent such as DMF. If necessary the diastereomeric mixture can be separated using an appropriate separation technique, such as chiral preparative chromatography.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

ABBREVIATIONS

AcOH acetic acid
ACN acetonitrile
AlMe$_3$ trimethyl aluminum
Boc tert-butyloxycarbonyl
DCC 1,3-dicyclohexylcarbodiimide
DCM dichloromethane
DEA diethylamine
DMAP dimethylaminopyridine
DME 1,2-dimethoxyethane
DMF dimethylformamide
DMSO dimethyl sulfoxide
EDC 1-(3-dimethylaminopropyl)-3-ethylcarbodiimide hydrochloride
EDCI 1-(3-dimethylaminopropyl)-3-ethylcarbodiimide
Et$_2$AlCl diethyl aluminum chloride
EtOAc ethyl acetate
H$_2$SO$_4$ sulfuric acid
HCl hydrochloric acid
HOBT hydroxybenzotriazole
HPLC High Performance Liquid Chromatography
hr hour(s)
IPA isopropyl alcohol
LCMS Liquid Chromatography-Mass Spectroscopy
LDA lithium diisopropylamide
LiHMDS lithium bis(trimethylsilyl)amide
Me methyl
MeOH methanol
min minute(s)
MTBE methyl tert-butyl ether
N$_2$ nitrogen
NaHMDS sodium bis(trimethylsilyl)amide
Pd/C palladium on carbon
Ph phenyl
RT retention time sat saturated
TBTU O-(1H-benzotriazol-1-yl)-N,N,N',N'-tetramethyluronium tetrafluoroborate
TEA triethylamine
Tf$_2$O trifluoromethylsulfonic anhydride
TFA trifluoroacetic acid
THF tetrahydrofuran Intermediate S-1: (2R,3S)-3-(tert-Butylcarbamoyl)-6,6,6-trifluoro-2-(3,3,3-trifluoropropyl)hexanoic acid

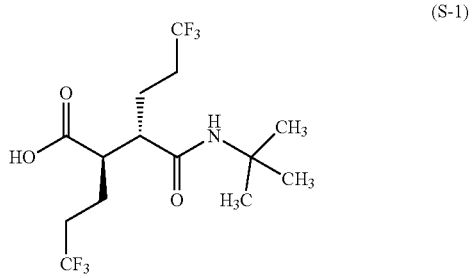 [SMILES: CC(C)(C)NC(=O)[C@@H](CCC(F)(F)F)[C@@H](CCC(F)(F)F)C(=O)O]

Intermediate S-1A: tert-Butyl 5,5,5-trifluoropentanoate

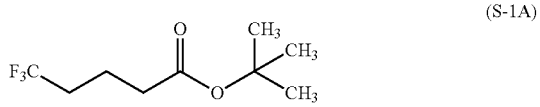

To a stirred solution of 5,5,5-trifluoropentanoic acid (5 g, 32.0 mmol) in THF (30 mL) and hexane (30 mL) at 0° C., was added tert-butyl 2,2,2-trichloroacetimidate (11.46 mL, 64.1 mmol). The mixture was stirred for 15 min at 0° C. Boron trifluoride etherate (0.406 mL, 3.20 mmol) was added and the reaction mixture was allowed to warm to room temperature overnight. To the clear reaction mixture was added solid NaHCO$_3$ (5 g) and stirred for 30 min. The mixture was filtered through MgSO$_4$ and washed with hexanes (200 mL). The solution was allowed to rest for 45 min, and the resulting solid material was removed by filtering on the same MgSO$_4$ filter again, washed with hexanes (100 mL) and concentrated under reduced pressure without heat. The volume was reduced to about 30 mL, filtered through a clean fritted funnel, washed with hexane (5 mL), and then concentrated under reduced pressure without heat. The resulting neat oil was filtered through a 0.45 μm nylon membrane filter disk to provide Intermediate S-1A (6.6 g, 98%) as a colorless oil: $^1$H NMR (400 MHz, CDCl$_3$) δ ppm 1.38 (s, 9H) 1.74-1.83 (m, 2H) 2.00-2.13 (m, 2H) 2.24 (t, J=7.28 Hz, 2H).

Intermediate S-1B: (4S)-4-(Propan-2-yl)-3-(5,5,5-trifluoropentanoyl)-1,3-oxazolidin-2-one

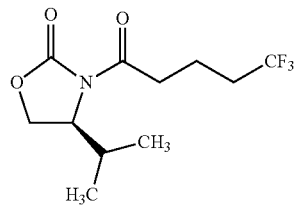

To a stirred solution of 5,5,5-trifluoropentanoic acid (5.04 g, 32.3 mmol) in DCM (50 mL) and DMF (3 drops) was added oxalyl chloride (3.4 mL, 38.8 mmol) dropwise over 5 min and the solution was stirred until all bubbling subsided. The reaction mixture was concentrated under reduced pressure to give pale yellow oil. To a separate flask charged with a solution of (4S)-4-(propan-2-yl)-1,3-oxazolidin-2-one (4.18 g, 32.4 mmol) in THF (100 mL) at –78° C. was added n-BuLi (2.5M in hexane, 13.0 mL, 32.5 mmol) dropwise via syringe over 5 min. After stirring for 10 min, the above acid chloride dissolved in THF (20 mL) was added via cannula over 15 min. The reaction mixture was warmed to 0° C., and was allowed to warm to room temperature as the bath warmed and stirred overnight. To the reaction mixture was added saturated NH$_4$Cl, and then extracted with EtOAc (2×). The combined organics were washed with brine, dried (Na$_2$SO$_4$), filtered and concentrated under reduced pressure. The crude material was purified by flash chromatography (Teledyne ISCO CombiFlash Rf, 5% to 60% solvent A/B=hexanes/EtOAc, REDISEP® SiO$_2$ 120 g). Concentration of appropriate fractions provided Intermediate S-1B (7.39 g, 86%) as a colorless oil: $^1$H NMR (400 MHz, CDCl$_3$) δ ppm 4.44 (1H, dt, J=8.31, 3.53 Hz), 4.30 (1H, t, J=8.69 Hz), 4.23 (1H, dd, J=9.06, 3.02 Hz), 2.98-3.08 (2H, m), 2.32-2.44 (1H, m, J=13.91, 7.02, 7.02, 4.03 Hz), 2.13-2.25 (2H, m), 1.88-2.00 (2H, m), 0.93 (3H, d, J=7.05 Hz), 0.88 (3H, d, J=6.80 Hz).

Intermediate S-1C: (2S,3R)-tert-Butyl 6,6,6-trifluoro-3-((S)-4-isopropyl-2-oxooxazolidine-3-carbonyl)-2-(3,3,3-trifluoropropyl)hexanoate, and Intermediate S-1D: (2R,3R)-tert-Butyl 6,6,6-trifluoro-3-((S)-4-isopropyl-2-oxooxazolidine-3-carbonyl)-2-(3,3,3-trifluoropropyl)hexanoate

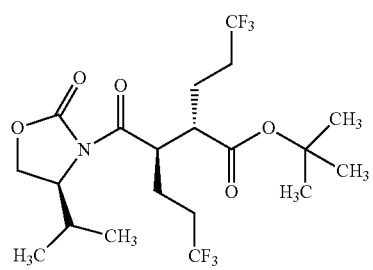

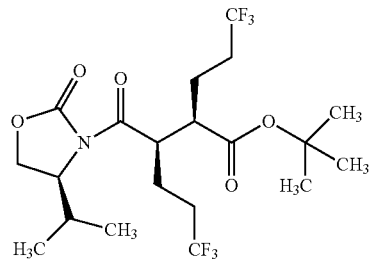

To a cold (–78° C.), stirred solution of diisopropylamine (5.3 mL, 37.2 mmol) in THF (59 mL) under nitrogen atmosphere was added n-BuLi (2.5M in hexane) (14.7 mL, 36.8 mmol), then warmed to 0° C. to give a 0.5M solution of LDA. A separate vessel was charged with Intermediate S-1B (2.45 g, 9.17 mmol), the material was azeotroped twice with benzene (the RotoVap air inlet was fitted with nitrogen inlet to completely exclude humidity) then toluene (15.3 mL) was added. This solution was added to a flask containing dry lithium chloride (1.96 g, 46.2 mmol). To the resultant mixture, cooled to –78° C., was added LDA solution (21.0 mL, 10.5 mmol) and stirred at –78° C. for 10 min, warmed to 0° C. for 10 min then recooled to –78° C. To a separate reaction vessel containing Intermediate S-1A (3.41 g, 16.07 mmol), also azeotroped twice with benzene, was added toluene (15.3 mL), cooled to –78° C. Next, LDA (37.0 mL, 18.5 mmol) was added and the resulting solution was stirred at –78° C. for 25 min. At this time the enolate derived from the ester was transferred via cannula into the solution of the oxazolidinone enolate, stirred at –78° C. for an additional 5 min. The septum was removed and solid powdered bis(2-ethylhexanoyloxy)copper (9.02 g, 25.8 mmol) was rapidly added to the reaction vessel and the septum replaced. The vessel was immediately removed from the cold bath and immersed into a warm water bath (40° C.) with rapid swirling with a concomitant color change from the initial turquoise to brown. The reaction mixture was stirred for 20 min, was poured into 5% aqueous NH$_4$OH (360 mL) and extracted with EtOAc (2×). The combined organics were washed with brine, dried (Na$_2$SO$_4$), filtered and concentrated under reduced pressure. The residue was purified by flash chromatography (Teledyne ISCO CombiFlash Rf, 0% to 60% solvent A/B=hexanes/EtOAc, REDISEP® SiO$_2$ 120 g). Concentration of appropriate fractions provided a mixture of Intermediates S-1C and S-1D (2.87 g, 66%) as pale yellow viscous oil. $^1$H NMR showed the product was a 1.6:1 mixture of diastereomers S-1C:S-1D as determined by the integration of the multiplets at 2.74 and 2.84 ppm: $^1$H NMR (400 MHz, CDCl$_3$) δ ppm 4.43-4.54 (2H, m), 4.23-4.35 (5H, m), 4.01 (1H, ddd, J=9.54, 6.27, 3.51 Hz), 2.84 (1H, ddd, J=9.41, 7.28, 3.64 Hz), 2.74 (1H, ddd, J=10.29, 6.27, 4.02 Hz), 2.37-2.48 (2H, m, J=10.38, 6.98, 6.98, 3.51, 3.51 Hz), 2.20-2.37 (3H, m), 1.92-2.20 (8H, m), 1.64-1.91 (5H, m), 1.47 (18H, s), 0.88-0.98 (12H, m).

Intermediate S-1: (2R,3S)-3-(tert-Butoxycarbonyl)-6,6,6-trifluoro-2-(3,3,3-trifluoropropyl)hexanoic acid, and Intermediate S-1E: (2R,3R)-3-(tert-Butoxycarbonyl)-6,6,6-trifluoro-2-(3,3,3-trifluoropropyl)hexanoic acid

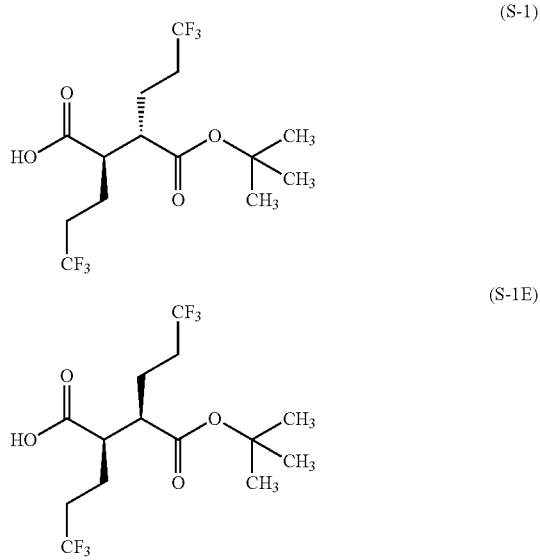

To a cool (0° C.), stirred solution of a mixture of Intermediates S-1C and S-1D (4.54 g, 9.51 mmol) in THF (140 mL) and water (42 mL) was sequentially added hydrogen peroxide (30% in water, 10.3 g, 91 mmol) and LiOH (685.3 mg, 28.6 mmol) and the mixture was stirred for 1 hr. At this time the reaction vessel was removed from the cold bath and then stirred for 1.5 hr. The reaction was judged complete by HPLC. To the reaction mixture was added saturated NaHCO$_3$ (45 mL) and saturated Na$_2$SO$_3$ (15 mL), and then partially concentrated under reduced pressure. The resulting crude solution was extracted with DCM (3×). The aqueous phase was acidified to pH-1-2 with 1N HCl, extracted with DCM (3×) and EtOAc (1×). The combined organics were washed with brine, dried (Na$_2$SO$_4$), filtered and concentrated under reduced pressure to provide a mixture of Intermediate S-1 and Intermediate S-1E (3.00 g, 86%) as colorless oil: $^1$H NMR (400 MHz, CDCl$_3$) δ ppm 2.76-2.84 (1H, m, diastereomer 2), 2.64-2.76 (3H, m), 2.04-2.35 (8H, m), 1.88-2.00 (4H, m), 1.71-1.83 (4H, m), 1.48 (9H, s, diastereomer 1), 1.46 (9H, s, diastereomer 2); $^1$H NMR showed a 1.7:1 mixture of S-1:S-1E by integration of the peaks for the t-butyl groups.

Intermediate S-1: (2R,3S)-3-(tert-Butoxycarbonyl)-6,6,6-trifluoro-2-(3,3,3-trifluoropropyl)hexanoic acid, and Intermediate S-1E: (2R,3R)-3-(tert-Butoxycarbonyl)-6,6,6-trifluoro-2-(3,3,3-trifluoropropyl)hexanoic acid, an enriched mixture To a cold (−78° C.), stirred solution of diisopropylamine (1.7 mL, 11.93 mmol) in THF (19 mL) under nitrogen atmosphere was added n-BuLi (2.5M in hexanes, 4.8 mL, 12.00 mmol). The mixture was stirred for 5 min and then warmed to 0° C. In a separate vessel, to a cold (−78° C.) stirred solution of the mixture of Intermediate S-1 and Intermediate S-1E (1.99 g, 5.43 mmol) in THF (18 mL) was added the LDA solution prepared above via cannula slowly over 25 min. The mixture was stirred for 15 min, then warmed to room temperature (placed in a 24° C. water bath) for 15 min, and then again cooled to −78° C. for 15 min. To the reaction mixture was added Et$_2$AlCl (1M in hexane) (11.4 mL, 11.40 mmol) via syringe, stirred for 10 min, warmed to room temperature for 15 min and then cooled back to −78° C. for 15 min. Methanol (25 mL) was rapidly added, swirled vigorously while warming to room temperature, then concentrated to ~¼ original volume. The mixture was dissolved in EtOAc and washed with 1N HCl (50 mL) and ice (75 g). The aqueous phase was separated, extracted with EtOAc (2×). The combined organics were washed with a mixture of KF (2.85 g in 75 mL water) and 1N HCl (13 mL) [resulting solution pH 3-4], then with brine, dried (Na$_2$SO$_4$), filtered and concentrated under reduced pressure to give a 9:1 (S-1:S-1E) enriched diastereomeric mixture (as determined by $^1$H NMR) of Intermediate S-1 and Intermediate S-1E (2.13 g, >99%) as a pale yellow viscous oil: $^1$H NMR (400 MHz, CDCl$_3$) δ ppm 2.64-2.76 (2H, m), 2.04-2.35 (4H, m), 1.88-2.00 (2H, m), 1.71-1.83 (2H, m), 1.48 (9H, s).

Alternate Procedure to Make Intermediate S-1

Intermediate S-1F: 3,3,3-Trifluoropropyl trifluoromethanesulfonate

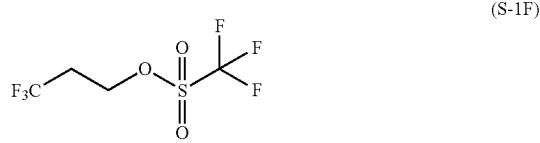 [SMILES: O=S(=O)(OCCC(F)(F)F)C(F)(F)F]

To a cold (−25° C.), stirred solution of 2,6-lutidine (18.38 mL, 158 mmol) in CH$_2$Cl$_2$ (120 mL) was added Tf$_2$O (24.88 mL, 147 mmol) over 3 min, and stirred for 5 min. To the reaction mixture was added 3,3,3-trifluoropropan-1-ol (12 g, 105 mmol) over an interval of 3 min. After 2 hr, the reaction mixture was warmed to room temperature and stirred for 1 hr. The reaction mixture was concentrated to half volume, then purified by loading directly on silica gel column (330 g Isco) and eluted with CH$_2$Cl$_2$. Obtained Intermediate S-1F (13.74 g, 53%) as a colorless oil. $^1$H NMR (400 MHz, CDCl$_3$) δ ppm 4.71 (2H, t, J=6.15 Hz), 2.49-2.86 (2H, m).

Intermediate S-1G: (4S)-4-Benzyl-3-(5,5,5-trifluoropentanoyl)-1,3-oxazolidin-2-one

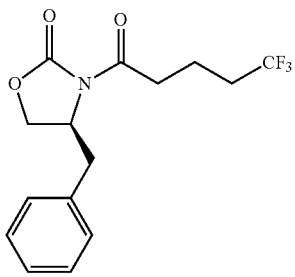

(S-1G)

Intermediate S-1G was prepared from 5,5,5-trifluoropentanoic acid (3.35 g, 21.46 mmol) and (4S)-4-benzyl-1,3-oxazolidin-2-one (3.80 g, 21.46 mmol) by the general method shown for Intermediate S-1B. Intermediate S-1G (5.67 g, 84%) was obtained as a colorless viscous oil: $^1$H NMR (400 MHz, CDCl$_3$) δ ppm 7.32-7.39 (2H, m), 7.30 (1H, d, J=7.05 Hz), 7.18-7.25 (2H, m), 4.64-4.74 (1H, m), 4.17-4.27 (2H, m), 3.31 (1H, dd, J=13.35, 3.27 Hz), 3.00-3.11 (2H, m), 2.79 (1H, dd, J=13.35, 9.57 Hz), 2.16-2.28 (2H, m), 1.93-2.04 (2H, m).

Intermediate S-1H: tert-Butyl (3R)-3-(((4S)-4-benzyl-2-oxo-1,3-oxazolidin-3-yl)carbonyl)-6,6,6-trifluorohexanoate

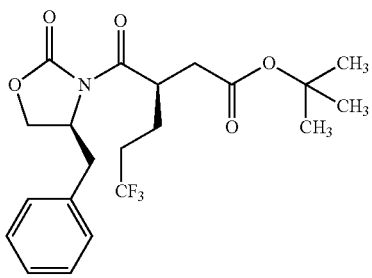

(S-1H)

To a cold (−78° C.), stirred solution of Intermediate S-1G (3.03 g, 9.61 mmol) in THF (20 mL) was added NaHMDS (1.0M in THF, 10.6 mL, 10.60 mmol) under nitrogen atmosphere. After 2 hours, tert-butyl 2-bromoacetate (5.62 g, 28.8 mmol) was added neat via syringe at −78° C. and stirring was maintained at the same temperature. After 6 hours, the reaction mixture was warmed to room temperature. The reaction mixture was partitioned between saturated NH$_4$Cl and EtOAc. The organic phase was separated, and the aqueous was extracted with EtOAc (3×). The combined organics were washed with brine, dried (Na$_2$SO$_4$), filtered and concentrated under reduced pressure. The residue was purified by flash chromatography (Teledyne ISCO CombiFlash Rf, 5% to 100% solvent A/B=hexanes/EtOAc, REDISEP® SiO$_2$ 120 g). Concentration of appropriate fractions provided Intermediate S-1H (2.79 g, 67.6%) as a colorless viscous oil: $^1$H NMR (400 MHz, CDCl$_3$) δ ppm 7.34 (2H, d, J=7.30 Hz), 7.24-7.32 (3H, m), 4.62-4.75 (1H, m, J=10.17, 6.89, 3.43, 3.43 Hz), 4.15-4.25 (3H, m), 3.35 (1H, dd, J=13.60, 3.27 Hz), 2.84 (1H, dd, J=16.62, 9.57 Hz), 2.75 (1H, dd, J=13.35, 10.07 Hz), 2.47 (1H, dd, J=16.62, 4.78 Hz), 2.11-2.23 (2H, m), 1.90-2.02 (1H, m), 1.72-1.84 (1H, m), 1.44 (9H, s).

Intermediate S-1I: (2R)-2-(2-tert-Butoxy-2-oxoethyl)-5,5,5-trifluoropentanoic acid

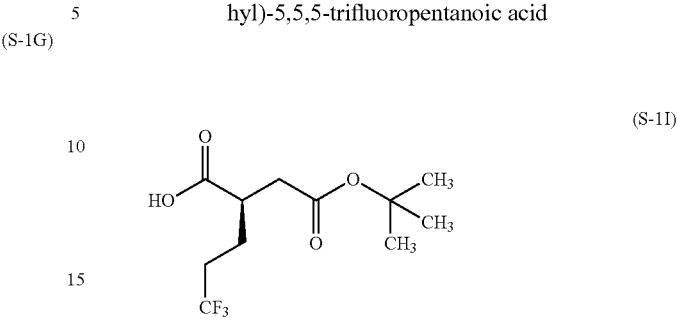

(S-1I)

Intermediate S-1I was prepared from Intermediate S-1H (2.79 g, 6.50 mmol) by the general methods shown for the mixture of Intermediate S-1 and Intermediate S-1E. Intermediate S-1I (1.45 g, 83%) was obtained as a colorless oil: $^1$H NMR (400 MHz, CDCl$_3$) δ ppm 2.83-2.95 (1H, m), 2.62-2.74 (1H, m), 2.45 (1H, dd, J=16.62, 5.79 Hz), 2.15-2.27 (2H, m), 1.88-2.00 (1H, m), 1.75-1.88 (1H, m), 1.45 (9H, s).

Intermediate S-1: (2R,3S)-3-(tert-Butoxycarbonyl)-6,6,6-trifluoro-2-(3,3,3-trifluoropropyl) hexanoic acid, and

Intermediate S-1E: (2R,3R)-3-(tert-Butoxycarbonyl)-6,6,6-trifluoro-2-(3,3,3-trifluoropropyl)hexanoic acid

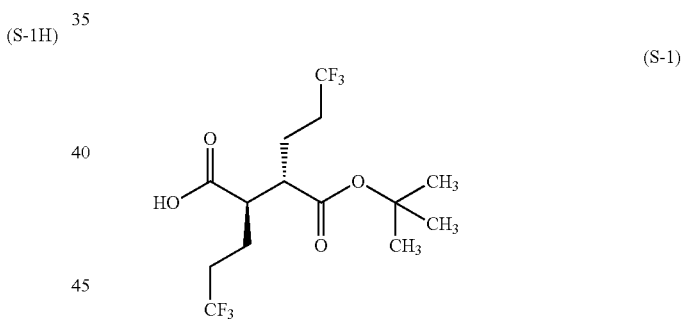

(S-1)

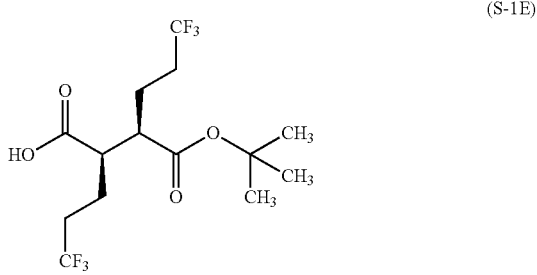

(S-1E)

In a 500 mL round-bottomed flask was Intermediate S-1I (5 g, 18.50 mmol) in THF (60 mL) to give a colorless solution then cooled to −78° C. To the cold stirring solution was added LDA (22.2 mL, 44.4 mmol, 2.0M) slowly to the reaction over 7 min. After 2 h, Intermediate S-1F (6.38 g, 25.9 mmol) was added to the reaction mixture over 3 min and stirred at −78° C. After 60 min, the reaction mixture was placed in a −25° C. bath (ice/MeOH/dry ice), stirred for an additional 60 min at which time saturated aqueous NH$_4$Cl was added. The separated aqueous phase was acidified with aqueous 1N HCl to pH 3, then extracted with Et₂O, washed the combined organic layers with brine (×2), dried over MgSO₄, filtered and concentrated to provide a 1:4 (S-1:S-1E) mixture (as determined by ¹H NMR) of Intermediate S-1 and Intermediate S-1E (6.00 g, 89%) as a pale yellow solid: ¹H NMR (500 MHz, CDCl₃) δ ppm 2.81 (1H, ddd, J=10.17, 6.32, 3.85 Hz), 2.63-2.76 (1H, m), 2.02-2.33 (4H, m), 1.86-1.99 (2H, m), 1.68-1.85 (2H, m), 1.47 (9H, s).

Intermediate S-1: (2R,3S)-3-(tert-Butoxycarbonyl)-6,6,6-trifluoro-2-(3,3,3-trifluoropropyl)hexanoic acid, and Intermediate S-1E: (2R,3R)-3-(tert-Butoxycarbonyl)-6,6,6-trifluoro-2-(3,3,3-trifluoropropyl)hexanoic acid

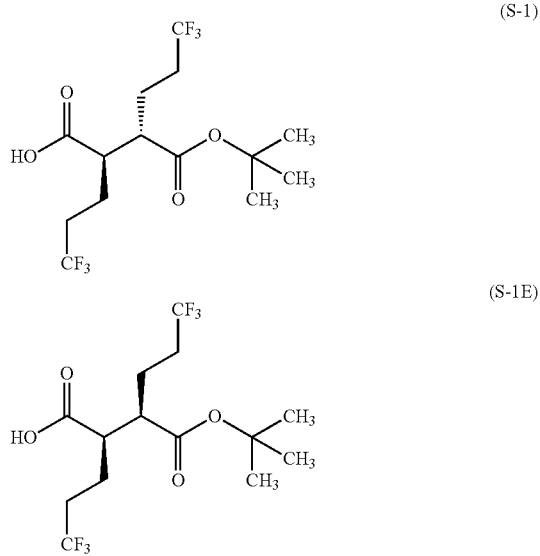

To a cold (−78° C.), stirred solution of a mixture of Intermediate S-1 and Intermediate S-1E (5.97 g, 16.30 mmol) in THF (91 mL) was added LDA (19 mL, 38.0 mmol, 2.0M in THF/hexane/ethyl benzene) dropwise via syringe over 10 min (internal temperature never exceeded −65° C., J-KEM® probe in reaction solution), stirred for 15 min, warmed to room temperature (24° C. water bath), stirred for 15 min, cooled to −78° C. for 15 min. To the reaction mixture was added Et₂AlCl (41 mL, 41.0 mmol, 1M in hexane) via syringe (internal temperature never exceeded −55° C.), stirred for 10 min, warmed to room temperature (24° C. bath) for 15 min then back to −78° C. for 15 min. Meanwhile, a 1000 mL RB flask was charged with MeOH (145 mL) and precooled to −78° C. With vigorous stirring the reaction mixture was transferred via cannula over 5 min to the MeOH. The flask was removed from the bath, ice was added followed by slow addition of 1N HCl (147 mL, 147 mmol). Gas evolution was observed as the HCl was added. The reaction mixture was allowed to warm to room temperature during which the gas evolution subsided. The reaction mixture was diluted with EtOAc (750 mL), saturated with NaCl, the organic phase was separated, washed with a solution of potassium fluoride (8.52 g, 147 mmol) and 1N HCl (41 mL, 41.0 mmol) in water (291 mL), brine (100 mL), dried (Na₂SO₄) filtered and concentrated then dried under vacuum. ¹H NMR showed product was 9:1 mixture of Intermediate S-1 and Intermediate S-1E. Obtained the enriched mixture of Intermediate S-1 and Intermediate S-1E (6.12 g, >99% yield) as an amber oil: ¹H NMR (400 MHz, CDCl₃) δ ppm 2.64-2.76 (2H, m), 2.04-2.35 (4H, m), 1.88-2.00 (2H, m), 1.71-1.83 (2H, m), 1.48 (9H, s).

Procedure to Make Diastereomerically Pure Intermediate S-1

Intermediate S-1J: (2R,3S)-1-Benzyl 4-tert-butyl 2,3-bis(3,3,3-trifluoropropyl)succinate

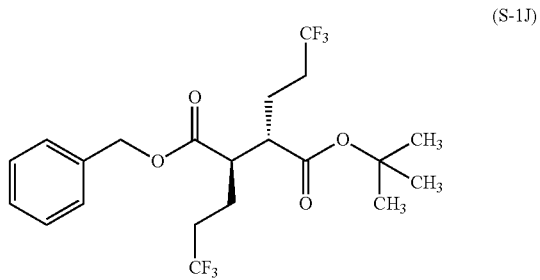 [SMILES: CC(C)(C)OC(=O)[C@@H](CCC(F)(F)F)[C@@H](CCC(F)(F)F)C(=O)OCc1ccccc1]

To a stirred solution of a 9:1 enriched mixture of Intermediate S-1 and Intermediate S-1E (5.98 g, 16.33 mmol) in DMF (63 ml) was added potassium carbonate (4.06 g, 29.4 mmol) and benzyl bromide (2.9 ml, 24.38 mmol), then stirred overnight. The reaction mixture was diluted with EtOAc (1000 mL), washed with 10% LiCl (3×200 mL), brine (200 mL), dried (Na₂SO₄), filtered and concentrated then dried under vacuum. The residue was purified by SiO₂ chromatography using a toluene:hexane gradient. Obtained diastereomerically pure Intermediate S-1J (4.81 g, 65%) as a colorless solid: ¹H NMR (400 MHz, chloroform-d) δ 7.32-7.43 (m, 5H), 5.19 (d, J=12.10 Hz, 1H), 5.15 (d, J=12.10 Hz, 1H), 2.71 (dt, J=3.52, 9.20 Hz, 1H), 2.61 (dt, J=3.63, 9.63 Hz, 1H), 1.96-2.21 (m, 4H), 1.69-1.96 (m, 3H), 1.56-1.67 (m, 1H), 1.45 (s, 9H).

Intermediate S-1

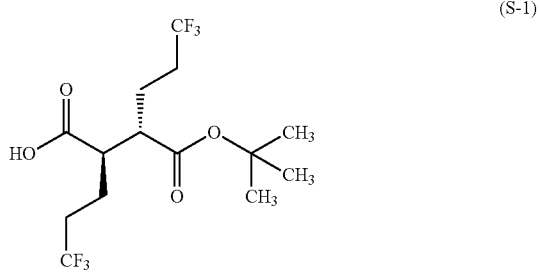 [SMILES: CC(C)(C)OC(=O)[C@@H](CCC(F)(F)F)[C@@H](CCC(F)(F)F)C(=O)O]

To a solution of Intermediate S-1J (4.81 g, 10.54 mmol) in MeOH (100 mL) was added 10% palladium on carbon (wet, Degussa type, 568.0 mg, 0.534 mmol) in a H₂-pressure flask. The vessel was purged with N₂ (4×) then with H₂ (2×), then pressurized to 50 psi and shaken overnight. The reaction mixture was depressurized and purged, the mixture was filtered through CELITE®, washed with MeOH then concentrated and dried under vacuum. Obtained Intermediate S-1

(3.81 g, 99%) as a colorless solid: $^1$H NMR (400 MHz, chloroform-d) δ 2.62-2.79 (m, 2H), 2.02-2.40 (m, 4H), 1.87-2.00 (m, 2H), 1.67-1.84 (m, 2H), 1.48 (s, 9H).

An Alternate Method to Purify Intermediate S-1

Intermediate S-1: (2R,3S)-3-(tert-Butoxycarbonyl)-6,6,6-trifluoro-2-(3,3,3-trifluoropropyl)hexanoic acid

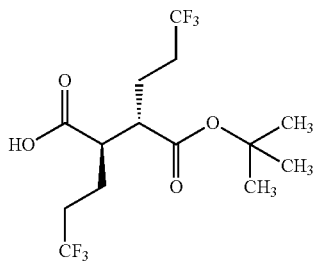

(S-1)

Intermediate S-1 as a mixture with Intermediate S-1E was prepared in a similar manner as above from Intermediate S-1I to afford a 1:2.2 mixture of Intermediate S-1 and Intermediate S-1E (8.60 g, 23.48 mmol), which was enriched using LDA (2.0 M solution in THF, ethyl benzene and heptane, 28.2 mL, 56.4 mmol) and diethyl aluminum chloride (1.0 M solution in hexane, 59 mL, 59.0 mmol) in THF (91 mL). After workup as explained above, the resulting residue was found to be a 13.2:1 (by $^1$H NMR) mixture of Intermediate S-1 and Intermediate S-1E, which was treated as follows: The crude material was dissolved in MTBE (43 mL). Hexanes (26 mL) were slowly charged to the reaction mixture while maintaining a temperature below 30° C. The reaction mixture was stirred for 10 min. Next, tert-butylamine (2.7 mL, 1.1 eq) was charged slowly over a period of 20 minutes while maintaining a temperature below 30° C. This addition was observed to be exothermic. The reaction mixture was stirred for 2 hrs below 30° C. and filtered. The solid material was washed with 5:3 MTBE:hexane (80 mL), the filtrate was concentrated and set aside. The filtered solid was dissolved in dichloromethane (300 mL), washed with 1N HCl (100 mL), the organic layer was washed with brine (100 mL×2), then was concentrated under reduced pressure below 45° C. Obtained Intermediate S-1 (5.46 g, 64%).

Intermediate S-2: (R)-2-((S)-1-tert-Butoxy-3-cyclopropyl-1-oxopropan-2-yl)-5,5,5-trifluoropentanoic acid

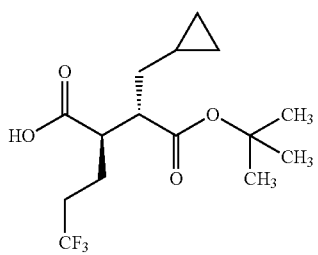

(S-2)

Intermediate S-2A: tert-Butyl 3-cyclopropylpropanoate

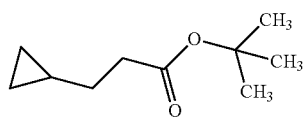

(S-2A)

To a cool (0° C., precooled for at least 15 min), stirred solution of 3-cyclopropylpropanoic acid (5 g, 43.8 mmol) in hexane (30.0 mL) and THF (30 mL) under N$_2$ was added tert-butyl 2,2,2-trichloroacetimidate (15.7 mL, 88 mmol) portionwise over 5 min. The reaction mixture was stirred for 15 min. Boron trifluoride ether complex (0.555 mL, 4.38 mmol) was added and the reaction mixture was allowed to warm to room temperature as the bath warmed overnight. To the clear reaction mixture was added NaHCO$_3$ (5 g) and stirred for 60 min. The suspension was filtered through MgSO$_4$ and washed with 300 mL hexane. The filtrate was allowed to sit, then the solid was filtered through the same MgSO$_4$ filter, washed with hexane (100 mL). The filtrate was concentrated in vacuo with the water bath not turned on. The residue was purified by silica gel chromatography (hexanes/EtOAc) to provide Intermediate S-1B (6.05 g, 81%) as clear oil: $^1$H NMR (400 MHz, CDCl$_3$) δ 2.29 (2H, t, J=7.48 Hz), 1.35-1.54 (11H, m), 0.60-0.75 (1H, m), 0.29-0.46 (2H, m), −0.06-0.10 (2H, m).

Intermediate S-2B: (2S,3R)-tert-Butyl 2-(cyclopropylmethyl)-6,6,6-trifluoro-3-((S)-4-isopropyl-2-oxooxazolidine-3-carbonyl)hexanoate, and Intermediate S-2C: (2R,3R)-tert-Butyl 2-(cyclopropylmethyl)-6,6,6-trifluoro-3-((S)-4-isopropyl-2-oxooxazolidine-3-carbonyl)hexanoate

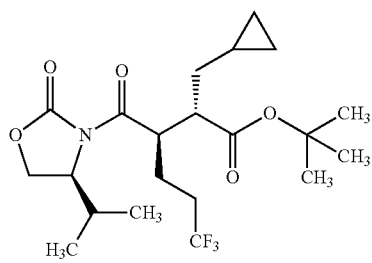

(S-2B)

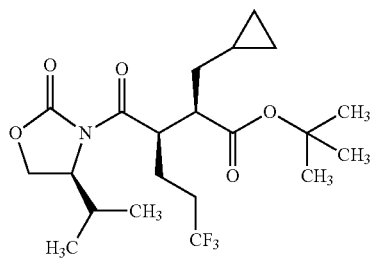

(S-2C)

Diisopropylamine (6.64 ml, 46.6 mmol) was dissolved in 71.7 mL of THF and cooled to −78° C., then n-BuLi (18.0 mL, 44.9 mmol, 2.5M in hexane) was added dropwise over a period of 5 minutes. After 5 minutes, the resulting 0.5 M LDA solution was kept at 0° C. In a separate flask, lithium chloride (2.62 g, 61.7 mmol) was dried under high vacuum with heating and cooled under nitrogen. Intermediate S-1B (3.0 g, 11.23 mmol), azeotroped once with toluene, was transferred with 15.0 mL toluene to the flask containing LiCl, and cooled to −78° C. To this stirring suspension was added LDA (25.83 mL, 12.91 mmol, 1.15 equiv., 0.5M LDA) dropwise via syringe over 5 min. The reaction mixture was stirred at −78° C. for 15 minutes, then at 0° C. for 10 minutes and cooled to −78° C.

In a separate flask, Intermediate S-2A (3.44 g, 20.21 mmol) was dissolved in 15.0 mL toluene under $N_2$ and cooled to −78° C. To this solution was added LDA (46.48 mL, 23.24 mmol, 1.15 equiv., 0.5M LDA) dropwise and stirred at −78° C. for 30 minutes, at which time this solution was added via cannula (fast negative pressure, all added within 30 seconds) to the LiCl/oxazolidone solution at −78° C. After 1 minute following transfer, solid bis(2-ethylhexanoyloxy)copper (10.80 g, 30.9 mmol) was added at −78° C., and the flask was transferred to 40° C. water bath and swirled vigorously for 15 minutes, and quenched over 5% $NH_4OH$ solution (20 mL saturated $NH_4OH$ and 100 mL water), and extracted with ethyl acetate (2×100 mL). The pooled organic phases were washed with brine, dried ($Na_2SO_4$), filtered, concentrated and purified by silica gel chromatography (hexanes/EtOAc) to afford a mixture of Preparations S-2B and S-2C (1.58 g, 32% yield) as an oil: $^1$H NMR showed this material to be a 1.5:1 mixture of S-2B:S-2C, by integration of the t-Bu peaks: $^1$H NMR of diastereoisomer mixture (400 MHz, $CDCl_3$) δ 4.53-4.41 (m, 2H), 4.39-4.19 (m, 5H), 4.10-4.01 (m, 1H), 2.89-2.77 (m, 2H), 2.47-2.26 (m, 2H), 2.16-1.72 (m, 8H), 1.47 (s, 9H, t-Bu of S-2B, integrates for relative intensity of 1.5), 1.46 (s, 9H, t-Bu of S-2C, integrates for relative intensity of 1), 0.98-0.86 (m, 16H), 0.78-0.64 (m, 2H), 0.56-0.37 (m, 4H), 0.14-0.01 (m, 4H).

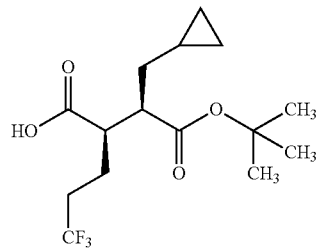
(S-2D)

To a cool (0° C.), stirred solution of a mixture of Preparations S-2B:S-2C (3.4 g, 7.81 mmol) in THF (60 mL) and water (20 mL) was added 30% $H_2O_2$ (4.82 mL, 79 mmol) followed by LiOH (0.567 g, 23.66 mmol). The reaction mixture was allowed to gradually warm up to room temperature and stirred at room temperature for 3 h. To the reaction mixture was added saturated $Na_2SO_3$ (20 mL) and saturated $NaHCO_3$ (40 mL), and then stirred for 5 min. The reaction mixture was partially concentrated and extracted with DCM (80 mL). The aqueous phase was acidified to pH~2, saturated with NaCl, extracted with EtOAc (2×). The combined extracts were dried ($MgSO_4$), filtered and concentrated to provide a mixture of Intermediate S-2 and Intermediate S-2D (2.01 g, 79%): $^1$H NMR showed this material to be a 1.4:1 mixture of S-2:S-2D, by integration of the t-Bu peaks: $^1$H NMR of mixture of diastereomers (400 MHz, $CDCl_3$) δ 2.82-2.59 (m, 4H), 2.31-2.03 (m, 4H), 1.95-1.52 (m, 7H), 1.44 (s, 9H, t-Bu of S-1, integrates for relative intensity of 1.4), 1.42 (s, 9H, t-Bu of S-2E, integrates for relative intensity of 1), 0.93 (d, J=6.6 Hz, 1H), 0.88 (d, J=6.8 Hz, 1H), 0.74-0.57 (m, 2H), 0.43 (t, J=6.8 Hz, 3H), 0.11-0.04 (m, 3H).

Intermediate S-2: (R)-2-((S)-1-tert-Butoxy-3-cyclopropyl-1-oxopropan-2-yl)-5,5,5-trifluoropentanoic acid, and Intermediate S-2D: (R)-2-((R)-1-tert-Butoxy-3-cyclopropyl-1-oxopropan-2-yl)-5,5,5-trifluoropentanoic acid, an enriched mixture Intermediate S-2: (R)-2-((S)-1-tert-Butoxy-3-cyclopropyl-1-oxopropan-2-yl)-5,5,5-trifluoropentanoic acid, and Intermediate S-2D: (R)-2-((R)-1-tert-Butoxy-3-cyclopropyl-1-oxopropan-2-yl)-5,5,5-trifluoropentanoic acid

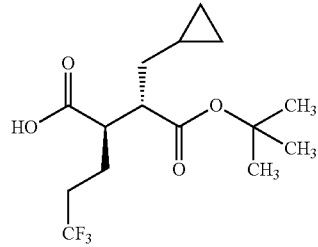
(S-2)

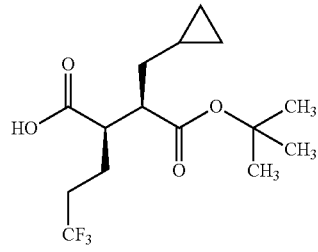
(S-2D)

To a cold (−78° C.), stirred solution of a 1.4:1 mixture of Intermediate S-2 and Intermediate S-2D (2.00 g, 6.17 mmol) in THF (30 mL) under N₂ was added LDA (7.54 mL, 13.57 mmol, 1.8M) via syringe over 5 min, stirred for 15 min, warmed to room temperature (24° C. water bath), stirred for 15 min, and cooled to −78° C. for 15 min. To the reaction mixture was added diethylaluminum chloride (12.95 mL, 12.95 mmol, 1M in hexane) via syringe, stirred for 10 min, warmed to room temperature (24° C. bath) for 15 min then back to −78° C. for 25 min. MeOH (38.9 mL, 962 mmol) was rapidly added. The reaction mixture was removed from bath and then ice and 1N HCl (55.5 mL, 55.5 mmol) were added slowly. Once gas evolution subsided, the mixture was extracted with EtOAc (2×), the combined organics washed with a solution of potassium fluoride (3.26 g, 56.2 mmol) in water (106 mL, 5895 mmol) and 1N HCl (15.72 mL, 15.72 mmol), brine, and then dried (Na₂SO₄). The mixture was subsequently filtered and concentrated to afford a~2:1 (S-2: S-2D, as determined by integration of the t-Bu peaks in the ¹H NMR) enriched mixture of Intermediate S-2 and Intermediate S-2D (1.79 g, 90%): ¹H NMR of mixture of diastereomers (400 MHz, CDCl₃) δ 2.87-2.57 (m, 2H), 2.36-2.06 (m, 2H), 1.97-1.81 (m, 2H), 1.81-1.70 (m, 1H), 1.70-1.56 (m, 1H), 1.47 (s, 9H, t-Bu of S-2, integrates for relative intensity of 2.0), 1.45 (s, 9H, t-Bu of S-2D, integrates for relative intensity of 1), 0.99-0.87 (m, 1H), 0.77-0.61 (m, 1H), 0.54-0.38 (m, 2H), 0.16-0.01 (m, 2H).

Intermediate S-2E: (2R,3S)-1-Benzyl 4-tert-butyl 3-(cyclopropylmethyl)-2-(3,3,3-trifluoropropyl)succinate, and Intermediate S-2F: (2R,3R)-1-Benzyl 4-tert-butyl 3-(cyclopropylmethyl)-2-(3,3,3-trifluoropropyl)succinate

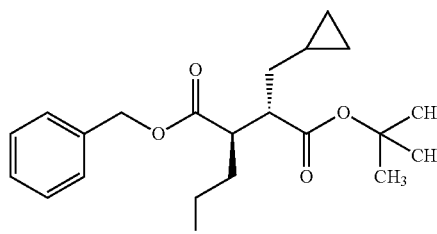

(S-2E)

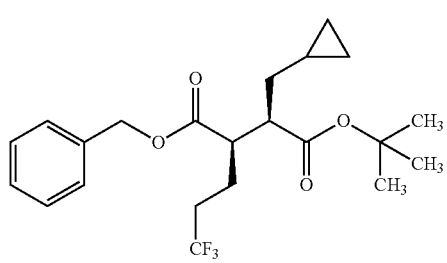

(S-2F)

To a stirred solution of a 2.15:1 mixture of Intermediate S-2 and Intermediate S-2D (2.22 g, 6.84 mmol) and benzyl bromide (0.98 ml, 8.24 mmol) in DMF (25 ml) was added potassium carbonate (1.41 g, 10.20 mmol). The reaction mixture was then stirred for 5.5 h. The reaction mixture was diluted with EtOAc (300 mL), washed with 10% LiCl (3×100 mL), sat NaCl, then dried (Na₂SO₄), filtered and concentrated. The residue was purified by silica gel chromatography (hexane: toluene) to give Intermediate S-2E (1.5 g, 53%) and Intermediate S-2F (0.778 g, 27%): Intermediate S-2E: ¹H NMR (400 MHz, CDCl₃) δ 7.43-7.31 (m, 29H), 5.17 (d, J=11.9 Hz, 6H), 5.13 (d, J=11.9 Hz, 6H), 2.75-2.64 (m, 11H), 2.19-1.94 (m, 12H), 1.93-1.81 (m, 6H), 1.79-1.69 (m, 6H), 1.63-1.56 (m, 4H), 1.46 (s, 47H), 1.14 (ddd, J=13.8, 7.2, 3.5 Hz, 6H), 0.68-0.55 (m, 6H), 0.45-0.37 (m, 11H), −0.02-0.11 (m, 6H). Intermediate S-2F: ¹H NMR (400 MHz, CDCl₃) δ 7.40-7.32 (m, 5H), 5.16 (d, J=12.3 Hz, 1H), 5.13 (d, J=12.1 Hz, 1H), 2.88-2.79 (m, 1H), 2.74 (ddd, J=8.8, 7.3, 4.4 Hz, 1H), 2.18-1.93 (m, 2H), 1.90-1.79 (m, 2H), 1.70-1.59 (m, 1H), 1.44 (s, 9H), 1.31 (ddd, J=14.1, 7.3, 4.5 Hz, 1H), 0.73-0.61 (m, 1H), 0.49-0.38 (m, 2H), 0.10-0.03 (m, 1H), −0.01-0.07 (m, 1H).

Intermediate S-2

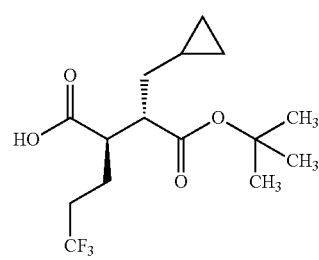

(S-2)

Intermediate S-2E (2.80 g, 6.76 mmol) was dissolved in ethyl acetate (26.0 mL) and methanol (26.0 mL). Palladium on carbon (10% wet Degussa, 0.539 g, 0.507 mmol) was added, then the atmosphere was exchanged for H₂ three times. The reaction mixture was stirred about 2 h, then filtered with MeOH washes. The filtrate was concentrated to give Intermediate S-2 (2.19 g, 100% yield): ¹H NMR (400 MHz, CDCl₃) δ 2.79-2.67 (m, 2H), 2.36-2.21 (m, 1H), 2.18-2.03 (m, 1H), 1.94 (dtd, J=14.6, 9.8, 4.8 Hz, 1H), 1.78 (ddd, J=11.1, 5.3, 3.0 Hz, 1H), 1.63 (ddd, J=13.9, 9.2, 7.0 Hz, 1H), 1.49 (s, 9H), 1.35 (ddd, J=13.8, 7.0, 3.9 Hz, 1H), 0.77-0.63 (m, 1H), 0.48 (dq, J=8.1, 1.7 Hz, 2H), 0.15-0.02 (m, 2H).

An Alternate Method to Prepare Intermediate S-2E, and Hence Intermediate S-2

Intermediate S-2G: (2R,3S)-3-(tert-Butoxycarbonyl)-2-(3,3,3-trifluoropropyl)hex-5-enoic acid, and Intermediate S-2H: (2R,3R)-3-(tert-Butoxycarbonyl)-2-(3,3,3-trifluoropropyl)hex-5-enoic acid

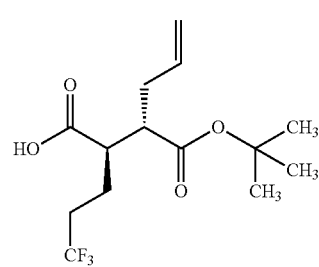

(S-2G)

-continued (S-2H)

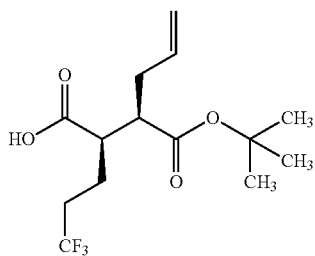

A flask was charged with THF (150 ml), cooled to −20° C., and then with stirring n-butyllithium (53.9 ml, 2.5 M in hexane, 135 mmol) was added, followed by diisopropylamine (19.4 ml, 137 mmol) over 55 min. The internal temperature was maintained at less than −8.5° C. After the addition was complete, the reaction mixture was stirred at 0° C. for 45 min, and then cooled to −78° C. To this was added a solution of Intermediate S-1I (14.56 g, 53.9 mmol) in THF (15.0 ml) over 20 min, while maintaining the internal temperature at less than −72° C. After the addition was complete, the mixture was stirred at −78° C. for 100 min. To this was added allylbromide (6.38 ml, 75 mmol) over 10 min. The reaction mixture was stirred, allowed to slowly warm to room temperature as the bath warmed, and then stirred overnight. To the solution was added ice, quenched with 1N HCl (215 mL) to pH about 1, saturated with NaCl. The layers were separated. The aqueous layer was extracted with EtOAc (1×250 mL, 1×150 mL). The combined organic phases were washed with brine (1×300 mL), dried (MgSO$_4$), filtered, and evaporated. The residue was treated with benzene (50 mL) and evaporated twice, dried in vacuo to give a mixture of Preparations S-2G and S-2H (16.8 g, 100%): $^1$H NMR indicated a ratio 1:2 for S-2G:S-2H: $^1$H NMR of diastereoisomer mixture (400 MHz, CDCl$_3$) δ 5.81-5.66 (m, 1H), 5.17-5.04 (m, 2H), 2.81-2.62 (m, 2H), 2.45-2.38 (m, 2H), 2.33-2.03 (m, 3H), 1.96-1.83 (m, 2H), 1.45 (s, 9H, t-Bu of S-2G, integrates for relative intensity of 1), 1.44 (s, 9H, t-Bu of S-2H, integrates for relative intensity of 2).

Intermediate S-2G: (2R,3S)-3-(tert-Butoxycarbonyl)-2-(3,3,3-trifluoropropyl)hex-5-enoic acid, and Intermediate S-2H: (2R,3R)-3-(tert-Butoxycarbonyl)-2-(3,3,3-trifluoropropyl) hex-5-enoic acid, an enriched mixture (S-2G)

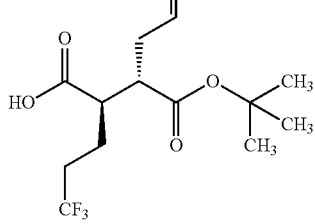

-continued (S-2H)

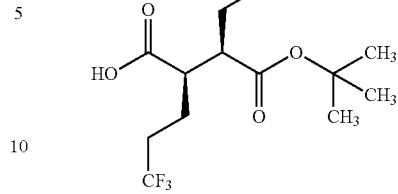

To a cold (−78° C.) stirred solution of a mixture of Preparations S-2G and S-2H (10 g, 32.2 mmol) in THF (150 mL) was slowly added LDA (39.4 mL, 70.9 mmol, 1.8M in heptane/THF/ethylbenzene). After stirring for 15 min, the reaction mixture was placed in a room temperature water bath. After 15 min, the reaction mixture was placed back in a −78° C. bath, stirred for 15 min, and then diethylaluminum chloride (81 mL, 81 mmol, 1M in hexane) was added via addition funnel. The reaction mixture was stirred at −78° C. After 10 min the reaction mixture was placed in a room temperature water bath for 15 min and then cooled back to −78° C. bath for 15 min. Meanwhile, a separate flask was charged MeOH (300 mL) and cooled to −78° C. The reaction mixture was then transferred to the cold and rapidly stirring MeOH via cannula by nitrogen pressure. After the transfer was complete, ice (86 g) was added to the reaction mixture followed by slow addition of 1N HCl (300 mL). The reaction mixture was stirred until all gas evolution subsided. EtOAc (400 mL) was added, the phases separated, and the aqueous phase was extracted with EtOAc (300 mL). The combined EtOAc layers were washed with a mixture of potassium fluoride (17 g) in 600 mL H$_2$O and 1N HCl (86 mL), followed by brine. The organic phase was dried (Na$_2$SO$_4$), filtered and concentrated under reduced pressure to provide a 7:1 (S-2G:S-2H) enriched mixture of Preparations S-2G and S-2H (10.0 g, 100%): $^1$H NMR of diastereoisomer mixture (400 MHz, CDCl$_3$) δ 5.81-5.66 (m, 1H), 5.17-5.04 (m, 2H), 2.81-2.62 (m, 2H), 2.45-2.38 (m, 2H), 2.33-2.03 (m, 3H), 1.96-1.83 (m, 2H), 1.45 (s, 9H, t-Bu of S-2G, integrates for relative intensity of 7), 1.44 (s, 9H, t-Bu of S-2H, integrates for relative intensity of 1).

Intermediate S-2I: (2S,3R)-4-Benzyl 1-tert-butyl 2-allyl-3-(3,3,3-trifluoropropyl)succinate (S-2I)

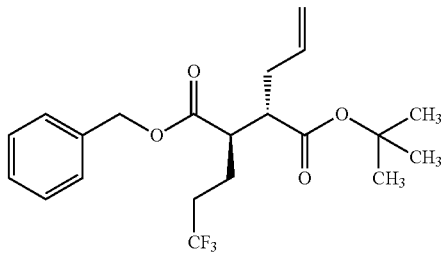

To a stirred solution of a 7:1 enriched mixture of Preparations S-2G and S-2H (10 g, 32.2 mmol) in DMF (100 ml) was added benzyl bromide (4.6 ml, 38.7 mmol) and potassium carbonate (6.68 g, 48.3 mmol). The reaction mixture was stirred for two hours at room temperature. To the reaction mixture was added Et$_3$N (9.0 mL. 64.5 mmol), followed by stirring for 60 min. The reaction mixture was diluted with Et₂O, washed with 10% LiCl (3×100 mL), brine (100 mL), and then dried (Na₂SO₄), filtered and concentrated. The residue was purified by silica gel chromatography (hexane/toluene) to provide Intermediate S-2I (8.7 g, 67%): ¹H NMR (400 MHz, CDCl₃) δ 7.40-7.31 (m, 5H), 5.70 (ddt, J=16.9, 10.2, 7.1 Hz, 1H), 5.19-5.11 (m, 2H), 5.09-5.02 (m, 2H), 2.83-2.68 (m, 2H), 2.43-2.32 (m, 2H), 2.19-1.94 (m, 2H), 1.91-1.81 (m, 2H), 1.42 (s, 9H).

Intermediate S-2E: (2R,3S)-1-Benzyl 4-tert-butyl 3-(cyclopropylmethyl)-2-(3,3,3-trifluoropropyl)succinate

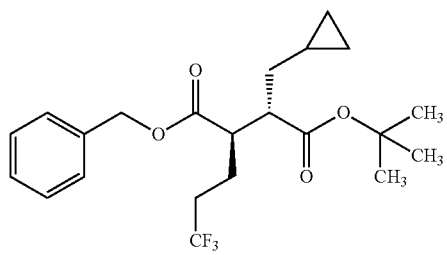

(S-2E)

To a mixture of 40% KOH [KOH (6 g, 107 mmol) in water (9 mL)] and Et₂O (60 mL) cooled to 0° C. was added 1-methyl-3-nitro-1-nitrosoguanidine (1.5 g, 10.20 mmol) portionwise. The obtained solution was swirled several times. The ether layer (yellow solution) was pipetted to a mixture of Intermediate S-2I (450 mg, 1.124 mmol) and Pd(OAc)₂ (25 mg, 0.11 mmol) in Et₂O (18 mL) at 0° C. The mixture was stirred at 0° C. for 3 h, and then the reaction mixture was quenched with several drops of acetic acid. The resulting mixture was washed with saturated NaHCO₃ and brine, dried over MgSO₄, filtered and concentrated. The above oil was purified by silica gel chromatography (hexane/EtOAc) to give Intermediate S-2E (377 mg, 81%) as a colorless oil: ¹H NMR (400 MHz, CDCl₃) δ 7.43-7.31 (m, 5H), 5.21-5.07 (m, 2H), 2.76-2.62 (m, 2H), 2.18-1.66 (m, 4H), 1.58-1.54 (m, 1H), 1.46 (s, 9H), 1.14 (ddd, J=13.8, 7.1, 3.5 Hz, 1H), 0.71-0.53 (m, 1H), 0.47-0.34 (m, 2H), 0.05-0.10 (m, 2H); HPLC: RT=3.790 min (CHROMOLITH® SpeedROD column 4.6× 50 mm, 10-90% aqueous methanol over 4 minutes containing 0.1% TFA, 4 mL/min, monitoring at 220 nm); MS(ES): m/z=415 [M+H]⁺.

Intermediate S-3: (R)-2-(((R)-2-(tert-Butoxy)-2-oxo-1-phenylethyl)-5,5,5-trifluoropentanoic acid

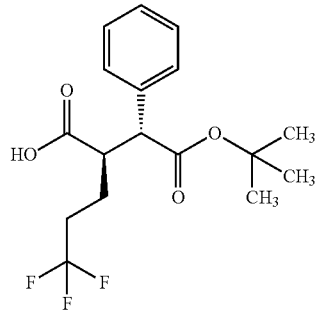

(S-3)

Intermediate S-3A: (2R)-5,5,5-Trifluoro-2-hydroxypentanoic acid

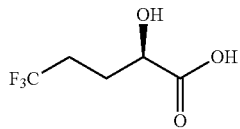

(S-3A)

To a cool (0° C.), stirred solution of (2R)-2-amino-5,5,5-trifluoropentanoic acid (4.09 g, 23.90 mmol) (U.S. Pat. No. 2009/0111858 A1) and H₂SO₄ (2.8 mL, 52.5 mmol) in water (95 mL) was added a solution of sodium nitrite (9.89 g, 143 mmol) in water (30 mL) dropwise via addition funnel over 60 min. The reaction mixture was allowed to slowly warm to room temperature and stirred overnight. The reaction mixture was diluted with Et₂O, the aqueous phase was separated and extracted with Et₂O (3×). The combined organics were dried (Na₂SO₄), filtered and concentrated under reduced pressure to provide Intermediate S-3A (4.1551 g, >99%) as an amber oil: ¹H NMR (400 MHz, CDCl₃) δ ppm 4.33 (1H, dd, J=8.03, 4.27 Hz), 2.09-2.42 (3H, m), 1.88-2.02 (1H, m).

Intermediate S-3B: Benzyl (2R)-5,5,5-trifluoro-2-hydroxypentanoate

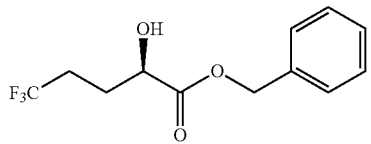

(S-3B)

To a stirred solution of Intermediate S-3A (4.1551 g, 24.14 mmol), benzyl alcohol (3.2 mL, 30.8 mmol) in benzene (40 mL) was added H₂SO₄ (0.28 mL, 5.25 mmol). The reaction mixture was heated to 50° C. for 10 h. The reaction mixture was cooled to room temperature, then cooled in ice/water bath and then 0.5M NaOH (32 mL, 16.00 mmol) was added. The mixture was stirred for a few minutes, and was extracted with Et₂O, washed with brine, dried (Na₂SO₄), filtered and concentrated under reduced pressure. The residue was purified by flash chromatography (Teledyne ISCO CombiFlash Rf, 0% to 100% solvent CH₂Cl₂/EtOAc, REDISEP® SiO₂ 120 g). Concentration of appropriate fractions provided Intermediate S-3B (3.88 g, 61%) as a colorless oil: ¹H NMR (400 MHz, CDCl₃) δ ppm 7.33-7.44 (5H, m), 5.25 (2H, s), 4.28 (1H, dt, J=8.09, 4.11 Hz), 2.85 (1H, d, J=4.77 Hz), 2.07-2.34 (3H, m), 1.84-1.96 (1H, m).

Intermediate S-3C: Benzyl (2R)-5,5,5-trifluoro-2-{[(trifluoromethyl)sulfonyl]oxy}pentanoate

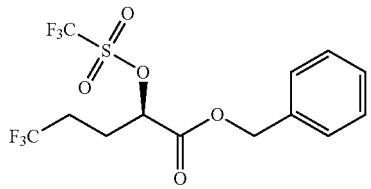

(S-3C)

To a cold (−25° C.), stirred solution of 2,6-lutidine (2.352 mL, 20.19 mmol) in CH₂Cl₂ (30 mL) was added triflic anhydride (3.18 mL, 18.85 mmol) slowly over 2 minutes. The reaction mixture was stirred at −25° C. and became light yellow/orange in color. After 10 min, Intermediate S-3B (3.53 g, 13.46 mmol) was added dropwise over 5 min and stirred at −25° C. for 30 minutes. The reaction mixture was warmed to room temperature and concentrated to a small volume. The residue was diluted with heptane and loaded directly onto a silica gel column (220 g), eluted with a gradient from 20% CH$_2$Cl$_2$/heptane to 50% CH$_2$Cl$_2$/heptane. Concentration of appropriate fractions provided Intermediate S-3C (3.476 g, 66%): $^1$H NMR (400 MHz, CDCl$_3$) δ ppm 7.33-7.45 (5H, m), 5.29 (2H, d, J=5.50 Hz), 5.21 (1H, t, J=5.50 Hz), 2.04-2.37 (4H, m).

Intermediate S-3D: tert-Butyl 2-phenylacetate

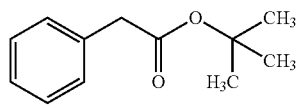
(S-3D)

A solution of 2-phenylacetic acid (12 g, 88 mmol) in t-BuOAc (250 mL) in a 1 L round-bottomed flask was treated with perchloric acid (70% redistilled, 0.212 mL, 3.53 mmol) and stirred at room temperature for 20 hours. The solution was transferred very slowly to stirred mixture of saturated aqueous NaHCO$_3$ and Et$_2$O. Gas evolution was observed. The resulting layers were separated and the organic layer was washed with saturated aqueous NaHCO$_3$, dried over MgSO$_4$, filtered, and concentrated to give Intermediate S-3D (11.6 g, 68% yield): $^1$H NMR (500 MHz, chloroform-d) δ 7.34-7.29 (m, 2H), 7.28-7.22 (m, 3H), 3.52 (s, 2H), 1.44 (s, 9H).

Intermediate S-3E: (2R,3R)-1-Benzyl 4-tert-butyl 3-phenyl-2-(3,3,3-trifluoropropyl)succinate

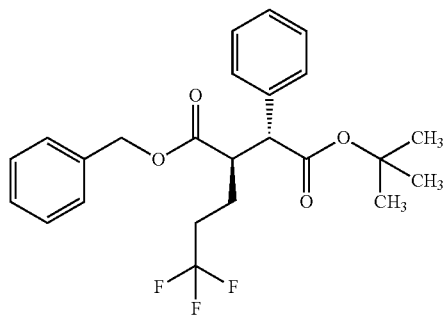
(S-3E)

A solution of Intermediate S-3D (8.5 g, 44.2 mmol) in THF (400 mL) in a 1 L round-bottomed flask was cooled in −78° C. bath and treated with a solution of KHMDS (0.5M in toluene, 97 mL, 48.6 mmol) via cannula over 10 minutes. After 10 minutes the mixture was removed from the −78° C. bath and placed in a room temperature water bath and stirred for 15 minutes and then again cooled in a −78° C. bath. After 15 minutes a solution of Intermediate S-3C (19.18 g, 48.6 mmol) in THF (50 mL) in a 100 mL round bottom flask was added over 10 min via cannula with a 20 mL THF rinse. The reaction mixture turned cloudy. The reaction mixture was stirred at −78° C. for 1 hour. The reaction was quenched with saturated aqueous NH$_4$Cl. The reaction mixture was removed from the −78° C. bath, diluted with 10% aqueous LiCl, and extracted with Et$_2$O. The organic layer was dried over MgSO$_4$, filtered and concentrated. The resulting light brown residue was dissolved in 100 mL CH$_2$Cl$_2$ and treated with charcoal. The solution was dried again with MgSO$_4$ and filtered through MgSO$_4$ with CH$_2$Cl$_2$ rinses to give an almost colorless solution. The CH$_2$Cl$_2$ solution was concentrated and diluted with hexane and cooled in −20° C. freezer. The resulting solids were filtered and rinsed with cold hexane (with 5% MTBE) and dried on filter frit under a stream of nitrogen to give 8.16 g. The solid was triturated with 40 mL hexane and 4 mL MTBE. The white suspension was stirred at room temperature for 1 hour and with cooling at −20° C. for 3 hours before filtering the white solid and washing with cold 10:1 hexane: MTBE rinses. The resulting material was dried on filter frit to give Intermediate S-3E (7.16 g, 37% yield) as a white solid: $^1$H NMR (500 MHz, chloroform-d) δ 7.32-7.23 (m, 8H), 7.05-6.97 (m, 2H), 4.89-4.76 (m, 2H), 3.69 (d, J=11.4 Hz, 1H), 3.23 (ddd, J=11.2, 9.9, 3.9 Hz, 1H), 2.19-2.04 (m, 2H), 2.03-1.88 (m, 2H), 1.40 (s, 9H).

Intermediate S-3

In a 250 mL round-bottomed flask, a suspension of Intermediate S-3E (7.16 g, 16.40 mmol) and Pd/C, 10% (1.746 g, 1.640 mmol) in ethyl acetate (35 mL) and MeOH (35 mL) was hydrogenated using a hydrogen filled balloon while stirring at room temperature. When the reaction was complete (monitored by HPLC) the suspension was filtered through a 0.45 μm membrane and rinsed with MeOH and EtOAc. The filtrate was concentrated and dried under vacuum to give Intermediate S-3 (5.65 g, 99% yield): MS: m/z=345 [M−1]$^-$. $^1$H NMR (500 MHz, DMSO-d$_6$) δ 7.37-7.26 (m, 5H), 3.67 (d, J=10.5 Hz, 1H), 3.04 (td, J=10.3, 3.7 Hz, 1H), 2.38-2.20 (m, 2H), 1.88-1.70 (m, 2H), 1.37 (s, 9H).

Intermediate B-4: (S)-tert-Butyl (9-chloro-2-oxo-2,3,4,5-tetrahydro-1H-benzo[b][1,4]diazepin-3-yl)carbamate

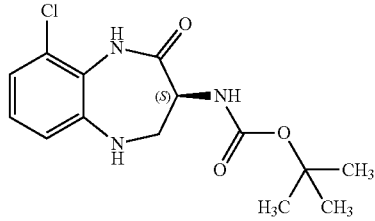
(B-4)

Intermediate B-4A: (S)-2-((tert-Butoxycarbonyl)amino)-3-((3-chloro-2-nitrophenyl)amino)propanoic acid

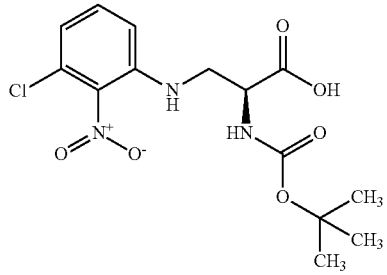
(B-4A)

To a stirred solution of 1-chloro-3-fluoro-2-nitrobenzene (2.28 g, 12.99 mmol) and N-alpha-Boc-beta-amino-L-alanine (2.92 g, 14.30 mmol) in ethanol (30 mL) under $N_2$ was added potassium carbonate (5.40 g, 39.1 mmol). The suspension was heated to 80° C. with stirring for 9 hours at which time LCMS showed complete reaction. The reaction mixture was cooled to room temperature and then concentrated in vacuo. The residue was dissolved in water, extracted with $Et_2O$ (2×), the aqueous phase was cooled in ice then acidified to pH 3 with concentrated HCl, extracted with $CH_2Cl_2$ (4×), the combined extracts were dried ($MgSO_4$), filtered and concentrated. Obtained Intermediate B-4A (2.89 g, 62% yield) as a yellow solid: HPLC: RT=1.967 min (Waters SunFire $C_{18}$ 2.1×30 mm, MeOH/$H_2O$/0.1% TFA, 2 min gradient, wavelength=254 nm); MS(ES): m/z=304 [M-t-Bu+1]$^+$.

Intermediate B-4B: (S)-3-((2-Amino-3-chlorophenyl)amino)-2-((tert-butoxycarbonyl)amino)propanoic acid

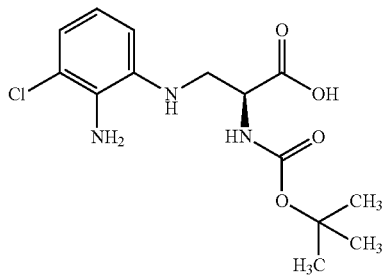

(B-4B)

To a stirred mixture of Intermediate B-4A (2.89 g, 8.03 mmol) and ammonium chloride (aq. saturated, 15 mL) in EtOH (100 mL) was added iron (1.7992 g, 32.2 mmol), then heated to 80° C. for 1.5 hr, at which time LCMS showed complete reaction. To the cool reaction mixture was added ~100 mL EtOAc, filtered through CELITE®, washed with EtOAc. The mixture was partitioned with brine (100 mL), the pH was adjusted to pH 3-4 with 1N HCl, the aqueous phase was back extracted with ethyl acetate (2×200 mL), the combined organic phases were dried ($Na_2SO_4$), filtered and concentrated. Obtained Intermediate B-4B (2.84 g) as a dark red solid that was used directly in the next reaction without further purification: HPLC: RT=1.837 min (Waters SunFire $C_{18}$ 2.1×30 mm, MeOH/$H_2O$/0.1% TFA, 2 min gradient, wavelength=254 nm); MS(ES): m/z=330 [M+1]$^+$.

Intermediate B-4

To a stirred solution of Intermediate B-4B (2.84 g, 8.61 mmol) and TBTU (3.04 g, 9.47 mmol) in DMF (35 mL) was added $Et_3N$ (3.6 mL, 25.8 mmol). After 3 h, LCMS showed complete reaction. The mixture was diluted with EtOAc (300 mL), washed with 10% LiCl (3×100 mL) and saturated aqueous NaCl, and then dried ($Na_2SO_4$), filtered, concentrated, and dried under vacuum overnight. The residue was purified by flash chromatography (Teledyne ISCO CombiFlash Rf, gradient of 0% to 100% using solvent A/B=heptane/EtOAc over 12 column volumes, REDISEP® $SiO_2$ 80 g, loaded as DCM solution). Obtained Intermediate B-4 (1.60 g, 60% yield)) as a yellow solid: HPLC: RT=1.757 min (Waters SunFire $C_{18}$ 2.1×30 mm, MeOH/$H_2O$/0.1% TFA, 2 min gradient, wavelength=254 nm); MS(ES): m/z=256 [M-t-Bu+H]$^+$; $^1$H NMR (400 MHz, chloroform-d) δ 7.49 (br. s., 1H), 6.88-6.99 (m, 2H), 6.66 (dd, J=2.75, 6.71 Hz, 1H), 5.72 (d, J=4.40 Hz, 1H), 4.53 (td, J=5.06, 10.12 Hz, 1H), 3.86-4.04 (m, 2H), 3.47 (t, J=10.56 Hz, 1H), 1.45 (s, 9H).

Intermediate B-5: (S)-tert-Butyl (9-(difluoromethyl)-2-oxo-2,3,4,5-tetrahydro-1H-benzo[b][1,4]diazepin-3-yl)carbamate

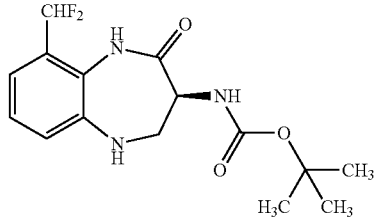

(B-5)

Intermediate B-5A: 1-(Difluoromethyl)-3-fluoro-2-nitrobenzene

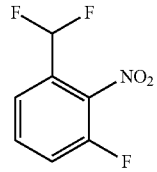

(B-5A)

To a cold solution of 3-fluoro-2-nitrobenzaldehyde (3.0 g, 17.74 mmol) in anhydrous $CH_2Cl_2$ (90 mL) was slowly added (diethylamino)sulfur trifluoride (5.15 mL, 39 mmol) over 5 min. The resulting solution was removed from the cooling bath and allowed to stir at room temperature for 1 hr. The reaction mixture was cooled to −78° C. and poured into a rapidly stirred mixture of ice (450 mL) and saturated aqueous sodium bicarbonate solution (250 mL). The resulting two phase mixture was diluted with dichloromethane (400 mL) and the organic layer was separated. The aqueous layer was back extracted with dichloromethane (250 mL), the organic layers are combined, washed with water (1×75 mL), brine (1×75 mL), dried over sodium sulfate, filtered and evaporated to dryness. The resulting crude product was purified by silica gel chromatography (BIOTAGE® SP1 instrument on a 40 g Thomson SINGLE STEP® Silica cartridge using a hexane/dichloromethane gradient) to give Intermediate B-5A (3.0 g, 89%) as a yellow oil: $^1$H NMR (500 MHz, chloroform-d) δ 7.73-7.64 (m, 1H), 7.59 (dd, J=7.9, 0.5 Hz, 1H), 7.46 (t, J=8.9 Hz, 1H), 7.01 (t, J=55.2 Hz, 1H).

Intermediate B-5B: (S)-2-((tert-Butoxycarbonyl)amino)-3-((3-(difluoromethyl)-2-nitrophenyl)amino)propanoic acid

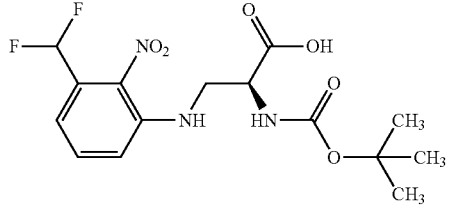

(B-5B)

To a 150 mL pressure bottle were added Intermediate B-5A (2.5 g, 13.08 mmol), N-alpha-Boc-beta-amino-L-alanine (2.95 g, 14.44 mmol), potassium carbonate (5.53 g, 40.0 mmol) and absolute EtOH (80 mL). The reaction mixture was flushed briefly with $N_2$. The vessel was securely capped and placed in an 85° C. oil bath and then heated overnight. The reaction mixture was cooled to room temperature. The solvent was evaporated in vacuo, the residue was partitioned between EtOAc (1200 mL) and water (200 mL). The aqueous phase was acidified to pH 2-3 by the addition of 1.0M HCl, and the layers were separated. The water layer was back extracted with EtOAc (300 mL), then the organic layers were combined, washed with brine (1×75 mL), dried ($Na_2SO_4$), filtered and concentrated. Obtained Intermediate B-5B (5.1 g) as a yellow/red oil: HPLC: RT=3.568 min (PHENOMENEX® Luna 2.0×50 mm 3 μm, 0.8 mL/min MeOH/$H_2O$/ 0.1% TFA, 4 min gradient, wavelength=254 nm); MS(ES): m/z=398 [M+Na]$^+$.

Intermediate B-5C: (S)-3-((2-Amino-3-(difluoromethyl)phenyl)amino)-2-((tert-butoxycarbonyl)amino)propanoic acid

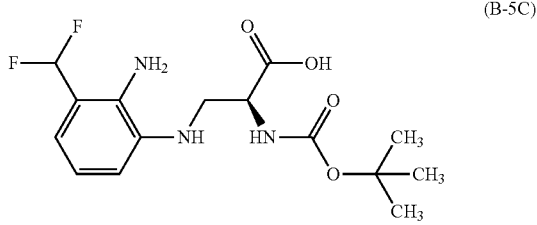 [SMILES: CC(C)(C)OC(=O)N[C@@H](CNc1cccc(C(F)F)c1[N+](=O)[O-])C(=O)O]

(B-5C)

To a solution of Intermediate B-5B (5.1 g, 13.59 mmol) in MeOH (350 mL) under $N_2$ was added palladium on carbon, 10% (1.05 g, 1.973 mmol) and palladium hydroxide on carbon, 20%, Degussa type (1.14 g, 0.812 mmol). The resulting suspension was flushed with $N_2$, then purged with $H_2$ (balloon) and allowed to stir at room temperature under an atmosphere of $H_2$ (balloon). After 85 min, the reaction mixture was purged with $N_2$, then filtered thru a small pad of CELITE® and evaporated to dryness. The residue was dissolved in $CH_2Cl_2$ (75 mL) and evaporated to dryness (repeated 3×) to afford Intermediate B-5C. HPLC: RT=1.880 min (PHENOMENEX® Luna 2.0×50 mm 3 μm, 0.8 mL/min MeCN: water: 10 mM Ammonium Acetate, 4 min gradient, wavelength=254 nm); MS(ES): m/z=346 [M+1]$^+$.

Intermediate B-5

To a solution of crude Intermediate B-5C (4.69 g, 13.59 mmol) in anhydrous $CH_2Cl_2$ (200 mL) was added 1-hydroxy-7-azabenzotriazole (HOAT, 370 mg, 2.72 mmol). The resulting solution was flushed well with $N_2$, then treated with EDC (3.4 g, 17.74 mmol), followed immediately by N-methylmorpholine (7.8 mL, 70.9 mmol). The resulting pale yellow/orange solution was flushed well with $N_2$, capped and allowed to stir at room temperature overnight. The reaction mixture was concentrated, and the residue was dissolved in $CH_2Cl_2$ and evaporated to dryness. The residue was dissolved in $CH_2Cl_2$, applied to the head of a 90 g Thomson SINGLE STEP® Silica cartridge, and eluted with a linear gradient from 100% $CH_2Cl_2$ to 35% EtOAc/$CH_2Cl_2$ over 10 column volumes. Fractions containing pure product were combined, concentrated and dried under vacuum to afford the product (985.5 mg) as a yellow solid. Impure fractions were concentrated, and repurified as follows: dissolved in $CH_2Cl_2$ (15 mL) and applied to the head of a 90 g Thomson SINGLE STEP® Silica cartridge. Eluted column with a linear gradient from 100% $CH_2Cl_2$ to 35% EtOAc/$CH_2Cl_2$ over 10 column volumes. Fractions containing pure product were combined and evaporated to dryness to give 1.03 g yellow solid. Combined with previous clean fraction to provide Intermediate B-5 (2.02 g, 45%) light yellow solid: HPLC: RT=2.715 min (PHENOMENEX® Luna 2.0×50 mm 3 μm, 0.8 mL/min MeCN: water: 10 mM ammonium acetate, 4 min gradient, wavelength=254 nm); MS(ES): m/z=326 [M−1]$^-$; $^1$H NMR (500 MHz, chloroform-d) δ 7.49 (br. s., 1H), 7.18-7.10 (m, 1H), 7.06 (d, J=7.6 Hz, 1H), 6.95 (d, J=7.9 Hz, 1H), 6.68 (t, J=54.8 Hz, 1H), 5.66 (d, J=6.1 Hz, 1H), 4.60 (dt, J=11.3, 5.8 Hz, 1H), 3.99 (dt, J=10.4, 5.4 Hz, 1H), 3.81 (d, J=4.9 Hz, 1H), 3.51 (t, J=10.7 Hz, 1H), 1.45 (s, 9H).

The Boc-protected 1,5-benzodiazepinones in Table 1 were prepared according to the general procedure described for Intermediates B-4 or B-5, starting from the appropriately substituted 2-nitrofluorobenzene (Compound i, Scheme 1) as indicated.

TABLE 1

| Intermediate | Benzodiazepine | General Compound i | HPLC RT | LC/MS |
|---|---|---|---|---|
| B-6 | | 3-Fluoro-2-nitrobenzene | 1.62$^a$ | 277 |
| B-7 | | 2,6-difluoronitrobenzene | 1.72$^a$ | 296 |

TABLE 1-continued

| Intermediate | Benzodiazepine | General Compound i | HPLC RT | LC/MS |
|---|---|---|---|---|
| B-8 | 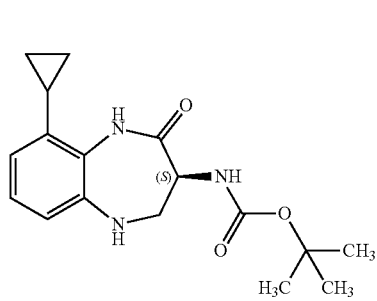 | 1-bromo-3-fluoro-2-nitrobenzene | 2.823[a] | 356 |
| B-9 | 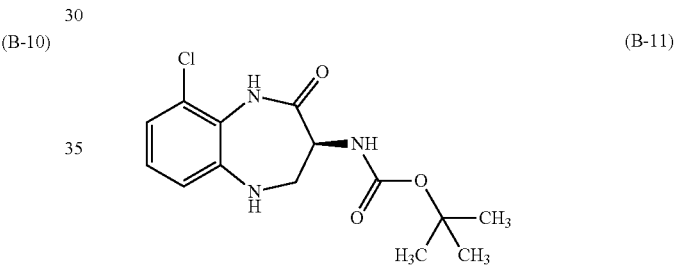 | 1,4-difluoro-2-nitro-benzene | 2.39[a] | 296 |

[a]Waters SunFire $C_{18}$ 2.1 × 30 mm 2.5μ, MeOH/$H_2O$/0.1% TFA, 4 min gradient, wavelength = 220 nm.
[b]PHENOMENEX ® Luna $C_{18}$, 50 mm × 2 mm, 3μ, $CH_3CN$/$H_2O$/10 mM ammonium acetate, 4 min gradient, wavelength = 254 nm

Intermediate B-10: (S)-tert-Butyl (9-cyclopropyl-2-oxo-2,3,4,5-tetrahydro-1H-benzo[b][1,4]diazepin-3-yl)carbamate (B-10)

Ref. U.S. Publication No. 2007/185058 A1 (2007).

To a stirred solution of Intermediate B-8 (500 mg, 1.404 mmol), cyclopropylboronic acid (174 mg, 2.021 mmol), potassium phosphate, tribasic (1064 mg, 5.01 mmol) and tricyclohexylphosphine (26.4 mg, 0.094 mmol) in toluene (10 ml) and water (0.5 ml) under $N_2$ was added palladium(II) acetate (41.0 mg, 0.182 mmol). The mixture was purged with $N_2$ (pump/$N_2$×4) and then was heated to 100° C. with stirring overnight. The reaction mixture was cooled to room temperature and then partitioned between $Et_2O$ and $H_2O$. The organic phase was separated, the aqueous phase was extracted with $Et_2O$ (twice), the combined organic phases washed with brine, dried with sodium sulfate and concentrated to afford a brown oil. The crude product mixture was purified via ISCO (0% to 100% of EtOAC/heptane in 15 minutes, using 40 g column) to obtain Intermediate B-10 (360 mg, 81%): HPLC: RT=2.76 min (Waters SunFire $C_{18}$ 3.5 μ, 2.1×30 mm, 1 mL/min MeOH/$H_2O$/0.1% TFA, 4 min gradient, wavelength=254 nm); MS(ES): m/z=318 [M+1]$^+$; $^1$H NMR (400 MHz, chloroform-d) δ 7.65-7.50 (m, 1H), 7.08-6.82 (m, 1H), 6.68 (d, J=7.9 Hz, 2H), 5.78-5.62 (m, 1H), 4.68-4.44 (m, 1H), 4.05-3.87 (m, 1H), 3.81-3.65 (m, 1H), 3.60-3.38 (m, 2H), 1.91-1.72 (m, 1H), 1.46 (s, 9H), 1.23 (t, J=7.0 Hz, 1H), 0.91 (s, 2H), 0.54-0.30 (m, 1H).

Intermediate B-11: (S)-tert-Butyl (9-cyano-2-oxo-2,3,4,5-tetrahydro-1H-benzo[b][1,4]diazepin-3-yl)carbamate (B-11)

In a 250 mL round-bottom flask equipped with a condenser, septum, $N_2$/vacuum inlet and a magnetic stir-bar, a mixture of Intermediate B-8 (991.0 mg, 2.78 mmol), zinc cyanide (394.4 mg, 3.36 mmol), zinc powder (191.4 mg, 2.93 mmol) and bis(tri-t-butylphosphine)palladium (0) (72.3 mg, 0.141 mmol) in DMA (55 mL) was degassed by evacuating with vacuum and back filling with nitrogen (4×). The mixture was then heated at 100° C. After 1.5 h, the reaction mixture was cooled to room temperature. The mixture was diluted with EtOAc (500 mL), washed with 10% LiCl (3×125 mL), brine (1×125 mL), dried ($Na_2SO_4$), filtered and concentrated, and dried under vacuum overnight. The residue was purified by flash chromatography (Teledyne ISCO CombiFlash Rf, gradient of 0% to 100% using solvent A/B=heptane/EtOAc over 12 column volumes, REDISEP® $SiO_2$ 40 g, loaded as DCM solution). Obtained Intermediate B-11 (721.5 mg, 86%) as a pale yellow solid: HPLC: RT=0.76 min (BEH $C_{18}$ 2.1×50 mm 1.7μ, $CH_3CN$/$H_2O$/0.05% TFA, 1 min gradient, wavelength=254 nm); MS(ES): m/z=303 [M+1]$^+$; base peak m/z=247 [M-t-Bu]$^+$; $^1$H NMR (400 MHz, chloroform-d) δ 7.58 (br. s., 1H), 7.10-7.15 (m, 1H), 7.03-7.10 (m, 1H), 6.93 (dd, J=1.10, 8.14 Hz, 1H), 5.74 (d, J=4.40 Hz, 1H), 4.48-4.59 (m, 1H), 4.18 (d, J=6.16 Hz, 1H), 3.91 (ddd, J=3.85, 7.21, 11.17 Hz, 1H), 3.45-3.54 (m, 1H), 1.45 (s, 9H).

Intermediate B-12: (S)-3-Amino-9-chloro-5-(3-cyclopropylphenyl)-4,5-dihydro-1H-benzo[b][1,4]diazepin-2(3H)-one

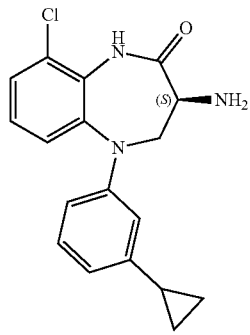

(B-12)

Intermediate B-12A: (S)-tert-Butyl (6-chloro-1-(3-cyclopropylphenyl)-4-oxo-2,3,4,5-tetrahydro-1H-benzo[b][1,4]diazepin-3-yl)carbamate

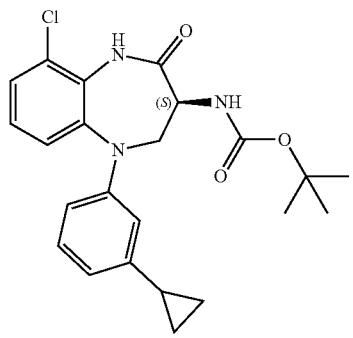

(B-12A)

A stirred suspension of Intermediate B-4 (201.8 mg, 0.647 mmol), 1-bromo-3-cyclopropylbenzene (246.7 mg, 1.252 mmol), Pd$_2$(dba)$_3$ (58.5 mg, 0.064 mmol), 2-(dicyclohexylphosphino)-2',4',6'-triisopropylbiphenyl ("X-Phos") (30.7 mg, 0.064 mmol) and potassium carbonate (414.7 mg, 3.00 mmol) in t-BuOH (4.0 mL) was degassed (pump/N$_2$×3) and then heated to 80° C. overnight. The reaction mixture was cooled to room temperature. The mixture was diluted with EtOAc, filtered through a 4 µm membrane filter, concentrated, and then dried under vacuum. The residue was purified by flash chromatography (Teledyne ISCO CombiFlash Rf, gradient of 0% to 100% using solvent A/B=heptane/EtOAc over 15 column volumes, REDISEP® SiO$_2$ 40 g, loaded as DCM solution). Obtained Intermediate B-12A (134.0 mg, 48%) as a tan solid: HPLC: RT=2.218 min (Waters SunFire C$_{18}$ 2.1×30 mm, MeOH/H$_2$O/0.1% TFA, 2 min gradient, wavelength=254 nm); MS(ES): m/z=372/374 [M-t-Bu+1]$^+$; $^1$H NMR (400 MHz, chloroform-d) δ 7.05-7.15 (m, 1H), 6.59 (d, J=7.70 Hz, 1H), 6.47-6.55 (m, 2H), 5.61 (d, J=7.26 Hz, 1H), 4.53-4.65 (m, 1H), 4.26-4.33 (m, 1H), 3.66 (dd, J=9.57, 11.77 Hz, 1H), 1.75-1.85 (m, 1H), 1.46 (s, 9H), 0.85-0.97 (m, 2H), 0.57-0.71 (m, 2H).

Intermediate B-12

To a stirred solution of Intermediate B-12A (134.0 mg, 0.313 mmol) in CH$_2$Cl$_2$ (2.0 mL) was added TFA (1.0 mL, 12.98 mmol). After 2 h, LCMS showed complete reaction. The reaction mixture was diluted with toluene, concentrated, and then dried under vacuum overnight. Obtained Intermediate B-12 (156.1 mg, 90%) as a di-TFA solvate: HPLC: RT=1.777 min (PHENOMENEX® Luna C$_{18}$ 2.5 µm 2.0×30 mm, MeOH/H$_2$O/0.1% TFA, 2 min gradient, wavelength=254 nm); MS(ES): m/z=328 [M+1]$^+$.

Intermediate B-13: (S)-3-Amino-9-chloro-5-(6-(trifluoromethyl)pyridin-2-yl)-4,5-dihydro-1H-benzo[b][1,4]diazepin-2(3H)-one

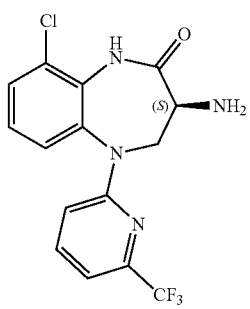 [SMILES: N#Cc1cccc2c1NC(=O)[C@@H](N)CN2c1cccc(C(F)(F)F)c1]

(B-13)

Intermediate B-13A: (S)-tert-Butyl (6-chloro-4-oxo-1-(6-(trifluoromethyl)pyridin-2-yl)-2,3,4,5-tetrahydro-1H-benzo[b][1,4]diazepin-3-yl)carbamate

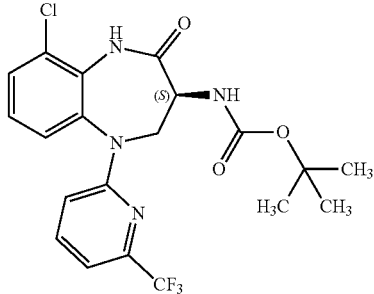

(B-13A)

A 48 mL pressure vessel fitted with a stir bar and a rubber septum was charged with Intermediate B-4 (304.4 mg, 0.976 mmol), Xphos precatalyst (CAS #1028206-56-5) (35.4 mg, 0.048 mmol), Ruphos (CAS #787618-22-8) (26.1 mg, 0.056 mmol) and potassium carbonate (394.4 mg, 2.85 mmol) in t-BuOH (6.0 mL). This mixture was degassed by (vacuum/N$_2$ purge×4). To this was added 2-bromo-6-(trifluoromethyl)pyridine (446.7 mg, 1.977 mmol), the septum removed and Teflon cap tightly installed, then heated to 100° C., stirred for 75 min, then cooled to 50° C., and stirred for 2 days. The reaction mixture was cooled to room temperature and diluted with EtOAc, filtered through CELITE®, washed with EtOAc, concentrated, and then dried under vacuum. The residue was purified by flash chromatography (Teledyne ISCO CombiFlash Rf, gradient of 0% to 100% using solvent A/B=heptane/EtOAc over 12 column volumes, REDISEP® SiO$_2$ 40 g, loaded as DCM solution). Obtained Intermediate B-13A (322.8 mg, 72%) as a tan foam: HPLC: RT=1.05 min (BEH C$_{18}$ 2.1×50 mm 1.7µ, CH$_3$CN/H$_2$O/0.05% TFA, 1 min gradient, wavelength=254 nm); MS(ES): m/z=457 [M+1]+; $^1$H NMR (400 MHz, DMSO-$d_6$) δ 9.86 (s, 1H), 7.69 (t, J=7.81 Hz, 1H), 7.62 (dd, J=1.76, 7.70 Hz, 1H), 7.32-7.44 (m, 3H), 7.22 (d, J=7.26 Hz, 1H), 6.51 (d, J=8.80 Hz, 1H), 4.61-4.73 (m, 1H), 4.20-4.33 (m, 1H), 3.74 (dd, J=7.04, 11.88 Hz, 1H), 1.36 (s, 9H).

Intermediate B-13

To a stirred solution of Intermediate B-13A (316.3 mg, 0.692 mmol) in CH$_2$Cl$_2$ (4 mL) was added TFA (2 mL, 26.0 mmol). After 4 h, LCMS showed the reaction was complete. The mixture was diluted with toluene (10 mL), concentrated then dried under vacuum over the weekend. Obtained Intermediate B-13 (306.5 mg, 94%) as a cream solid as a TFA solvate: HPLC: RT=0.69 min (BEH C$_{18}$ 2.1×50 mm 1.7μ, CH$_3$CN/H$_2$O/0.05% TFA, 1 min gradient, wavelength=254 nm); MS(ES): m/z=357 [M+1]+; $^1$H NMR (400 MHz, DMSO-$d_6$) δ 10.47 (s, 1H), 8.42 (br. s., 3H), 7.73 (t, J=7.92 Hz, 1H), 7.66 (dd, J=1.43, 8.03 Hz, 1H), 7.49 (dd, J=1.32, 8.14 Hz, 1H), 7.38-7.45 (m, 1H), 7.29 (d, J=7.26 Hz, 1H), 6.58 (d, J=8.80 Hz, 1H), 4.80 (t, J=11.99 Hz, 1H), 4.32 (dd, J=6.93, 12.21 Hz, 1H), 3.98 (dd, J=6.93, 11.77 Hz, 1H).

The 5-aryl-1,5-benzodiazepinones in Table 2 were prepared according to the general procedure shown for Intermediate B-12 (for aryl bromides) or B-13 (for bromopyridines), starting from the appropriate Boc-protected-1,5-benzodiazepinones and aryl halide as indicated.

TABLE 2

| Intermediate | Benzodiazepine | Aryl Bromide | HPLC RT | LC/MS |
|---|---|---|---|---|
| B-14 | | 3-chloro-bromobenzene | 2.22[a] | 288 |
| B-15 | | 4-chloro-bromobenzene | 1.54[b] | 288 |
| B-16 | | 3-cyclopropyl-bromobenzene | 1.60[b] | 294 |

TABLE 2-continued

| Intermediate | Benzodiazepine | Aryl Bromide | HPLC RT | LC/MS |
|---|---|---|---|---|
| B-17 | | 4-fluoro-bromobenzene | 1.42[b] | 272 |
| B-18 | | 3-chloro-bromobenzene | 2.65[d] | 376 |
| B-19 | | m-Bromobenzonitrile | 2.41[c] | 351 [M + Na]+ |
| B-20 | | 3-(difluoromethyl)-bromobenzene | 2.70[c] | 376 [M + Na]+ |
| B-21 | | 3-cyano-5-chlorobromo-benzene | 2.77[c] | 385 [M + Na]+ |

TABLE 2-continued

| Intermediate | Benzodiazepine | Aryl Bromide | HPLC RT | LC/MS |
|---|---|---|---|---|
| B-22 | (structure: 9-CHF₂ benzodiazepin-2-one with 3-NH₂, N-aryl = 3-methyl-5-cyanophenyl) | 3-cyano-5-methylbromobenzene | 2.39$^c$ | 343 |
| B-23 | (structure: 9-CHF₂ benzodiazepin-2-one with 3-NH₂, N-aryl = 3-fluoro-5-cyanophenyl) | 3-cyano-5-fluorobromobenzene | 2.52$^c$ | 369 [M + Na]⁺ |
| B-24 | (structure: 9-CN benzodiazepin-2-one with 3-NH₂, N-aryl = 3-CF₃-phenyl) | 3-trifluoromethyl-bromobenzene | 0.70$^e$ | 347 |
| B-25 | (structure: 9-F benzodiazepin-2-one with 3-NH₂, N-aryl = 3-CF₃-phenyl) | 3-trifluoromethyl-bromobenzene | 1.58$^b$ | 340 |
| B-26 | (structure: 9-F benzodiazepin-2-one with 3-NH₂, N-aryl = 3-cyclopropyl-phenyl) | 3-cyclopropyl-bromobenzene | 1.61$^b$ | 311 |

TABLE 2-continued

| Intermediate | Benzodiazepine | Aryl Bromide | HPLC RT | LC/MS |
| --- | --- | --- | --- | --- |
| B-27 | (structure) | 3,4-dichloro-bromobenzene | 1.65[b] | 340 |
| B-28 | (structure) | m-Bromobenzonitrile | 1.67[b] | 267 |
| B-29 | (structure) | 3-chloro-bromobenzene | 1.657[f] | 322 |
| B-30 | (structure) | 4-chloro-bromobenzene | 1.56[b] | 322 |
| B-31 | (structure) | 3,4-dichloro-bromobenzene | 1.815[f] | 356 |

TABLE 2-continued

| Intermediate | Benzodiazepine | Aryl Bromide | HPLC RT | LC/MS |
|---|---|---|---|---|
| B-32 | | 3-trifluoromethyl-bromobenzene | 1.58[b] | 356 |
| B-33 | | m-Bromobenzonitrile | 1.83[b] | 313 |
| B-34 | | o-Bromobenzonitrile | 1.26[a] | 313 |
| B-35 | | 3-cyano-5-fluorobromo-benzene | 1.38[b] | 331 |
| B-36 | | 2-bromopyridine | 0.89[e] | 289 |

TABLE 2-continued

| Intermediate | Benzodiazepine | Aryl Bromide | HPLC RT | LC/MS |
|---|---|---|---|---|
| B-37 | | 2-bromo-4-trifluoromethyl-pyridine | 0.71[e] | 357 |
| B-38 | | bromobenzene | 1.41[b] | 272 |
| B-39 | | 3-trifluoromethyl-bromobenzene | 1.62[b] | 340 |

[a]Waters SunFire $C_{18}$ 2.1 × 30 mm 2.5µ, MeOH/$H_2O$/0.1% TFA, 4 min gradient, wavelength = 220 nm.
[b]Waters SunFire $C_{18}$ 2.1 × 30 mm 2.5µ, MeOH/$H_2O$/0.1% TFA, 2 min gradient, wavelength = 220 nm.
[c]PHENOMENEX ® Luna $C_{18}$, 50 mm × 2 mm, 3µ, $CH_3OH$/$H_2O$/0.1% TFA, 4 min gradient, wavelength = 254 nm.
[d]Waters SunFire $C_{18}$ 3.5µ, 2.1 × 30 mm, 1 mL/min MeOH/$H_2O$/0.1% TFA, 4 min gradient, wavelength = 254 nm
[e]BEH $C_{18}$ 2.1 × 50 mm 1.7µ, $CH_3CN$/$H_2O$/0.05% TFA, 1 min gradient, wavelength = 254 nm.
[f]PHENOMENEX ® Luna $C_{18}$ 2.5 µm 2.0 × 30 mm, MeOH/$H_2O$/0.1% TFA, 2 min gradient, wavelength = 254 nm.

Example 1

(2R,3S)—N-((3S)-6-Chloro-1-(3-cyclopropylphenyl)-4-oxo-2,3,4,5-tetrahydro-1H-1,5-benzodiazepin-3-yl)-2,3-bis(3,3,3-trifluoropropyl)succinamide

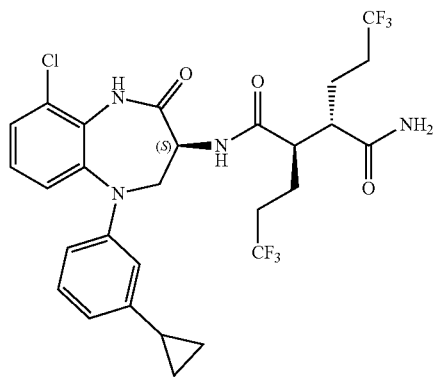

(1)

Preparation 1A: (2S,3R)-tert-Butyl 3-(((S)-6-chloro-1-(3-cyclopropylphenyl)-4-oxo-2,3,4,5-tetrahydro-1H-benzo[b][1,4]diazepin-3-yl)carbamoyl)-6,6,6-trifluoro-2-(3,3,3-trifluoropropyl)hexanoate

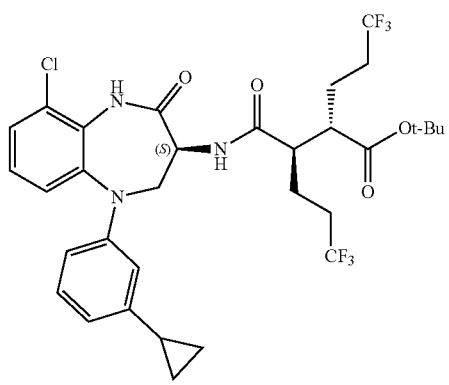

(1A)

To a stirred solution of Intermediate B-12 (64.8 mg, 0.147 mmol), Intermediate S-1 (55.4 mg, 0.151 mmol) and TBTU (54.8 mg, 0.171 mmol) in DMF (1.0 mL) was added Et₃N (0.08 mL, 0.574 mmol). After 2 hr, the reaction mixture was diluted with EtOAc, washed with H₂O, 10% LiCl (3×), sat NaCl then dried (Na₂SO₄), filtered and concentrated, dried under vacuum over the weekend. Obtained Preparation 1A (104.8 mg, 100%) as a pale yellow solid, which was used as is without further purification: HPLC: RT=2.343 min (Waters SunFire C₁₈ 2.1×30 mm, MeOH/H₂O/0.1% TFA, 2 min gradient, wavelength=254 nm); MS(ES): m/z=676 [M+1]⁺.

Preparation 1B: (2S,3R)-3-(((S)-6-Chloro-1-(3-cyclopropylphenyl)-4-oxo-2,3,4,5-tetrahydro-1H-benzo[b][1,4]diazepin-3-yl)carbamoyl)-6,6,6-trifluoro-2-(3,3,3-trifluoropropyl)hexanoic acid

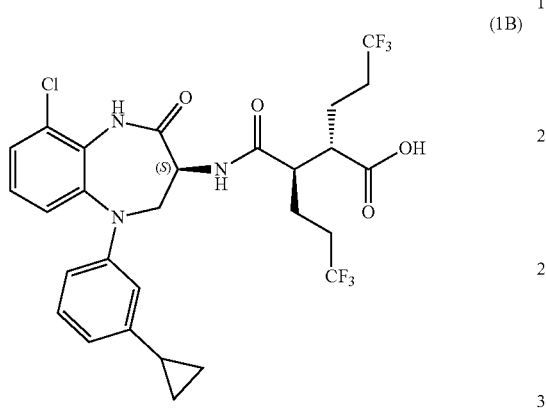

(1B)

To a stirred solution of Preparation 1A (104.8 mg, 0.155 mmol) in CH₂Cl₂ (1 mL) was added TFA (1 mL, 12.98 mmol). After 2.5 hr, LCMS showed complete reaction. The reaction mixture was diluted with toluene (10 mL), concentrated, and then dried under vacuum overnight. Obtained Preparation 1B (110.3 mg, 97%) as a TFA solvate: HPLC: RT=2.208 min (Waters SunFire C₁₈ 2.1×30 mm, MeOH/H₂O/0.1% TFA, 2 min gradient, wavelength=254 nm); MS(ES): m/z=620 [M+1]⁺.

Example 1

To a stirred solution of Preparation 1B (110.3 mg, 0.150 mmol), EDC (92.0 mg, 0.480 mmol) and HOBT (71.9 mg, 0.470 mmol) in THF (2.2 mL) was added ammonia (2.0M in IPA, 0.45 mL, 0.900 mmol). After 1.5 hr, LCMS showed complete reaction. The reaction mixture was partitioned between EtOAc and H₂O, the organic phase was separated, the aqueous phase was extracted with EtOAc, the combined organic phases washed with saturated NaCl, dried (Na₂SO₄), filtered and concentrated to afford a colorless solid. The residue was purified by flash chromatography (Teledyne ISCO CombiFlash Rf, gradient of 0% to 40% using solvent A/B=CH₂Cl₂/acetone over 20 column volumes, REDISEP® SiO₂ 12 g, loaded as DCM solution). Fractions containing product were collected and concentrated, dried under vacuum overnight. This material was further purified by preparative SFC chromatography (Berger SFC MGII, CHIRALPAK® IC 25×3 cm ID, 5 μm, 85/15 CO₂/MeOH, 85 mL/min, Detector Wavelength: 220 nm). Obtained Example 1 (27.9 mg, 30%) as a colorless solid: HPLC: RT=2.150 min (MeOH/H₂O/ 0.1% TFA, Waters SunFire C₁₈ 2.1×30 mm, 2 min gradient, wavelength=254 nm); MS(ES): m/z=619 [M+1]⁺; ¹H NMR (400 MHz, DMSO-d₆) δ 9.88 (s, 1H), 8.64 (d, J=7.70 Hz, 1H), 7.65 (br. s., 1H), 7.44 (dd, J=1.32, 8.14 Hz, 1H), 7.23 (t, J=8.14 Hz, 1H), 7.13 (s, 1H), 7.06-7.11 (m, 2H), 6.57 (d, J=7.92 Hz, 1H), 6.41-6.45 (m, 2H), 4.50 (td, J=7.26, 12.32 Hz, 1H), 3.94 (dd, J=6.82, 9.90 Hz, 1H), 3.81 (dd, J=10.12, 12.10 Hz, 1H), 2.38-2.47 (m, 3H), 2.03-2.23 (m, 3H), 1.77-1.86 (m, 1H), 1.52-1.67 (m, 3H), 1.38-1.50 (m, 1H), 0.87-0.92 (m, 2H), 0.58-0.65 (m, 1H), 0.52-0.58 (m, 1H).

Example 2

(2R,3R)—N-((3S)-1-(3-Cyanophenyl)-6-(difluoromethyl)-4-oxo-2,3,4,5-tetrahydro-1H-1,5-benzodiazepin-3-yl)-3-phenyl-2-(3,3,3-trifluoropropyl)succinamide

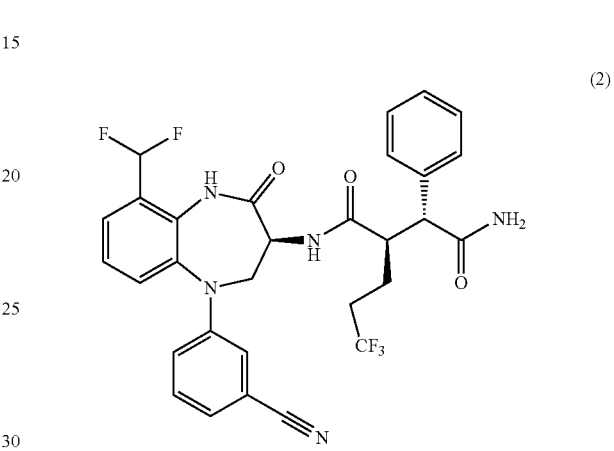

(2)

Preparation 2A: (2R,3R)-tert-Butyl 3-(((S)-1-(3-cyanophenyl)-6-(difluoromethyl)-4-oxo-2,3,4,5-tetrahydro-1H-benzo[b][1,4]diazepin-3-yl)carbamoyl)-6,6,6-trifluoro-2-phenylhexanoate

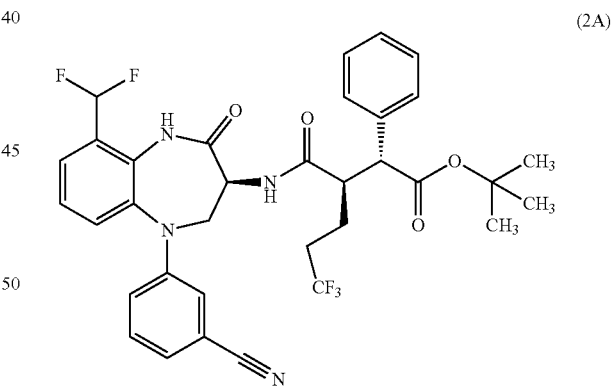

(2A)

To a dry vial under N₂ was added Intermediate B-19 (98 mg, 0.222 mmol), Intermediate S-3 (79 mg, 0.228 mmol), HOAT (11 mg, 0.081 mmol) and anhydrous CH₂Cl₂ (3 mL). The reaction mixture was flushed very briefly with N₂ and then treated with N-methylmorpholine (150 μl, 1.364 mmol). After 20 sec., EDC (54 mg, 0.282 mmol) was added. The reaction mixture was flushed again with N₂, capped and allowed to stir at room temperature. After 3.5 hr, the solvent was evaporated. The residue was dissolved in CH₂Cl₂ (5 mL) and applied to the head of a 25 g Thomson SINGLE STEP® Silica cartridge and eluted with 3 column volumes of CH₂Cl₂, followed by a linear gradient from 100% CH₂Cl₂ to 40%

EtOAc/CH$_2$Cl$_2$ over 5 column volumes. Obtained Preparation 2A (81 mg, 56%) as a white solid: HPLC: RT=3.923 min (PHENOMENEX® Luna 2.0×50 mm 3 μm, 0.8 mL/min MeCN: water: 10 mM ammonium acetate, 4 min gradient, wavelength=254 nm); MS(ES): m/z=657 [M+1]$^+$.

Preparation 2B: (2R,3R)-3-(((S)-1-(3-Cyanophenyl)-6-(difluoromethyl)-4-oxo-2,3,4,5-tetrahydro-1H-benzo[b][1,4]diazepin-3-yl)carbamoyl)-6,6,6-trifluoro-2-phenylhexanoic acid

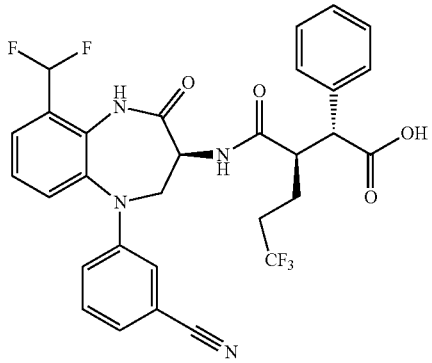

(2B)

To a solution of Preparation 2A (81 mg, 0.123 mmol) in anhydrous CH$_2$Cl$_2$ (7 mL) was added TFA (3 mL, 38.9 mmol) with vigorous stirring. After 1.5 h, additional TFA (1.75 mL) was added to the reaction mixture. The reaction mixture was allowed to stand at room temperature for an additional 60 min. The reaction mixture was concentrated, dissolved in a small amount of CH$_2$Cl$_2$ (10 mL) and anhydrous toluene (30 mL) was added. The mixture was evaporated to dryness overnight. Obtained Preparation 2B (75.3 mg, >99%) as a white solid: HPLC: RT=2.345 min (PHENOMENEX® Luna 2.0× 50 mm 3 μm, 0.8 mL/min MeCN: water: 10 mM ammonium acetate, 4 min gradient, wavelength=254 nm); MS(ES): m/z=601 [M+1]$^+$.

Example 2

To a solution of Preparation 2B (74 mg, 0.123 mmol) in freshly distilled THF (2.0 mL) was added HOAT (70.4 mg, 0.517 mmol), EDC (95 mg, 0.496 mmol) and ammonia (2.0M in 2-propanol, 375 μL, 0.750 mmol). The resulting yellow suspension was allowed to stir at room temperature. After 1 h, LCMS showed the desired product. The reaction mixture was diluted with THF (5 mL) and the stirring bar was removed. Additional NH$_3$ (200 μL) was added with vigorous swirling and the resulting suspension was allowed to stand at room temperature for 1 hr. The reaction mixture was concentrated, dissolved in CH$_2$Cl$_2$ (25 mL), and evaporated to dryness (twice). Next, CH$_2$Cl$_2$ (25 mL) was added and the solid was removed by filtration. The filtrate was applied to the head of a 25 g Thomson SINGLE STEP® Silica cartridge and eluted with a linear gradient from 100% CH$_2$Cl$_2$ to 50% EtOAc/CH$_2$Cl$_2$ over 10 column volumes, with a hold at 40% EtOAc/CH$_2$Cl$_2$ while the desired product eluted off the column. Obtained Example 2 (70 mg, 94%) as a colorless solid: HPLC: RT=2.84 min (MeCN/H$_2$O/10 mM NH$_4$OAc, Luna C$_{18}$ 2×50 mm, 4 min gradient, wavelength=254 nm); MS m/z=600 [M+1]$^+$; 598 [M−1]$^-$; $^1$H NMR (500 MHz, chloroform-d) δ 7.94 (s, 1H), 7.65-7.58 (m, 1H), 7.56-7.44 (m, 5H), 7.35-7.29 (m, 1H), 7.27-7.22 (m, 2H), 7.21-7.17 (m, 1H), 7.12 (d, J=7.0 Hz, 1H), 6.94-6.66 (m, 3H), 5.57 (br. s., 2H), 4.59 (dt, J=11.5, 6.8 Hz, 1H), 3.59-3.53 (m, 1H), 3.51-3.40 (m, 2H), 2.50 (dd, J=11.3, 10.2 Hz, 1H), 2.06-1.95 (m, 3H), 1.94-1.85 (m, 1H).

Example 3

(2R,3S)—N-((3S)-1-(3-Chlorophenyl)-4-oxo-2,3,4,5-tetrahydro-1H-1,5-benzodiazepin-3-yl)-2,3-bis(3,3,3-trifluoropropyl)succinamide

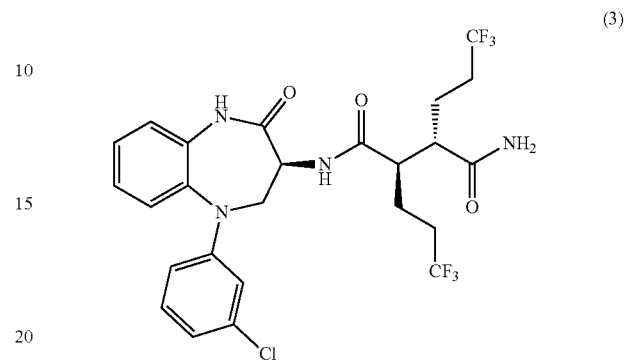

(3)

Example 3 was prepared from Intermediate B-14 (38 mg, 0.131 mmol) and Intermediate S-1 (53 mg, 0.144 mmol) according to the general procedure shown for Example 1. The product was purified by preparative SFC chromatography (Berger SFC MGII, Chiral IC 25×3 cm ID, 5 μm, 90/10 CO$_2$/MeOH, 85.0 mL/min, Detector Wavelength: 220 nm). Example 3 (8 mg, 10%) was obtained: HPLC: RT=2.20 min (MeOH/H$_2$O/0.1% TFA, Waters SunFire C$_{18}$ 2.1×30 mm, 2 min gradient, wavelength=220 nm); MS(ES): m/z=579 [M+1]$^+$; $^1$H NMR (400 MHz, DMSO-d$_6$) δ 10.06 (s, 1H), 8.64 (d, J=8.1 Hz, 1H), 7.65 (br. s., 1H), 7.38-7.31 (m, 1H), 7.28-7.18 (m, 4H), 7.14 (br. s., 1H), 6.86 (dd, J=7.9, 1.3 Hz, 1H), 6.61 (t, J=2.2 Hz, 1H), 6.55 (dd, J=8.5, 2.1 Hz, 1H), 4.63-4.54 (m, 1H), 4.00-3.92 (m, 1H), 3.91-3.82 (m, 1H), 2.24-2.05 (m, 4H), 1.68-1.53 (m, 4H), 1.46 (d, J=11.0 Hz, 1H).

Example 4

(2R,3S)—N-((3S)-1-(4-Chlorophenyl)-4-oxo-2,3,4,5-tetrahydro-1H-1,5-benzodiazepin-3-yl)-2,3-bis(3,3,3-trifluoropropyl)succinamide

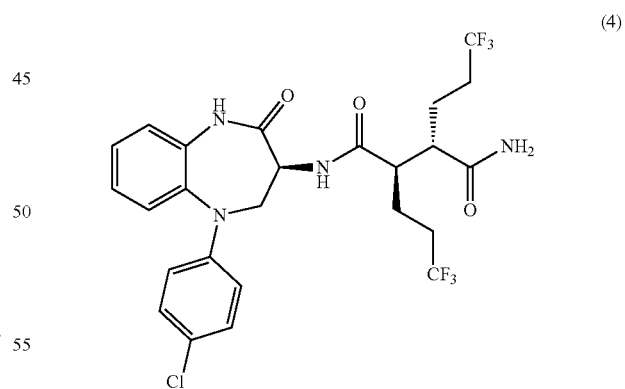

(4)

Example 4 was prepared from Intermediate B-15 (50 mg, 0.175 mmol) and Intermediate S-1 (71 mg, 0.193 mmol) according to the general procedure shown for Example 1. The product was purified by preparative SFC chromatography (Berger SFC MGII, Chiral AS-H 25×3 cm ID, 5 μm, 88/12 CO$_2$/MeOH, 85.0 mL/min, Detector Wavelength: 220 nm). Example 4 (8 mg, 8%) was obtained: HPLC: RT=2.16 min (MeOH/H$_2$O/0.1% TFA, Waters SunFire C$_{18}$ 2.1×30 mm, 2 min gradient, wavelength=220 nm); MS(ES): m/z=579 [M+1]$^+$; $^1$H NMR (400 MHz, DMSO-d$_6$) δ 10.06 (s, 1H), 8.67 (d, J=8.1 Hz, 1H), 7.65 (s, 1H), 7.36-7.10 (m, 8H), 6.69-6.60 (m, 2H), 4.59 (dt, J=12.4, 7.2 Hz, 1H), 3.94 (dd, J=10.2, 6.7 Hz, 1H), 3.88-3.79 (m, 1H), 2.24-2.04 (m, 4H), 1.66-1.54 (m, 4H), 1.45 (d, J=11.2 Hz, 1H).

Example 5

(2R,3S)—N-((3S)-1-(3-Cyclopropylphenyl)-4-oxo-2,3,4,5-tetrahydro-1H-1,5-benzodiazepin-3-yl)-2,3-bis(3,3,3-trifluoropropyl)succinamide (5)

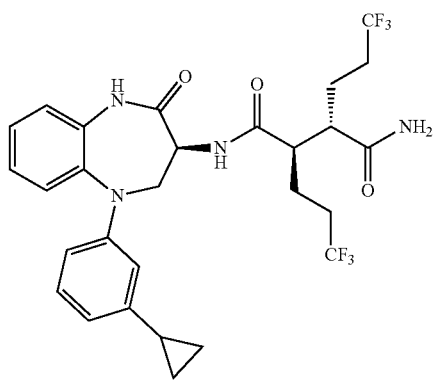

Example 5 was prepared from Intermediate B-16 (78 mg, 0.267 mmol) and Intermediate S-1 (108 mg, 0.294 mmol) according to the general procedure shown for Example 1. The product was purified by preparative SFC chromatography (Berger SFC MGII, Chiral IC 25×3 cm ID, 5 μm, 85/15 CO$_2$/MeOH, 85.0 mL/min, Detector Wavelength: 220 nm). Example 5 (32 mg, 20%) was obtained: HPLC: RT=2.21 min (MeOH/H$_2$O/0.1% TFA, Waters SunFire C$_{18}$ 2.1×30 mm, 2 min gradient, wavelength=220 nm); MS(ES): m/z=585 [M+1]$^+$; $^1$H NMR (400 MHz, DMSO-d$_6$) δ 10.01 (s, 1H), 8.65 (d, J=7.9 Hz, 1H), 7.65 (s, 1H), 7.32-7.25 (m, 1H), 7.23-7.17 (m, 2H), 7.16-7.11 (m, 2H), 7.06 (t, J=8.1 Hz, 1H), 6.54 (d, J=7.7 Hz, 1H), 6.42-6.36 (m, 2H), 4.57 (dt, J=12.5, 7.3 Hz, 1H), 3.98-3.89 (m, 1H), 3.83 (dd, J=12.3, 10.3 Hz, 1H), 2.48-2.40 (m, 2H), 2.25-2.05 (m, 3H), 1.87-1.74 (m, 1H), 1.68-1.53 (m, 3H), 1.52-1.41 (m, 1H), 1.32-1.21 (m, 1H), 0.95-0.82 (m, 2H), 0.65-0.50 (m, 1H).

Example 6

(2R,3S)—N-((3S)-1-(4-Fluorophenyl)-4-oxo-2,3,4,5-tetrahydro-1H-1,5-benzodiazepin-3-yl)-2,3-bis(3,3,3-trifluoropropyl)succinamide (6)

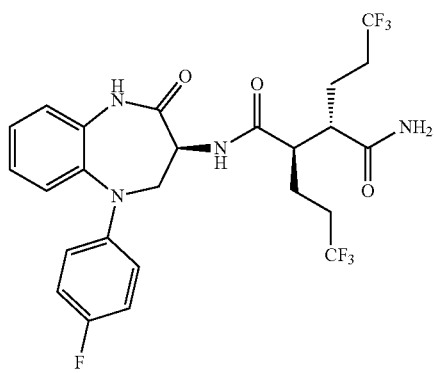

Example 6 was prepared from Intermediate B-17 (45 mg, 0.167 mmol) and Intermediate S-1 (67 mg, 0.184 mmol) according to the general procedure shown for Example 1. The product was purified by preparative SFC chromatography (Berger SFC MGII, Chiral IC 25×3 cm ID, 5 μm, 90/10 CO$_2$/MeOH, 85.0 mL/min, Detector Wavelength: 220 nm). Example 6 (8 mg, 9%) was obtained: HPLC: RT=2.10 min (MeOH/H$_2$O/0.1% TFA, Waters SunFire C$_{18}$ 2.1×30 mm, 2 min gradient, wavelength=220 nm); MS(ES): m/z=563 [M+1]$^+$; $^1$H NMR (400 MHz, DMSO-d$_6$) δ 10.04 (s, 1H), 8.67 (d, J=7.9 Hz, 1H), 7.65 (s, 1H), 7.32-7.24 (m, 1H), 7.22-7.16 (m, 2H), 7.14 (s, 1H), 7.12-7.03 (m, 3H), 6.73-6.64 (m, 2H), 4.62-4.52 (m, 1H), 3.96 (dd, J=9.9, 6.8 Hz, 1H), 3.79 (dd, J=12.3, 10.1 Hz, 1H), 2.47-2.40 (m, 2H), 2.24-2.05 (m, 3H), 1.66-1.53 (m, 3H), 1.45 (d, J=10.3 Hz, 1H), 1.32-1.22 (m, 1H), 0.92-0.84 (m, 1H).

Example 7

(2R,3S)—N-((3S)-1-(3-Chlorophenyl)-6-cyclopropyl-4-oxo-2,3,4,5-tetrahydro-1H-1,5-benzodiazepin-3-yl)-2,3-bis(3,3,3-trifluoropropyl)succinamide (7)

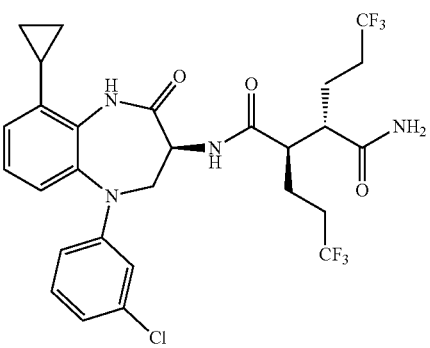

Example 7 was prepared from Intermediate B-18 (75 mg, 0.17 mmol) and Intermediate S-1 (68.3 mg, 0.178 mmol) according to the general procedure shown for Example 1. The product was purified by preparative SFC chromatography (Berger SFC MGII, Chiral OD 25×3 cm ID, 5 μm, 82/18 CO$_2$/MeOH, 85.0 mL/min, Detector Wavelength: 220 nm). Example 7 (30 mg, 28%) was obtained: HPLC: RT=3.756 min (Waters SunFire C$_{18}$ 3.5 g, 2.1×30 mm, 1 mL/min MeOH/H$_2$O/0.1% TFA, 4 min gradient, wavelength=254 nm); MS(ES): m/z=619.02 [M+1]$^+$; $^1$H NMR (400 MHz, methanol-d$_4$) δ 7.28-7.14 (m, 2H), 7.03 (d, J=7.9 Hz, 2H), 6.90-6.79 (m, 1H), 6.74-6.53 (m, 2H), 4.72 (dd, J=11.9, 7.3 Hz, 1H), 4.06-3.85 (m, 2H), 2.74-2.50 (m, 2H), 2.50-2.30 (m, 1H), 2.30-2.05 (m, 4H), 1.90-1.69 (m, 3H), 1.69-1.53 (m, 1H), 1.19-0.88 (m, 3H), 0.87-0.65 (m, 2H).

Example 8

(2R,3R)—N-((3S)-6-Cyano-4-oxo-1-(3-(trifluoromethyl)phenyl)-2,3,4,5-tetrahydro-1H-1,5-benzodiazepin-3-yl)-3-phenyl-2-(3,3,3-trifluoropropyl)succinamide (8)

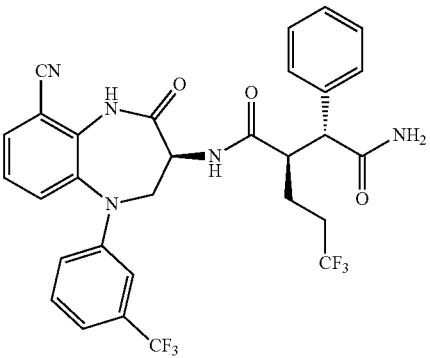

Example 8 was prepared from Intermediate B-24 (115.8 mg, 0.252 mmol) and Intermediate S-3 (87 mg, 0.252 mmol) according to the general procedure shown for Example 1. The product was purified by preparative SFC chromatography (Berger SFC MGII, Chiral IC 25×3 cm ID, 5 μm, 83/17 CO$_2$/MeOH, 85.0 mL/min, Detector Wavelength: 220 nm). Example 8 (42.2 mg, 26%) was obtained: HPLC: RT=1.01 min (CH$_3$CN/H$_2$O/0.05% TFA, BEH C$_{18}$ 2.1×50 mm 1.7μ, 1 min gradient, wavelength=254 nm); MS(ES): m/z=618 [M+1]$^+$; $^1$H NMR (400 MHz, DMSO-d$_6$) δ 10.46 (s, 1H), 8.28 (d, J=7.48 Hz, 1H), 7.79 (dd, J=1.54, 7.70 Hz, 1H), 7.68 (s, 1H), 7.47 (dd, J=1.43, 8.25 Hz, 1H), 7.43 (t, J=7.92 Hz, 1H), 7.33-7.39 (m, 3H), 7.18-7.32 (m, 4H), 6.93 (s, 1H), 6.69-6.75 (m, 2H), 4.28 (td, J=7.46, 11.28 Hz, 1H), 3.59 (d, J=11.22 Hz, 1H), 3.17-3.26 (m, 3H), 2.35-2.45 (m, 1H), 2.16-2.31 (m, 1H), 1.64-1.75 (m, 2H).

Example 9

(2R,3R)—N-((3S)-1-(3-Chloro-5-cyanophenyl)-6-(difluoromethyl)-4-oxo-2,3,4,5-tetrahydro-1H-1,5-benzodiazepin-3-yl)-3-phenyl-2-(3,3,3-trifluoropropyl)succinamide (9)

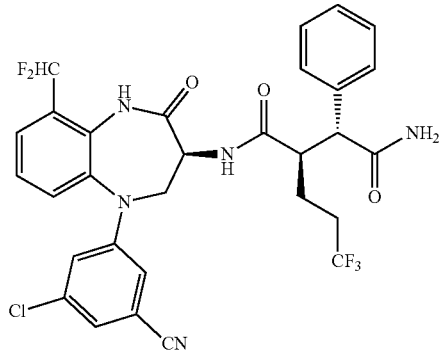

Example 9 was prepared from Intermediate B-21 (31.6 mg, 0.087 mmol) and Intermediate S-3 (31 mg, 0.090 mmol) according to the general procedure shown for Example 2. The product was purified by silica gel chromatography. Example 9 (17.3 mg, 30.2%) was obtained: HPLC: RT=3.0 min (MeCN/H$_2$O/10 mM NH$_4$OAc, Luna C$_{18}$ 2×50 mm, 4 min gradient, wavelength=254 nm); MS m/z=634/636 [M+1]$^+$; 632/634 [M−1]$^-$; $^1$H NMR (500 MHz, chloroform-d) δ 7.93 (s, 1H), 7.67-7.61 (m, 1H), 7.55-7.49 (m, 5H), 7.36 (t, J=7.9 Hz, 1H), 7.27 (s, 1H), 7.15-7.12 (m, 1H), 7.06 (d, J=6.9 Hz, 1H), 6.96-6.53 (m, 3H), 5.55 (d, J=4.0 Hz, 2H), 4.57 (dt, J=11.5, 6.7 Hz, 1H), 3.58-3.50 (m, 1H), 3.50-3.36 (m, 2H), 2.52-2.37 (m, 1H), 2.10-1.95 (m, 3H), 1.95-1.80 (m, 1H).

Example 10

(2R,3S)—N-((3S)-1-(3-Cyanophenyl)-6-(difluoromethyl)-4-oxo-2,3,4,5-tetrahydro-1H-1,5-benzodiazepin-3-yl)-2,3-bis(3,3,3-trifluoropropyl)succinamide (10)

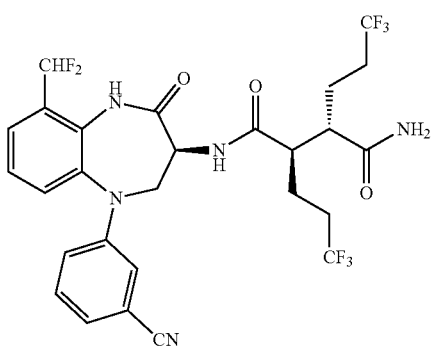

Example 10 was prepared from Intermediate B-19 (49 mg, 0.111 mmol) and a 40% mixture (60% of enantiomer) of Intermediate S-1 (45 mg, 0.123 mmol) according to the general procedure shown for Example 2. The product was purified by preparative SFC chromatography (Berger SFC MGII, CHIRALPAK® AD 25×2.1 cm ID, 5 μm, 90/10 CO$_2$/IPA, 60.0 mL/min, Detector Wavelength: 220 nm). Example 10 (7.9 mg, 11.5%) was obtained: HPLC: RT=2.86 min (MeCN/H$_2$O/10 mM NH$_4$OAc, Luna C$_{18}$ 2×50 mm, 4 min gradient, wavelength=254 nm); MS m/z=620 [M+1]$^+$; 618 [M−1]$^-$; $^1$H NMR (500 MHz, chloroform-d) δ 8.33 (br. s., 1H), 8.00 (d, J=6.1 Hz, 1H), 7.55 (d, J=7.5 Hz, 1H), 7.42-7.29 (m, 3H), 7.19 (d, J=7.8 Hz, 1H), 7.00-6.73 (m, 3H), 6.12 (br. s., 1H), 5.98 (br. s., 1H), 4.90 (dt, J=11.6, 6.7 Hz, 1H), 4.37 (dd, J=9.4, 6.6 Hz, 1H), 3.71 (dd, J=11.4, 9.6 Hz, 1H), 2.96-2.89 (m, 1H), 2.62-2.43 (m, 1H), 2.34-2.17 (m, 1H), 2.15-1.84 (m, 5H), 1.78-1.69 (m, 2H), 1.23 (d, J=6.1 Hz, 1H).

Example 11

(2R,3R)—N-((3S)-1-(3-Cyano-5-methylphenyl)-6-(difluoromethyl)-4-oxo-2,3,4,5-tetrahydro-1H-1,5-benzodiazepin-3-yl)-3-phenyl-2-(3,3,3-trifluoropropyl)succinamide (11)

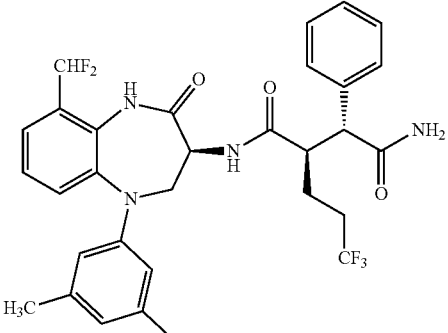

Example 11 was prepared from Intermediate B-22 (57 mg, 0.125 mmol) and Intermediate S-3 (44 mg, 0.127 mmol) according to the general procedure shown for Example 2. The product was purified by silica gel chromatography. Example 11 (28 mg, 35.1%) was obtained: HPLC: RT=2.92 min (MeCN/H$_2$O/10 mM NH$_4$OAc, Luna C$_{18}$ 2×50 mm, 4 min gradient, wavelength=254 nm); MS m/z=614 [M+1]$^+$; 612 [M−1]$^-$; 1HNMR: $^1$H NMR (500 MHz, chloroform-d) δ 7.81 (s, 1H), 7.63-7.56 (m, 1H), 7.54-7.49 (m, 4H), 7.47 (d, J=7.6 Hz, 1H), 7.35-7.29 (m, 1H), 7.27-7.21 (m, 1H), 7.01 (s, 1H), 6.94 (d, J=7.0 Hz, 1H), 6.79 (t, J=54.5 Hz, 1H), 6.59-6.47 (m, 2H), 5.53 (d, J=9.2 Hz, 2H), 4.57 (dt, J=11.5, 6.8 Hz, 1H), 3.55 (d, J=10.7 Hz, 1H), 3.43 (dd, J=9.9, 6.6 Hz, 1H), 3.38 (td, J=10.5, 3.2 Hz, 1H), 2.47 (dd, J=11.3, 10.1 Hz, 1H), 2.30 (s, 3H), 2.15-1.85 (m, 4H).

Example 12

(2R,3S)—N-((3S)-6-(Difluoromethyl)-1-(3-(difluoromethyl)phenyl)-4-oxo-2,3,4,5-tetrahydro-1H-1,5-benzodiazepin-3-yl)-2,3-bis(3,3,3-trifluoropropyl)succinamide

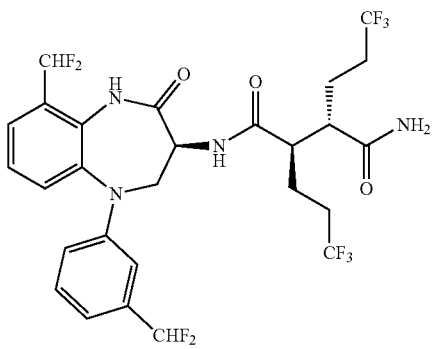

(12)

Example 12 was prepared from Intermediate B-20 (59.1 mg, 0.126 mmol) and a 40% mixture (60% of enantiomer) of Intermediate S-1 (46.3 mg, 0.126 mmol) according to the general procedure shown for Example 2. The product was purified by preparative SFC chromatography (Berger SFC MGII, CHIRALPAK® AD 25×2.1 cm ID, 5 μm, 90/10 $CO_2$/IPA, 60.0 mL/min, Detector Wavelength: 220 nm). Example 12 (4.9 mg, 6.0%) was obtained: RT=3.02 min (PHENOMENEX® Luna $C_{18}$, 50 mm×2 mm, 3μ, $CH_3CN/H_2O$/10 mM ammonium acetate, 4 min gradient, wavelength=254 nm); MS(ES): m/z=645[M+1]$^+$; m/z=643 [M−1]$^-$; $^1$H NMR (500 MHz, acetone-$d_6$) δ 9.04-8.67 (m, 1H), 7.89 (d, J=7.6 Hz, 1H), 7.65 (d, J=6.6 Hz, 1H), 7.51-7.33 (m, 3H), 7.23 (s, 1H), 7.15-7.06 (m, 1H), 6.99-6.65 (m, 3H), 6.59 (br. s., 1H), 4.92-4.80 (m, 1H), 4.23 (dd, J=9.8, 6.9 Hz, 1H), 3.94 (ddd, J=12.1, 9.9, 2.3 Hz, 1H), 2.78-2.70 (m, 1H), 2.67-2.57 (m, 1H), 2.47-2.34 (m, 1H), 2.30-2.16 (m, 3H), 1.90-1.62 (m, 4H).

Example 13

(2R,3R)—N-(1-(3-Cyano-5-fluorophenyl)-6-(difluoromethyl)-4-oxo-2,3,4,5-tetrahydro-1H-1,5-benzodiazepin-3-yl)-3-phenyl-2-(3,3,3-trifluoropropyl)succinamide

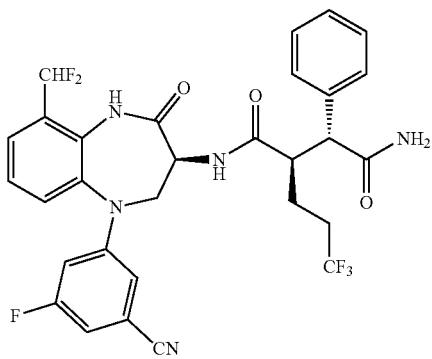

(13)

Example 13 was prepared from Intermediate B-23 (180 mg, 0.391 mmol) and Intermediate S-3 (126 mg, 0.364 mmol) according to the general procedure shown for Example 2. The product was purified by preparative HPLC (PHENOMENEX® Luna Axia 30×100 mm column from 35% Solvent B to 100% Solvent B over 12 min at 40 mL/min with detection at 254 nM. Solvent A was 10% MeOH/90% water with 0.1% TFA and Solvent B was 90% MeOH and 10% water with 0.1% TFA). Example 13 (73.7 mg, 30.9%) was obtained: HPLC: RT=2.88 min (PHENOMENEX® Luna $C_{18}$, 50 mm×2 mm, 3 g, $CH_3CN/H_2O$/10 mM ammonium acetate, 4 min gradient, wavelength=254 nm); MS(ES): m/z=618[M+1]$^+$; m/z=616 [M−1]$^-$; $^1$H NMR (400 MHz, chloroform-d) δ 7.95 (s, 1H), 7.61 (dd, J=8.8, 5.0 Hz, 1H), 7.55-7.45 (m, 5H), 7.45-7.28 (m, 2H), 7.14 (d, J=7.0 Hz, 1H), 7.01-6.60 (m, 2H), 6.49 (s, 1H), 6.39 (dt, J=11.3, 2.3 Hz, 1H), 6.04 (br. s., 1H), 5.69 (br. s., 1H), 4.58 (dt, J=11.5, 6.6 Hz, 1H), 3.64-3.52 (m, 1H), 3.50-3.29 (m, 2H), 2.55-2.40 (m, 1H), 2.13-1.82 (m, 5H).

Example 14

(2R,3S)-3-(Cyclopropylmethyl)-N-((3S)-6-fluoro-4-oxo-1-(3-(trifluoromethyl)phenyl)-2,3,4,5-tetrahydro-1H-1,5-benzodiazepin-3-yl)-2-(3,3,3-trifluoropropyl)succinamide

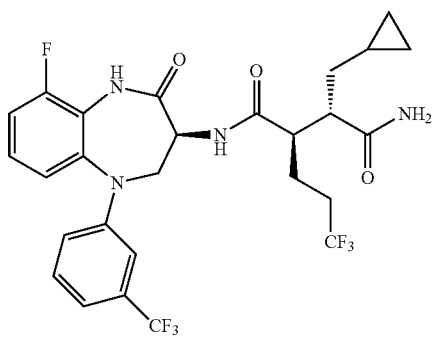

(14)

Example 14 was prepared from Intermediate B-25 (140 mg, 0.412 mmol) and Intermediate S-2 (160 mg, 0.494 mmol) according to the general procedure shown for Example 1. The product was purified by preparative SFC chromatography (Berger SFC MGII, Chiral IA 25×2 cm ID, 5 μm, 90/10 $CO_2$/MeOH, 50.0 mL/min, Detector Wavelength: 220 nm). Example 14 (64 mg, 26%) was obtained: HPLC: RT=3.48 min (MeOH/$H_2O$/0.1% TFA, Waters SunFire $C_{18}$ 2.1×30 mm, 2 min gradient, wavelength=220 nm); MS(ES): m/z=589 [M+1]$^+$; $^1$H NMR (400 MHz, DMSO-$d_6$) δ 10.05 (br. s., 1H), 8.54 (d, J=7.7 Hz, 1H), 7.60 (br. s., 1H), 7.44 (t, J=7.9 Hz, 1H), 7.32-7.26 (m, 2H), 7.20 (d, J=7.7 Hz, 1H), 7.08-7.03 (m, 1H), 6.99-6.91 (m, 3H), 4.62-4.53 (m, 1H), 4.12-4.03 (m, 2H), 3.97-3.88 (m, 1H), 2.46-2.38 (m, 2H), 2.15 (d, J=4.6 Hz, 1H), 1.65-1.53 (m, 2H), 1.50-1.38 (m, 1H), 1.00-0.79 (m, 1H), 0.55 (d, J=7.3 Hz, 1H), 0.38-0.26 (m, 2H), 0.01 (d, J=7.9 Hz, 1H), −0.13 (d, J=8.1 Hz, 1H).

Example 15

(2R,3S)-3-(Cyclopropylmethyl)-N-((3S)-1-(3-cyclopropylphenyl)-6-fluoro-4-oxo-2,3,4,5-tetrahydro-1H-1,5-benzodiazepin-3-yl)-2-(3,3,3-trifluoropropyl)succinamide (15)

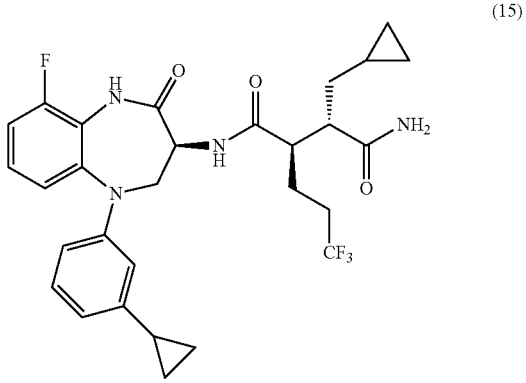 [SMILES: NC(=O)[C@@H](CC1CC1)[C@@H](CCC(F)(F)F)C(=O)N[C@H]1CN(c2cccc(C3CC3)c2)c2cccc(F)c2NC1=O]

Example 15 was prepared from Intermediate B-26 (96 mg, 0.309 mmol) and Intermediate S-2 (120 mg, 0.371 mmol) according to the general procedure shown for Example 1. The product was purified by preparative SFC chromatography (Berger SFC MGII, Chiral IC 25×3 cm ID, 5 μm, 80/20 $CO_2$/MeOH, 85.0 mL/min, Detector Wavelength: 220 nm). Example 15 (28 mg, 15%) was obtained: HPLC: RT=3.55 min (MeOH/$H_2O$/0.1% TFA, Waters SunFire $C_{18}$ 2.1×30 mm, 2 min gradient, wavelength=220 nm); MS(ES): m/z=561 [M+1]$^+$; $^1$H NMR (400 MHz, DMSO-$d_6$) δ 9.97 (s, 1H), 8.52 (d, J=7.7 Hz, 1H), 7.60 (br. s., 1H), 7.28-7.17 (m, 2H), 7.13-7.06 (m, 1H), 6.95 (dd, J=9.8, 3.0 Hz, 2H), 6.58 (d, J=7.7 Hz, 1H), 6.51-6.42 (m, 2H), 4.59-4.48 (m, 1H), 4.02-3.93 (m, 1H), 3.88-3.79 (m, 1H), 2.47-2.37 (m, 3H), 2.15 (d, J=4.6 Hz, 1H), 1.89-1.78 (m, 1H), 1.59 (d, J=7.5 Hz, 2H), 1.50-1.39 (m, 1H), 0.99-0.85 (m, 3H), 0.70-0.47 (m, 3H), 0.39-0.28 (m, 2H), 0.05-0.03 (m, 1H), −0.13 (d, J=9.0 Hz, 1H).

Example 16

(2R,3S)-3-(Cyclopropylmethyl)-N-((3S)-1-(3,4-dichlorophenyl)-6-fluoro-4-oxo-2,3,4,5-tetrahydro-1H-1,5-benzodiazepin-3-yl)-2-(3,3,3-trifluoropropyl)succinamide (16)

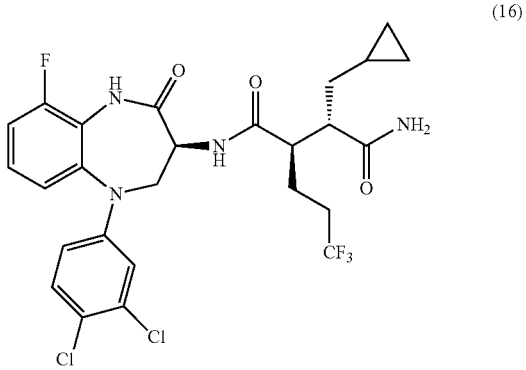 [SMILES: NC(=O)[C@@H](CC1CC1)[C@@H](CCC(F)(F)F)C(=O)N[C@H]1CN(c2ccc(Cl)c(Cl)c2)c2cccc(F)c2NC1=O]

Example 16 was prepared from Intermediate B-27 (56 mg, 0.166 mmol) and Intermediate S-2 (64 mg, 0.199 mmol) according to the general procedure shown for Example 1. The product was purified by preparative SFC chromatography (Berger SFC MGII, Chiral IC 25×3 cm ID, 5 μm, 80/20 $CO_2$/MeOH, 85.0 mL/min, Detector Wavelength: 220 nm). Example 16 (20 mg, 19%) was obtained: HPLC: RT=3.57 min (MeOH/$H_2O$/0.1% TFA, Waters SunFire $C_{18}$ 2.1×30 mm, 2 min gradient, wavelength=220 nm); MS(ES): m/z=589 [M+1]$^+$; $^1$H NMR (400 MHz, DMSO-$d_6$) δ 10.05 (br. s., 1H), 8.52 (d, J=7.7 Hz, 1H), 7.60 (br. s., 1H), 7.44 (d, J=9.0 Hz, 2H), 7.34-7.21 (m, 3H), 7.12-7.03 (m, 1H), 6.97 (br. s., 1H), 6.90 (d, J=2.6 Hz, 1H), 6.63 (dd, J=9.0, 2.9 Hz, 1H), 4.56 (dt, J=12.6, 7.2 Hz, 1H), 4.00 (dd, J=10.3, 6.8 Hz, 1H), 3.92-3.79 (m, 1H), 2.39 (br. s., 1H), 2.15 (dd, J=10.7, 5.8 Hz, 1H), 1.69-1.51 (m, 2H), 1.50-1.39 (m, 1H), 1.33-1.22 (m, 1H), 0.99-0.82 (m, 1H), 0.53 (br. s., 1H), 0.36-0.24 (m, 2H), 0.06-0.07 (m, 1H), −0.08-0.17 (m, 1H).

Example 17

(2R,3S)—N-((3S)-1-(3-Cyanophenyl)-6-fluoro-4-oxo-2,3,4,5-tetrahydro-1H-1,5-benzodiazepin-3-yl)-2,3-bis(3,3,3-trifluoropropyl)succinamide (17)

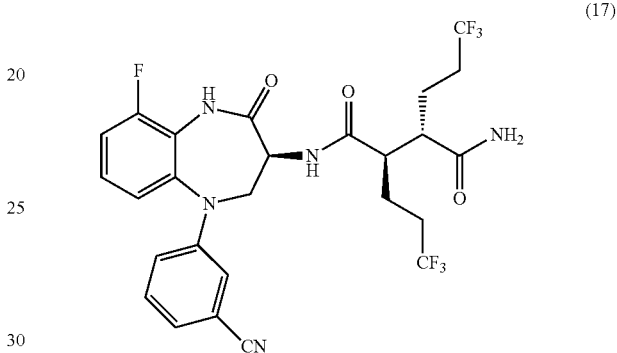

Example 17 was prepared from Intermediate B-28 (90 mg, 0.304 mmol) and Intermediate S-1 (122 mg, 0.334 mmol) according to the general procedure shown for Example 1. The product was purified by preparative SFC chromatography (Berger SFC MGIII, Chiral IC 25×3 cm ID, 5 μm, 92/8 $CO_2$/MeOH, 140.0 mL/min, Detector Wavelength: 220 nm). Example 17 (33 mg, 18%) was obtained: HPLC: RT=1.92 min (MeOH/$H_2O$/0.1% TFA, Waters SunFire $C_{18}$ 2.1×30 mm, 2 min gradient, wavelength=220 nm); MS(ES): m/z=588 [M+1]$^+$; $^1$H NMR (400 MHz, DMSO-$d_6$) δ 9.96 (br. s., 1H), 8.64 (d, J=7.7 Hz, 1H), 7.67 (s, 1H), 7.54 (d, J=8.1 Hz, 1H), 7.46-7.36 (m, 1H), 7.29 (d, J=7.3 Hz, 2H), 7.20 (d, J=7.3 Hz, 1H), 7.15 (br. s., 1H), 7.06 (s, 1H), 6.93 (dd, J=8.6, 2.0 Hz, 1H), 4.55 (dt, J=12.2, 7.3 Hz, 1H), 4.08 (q, J=5.3 Hz, 1H), 4.04-3.97 (m, 1H), 3.95-3.83 (m, 1H), 2.49-2.39 (m, 2H), 2.27-1.98 (m, 3H), 1.72-1.52 (m, 3H), 1.51-1.37 (m, 1H).

Example 18

(2R,3R)—N-((3S)-1-(3-Cyanophenyl)-6-fluoro-4-oxo-2,3,4,5-tetrahydro-1H-1,5-benzodiazepin-3-yl)-3-phenyl-2-(3,3,3-trifluoropropyl)succinamide (18)

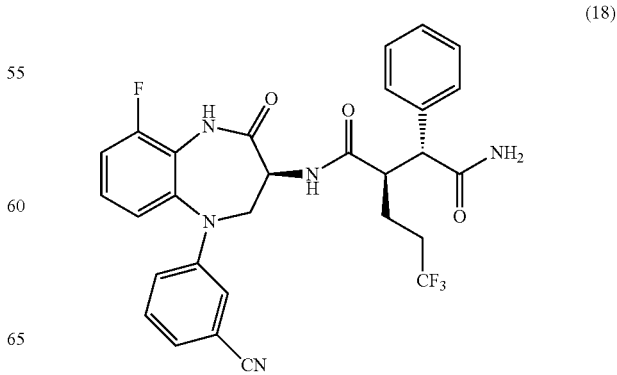

Example 18 was prepared from Intermediate B-28 (90 mg, 0.334 mmol) and Intermediate S-3 (116 mg, 0.334 mmol) according to the general procedure shown for Example 1. The product was purified by preparative SFC chromatography (Berger SFC MGIII, CHIRALPAK® AD-H 25×3 cm, 5 μm, $CO_2$/MeOH=85/15, 200 mL/min, Detector Wavelength: 220 nm). Example 18 (29 mg, 16%) was obtained: HPLC: RT=1.84 min (MeOH/$H_2O$/0.1% TFA, Waters SunFire $C_{18}$ 2.1×30 mm, 2 min gradient, wavelength=220 nm); MS(ES): m/z=568 [M+1]$^+$; $^1$H NMR (400 MHz, DMSO-$d_6$) δ 10.07 (s, 1H), 8.27 (d, J=7.7 Hz, 1H), 7.68 (br. s., 1H), 7.43-7.36 (m, 3H), 7.35-7.28 (m, 4H), 7.27-7.22 (m, 2H), 7.00-6.90 (m, 2H), 6.83-6.74 (m, 2H), 4.32 (dt, J=11.7, 7.2 Hz, 1H), 3.60 (d, J=11.4 Hz, 1H), 3.30-3.21 (m, 1H), 3.20-3.09 (m, 1H), 2.43-2.35 (m, 1H), 2.32-2.20 (m, 2H), 1.77-1.60 (m, 4H).

Example 19

(2R,3S)—N-((3S)-6-Chloro-1-(4-chlorophenyl)-4-oxo-2,3,4,5-tetrahydro-1H-1,5-benzodiazepin-3-yl)-3-(cyclopropylmethyl)-2-(3,3,3-trifluoropropyl)succinamide

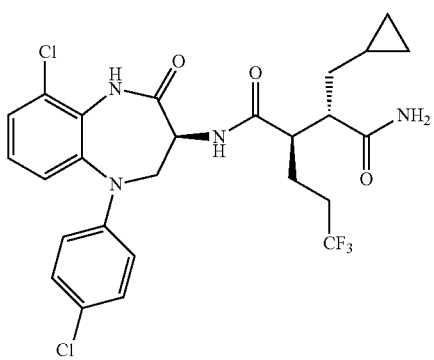

(19)

Example 19 was prepared from Intermediate B-30 (69 mg, 0.215 mmol) and Intermediate S-2 (77 mg, 0.237 mmol) according to the general procedure shown for Example 1. The product was purified by preparative SFC chromatography (Berger SFC MGII, CHIRALPAK® IC 25×3 cm, 5 μm, $CO_2$/MeOH=80/20, 85 mL/min, Detector Wavelength: 220 nm). Example 19 (7.4 mg, 6%) was obtained: HPLC: RT=2.09 min (MeOH/$H_2O$/0.1% TFA, Waters SunFire $C_{18}$ 2.1×30 mm, 2 min gradient, wavelength=220 nm); MS(ES): m/z=571 [M+1]$^+$; $^1$H NMR (400 MHz, DMSO-$d_6$) δ 9.89 (s, 1H), 8.53 (d, J=7.9 Hz, 1H), 7.60 (br. s., 1H), 7.48 (dd, J=7.9, 1.3 Hz, 1H), 7.33-7.21 (m, 3H), 7.16-7.09 (m, 1H), 6.97 (br. s., 1H), 6.70 (d, J=9.0 Hz, 2H), 4.55-4.41 (m, 1H), 4.00-3.91 (m, 1H), 3.89-3.77 (m, 1H), 2.55 (s, 1H), 2.42 (d, J=7.3 Hz, 2H), 2.14 (s, 1H), 1.58 (br. s., 2H), 1.44 (br. s., 1H), 1.00-0.79 (m, 1H), 0.52 (br. s., 1H), 0.41-0.22 (m, 2H), −0.01 (br. s., 1H), −0.12 (br. s., 1H).

Example 20

(2R,3S)—N-((3S)-6-Chloro-4-oxo-1-(3-(trifluoromethyl)phenyl)-2,3,4,5-tetrahydro-1H-1,5-benzodiazepin-3-yl)-2,3-bis(3,3,3-trifluoropropyl)succinamide

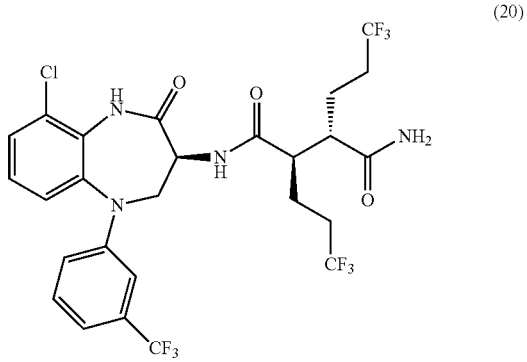 [SMILES: NC(=O)[C@@H](CCC(F)(F)F)[C@@H](CCC(F)(F)F)C(=O)N[C@H]1CN(c2cccc(C(F)(F)F)c2)c2cccc(Cl)c2NC1=O]

(20)

Example 20 was prepared from Intermediate B-32 (72 mg, 204 mmol) and Intermediate S-1 (82 mg, 0.224 mmol) according to the general procedure shown for Example 1. The product was purified by preparative SFC chromatography (Berger SFC MGII, Chiral ID 25×3 cm ID, 5 μm, 92/8 $CO_2$/MeOH, 85.0 mL/min, Detector Wavelength: 220 nm). Example 20 (44 mg, 32%) was obtained: HPLC: RT=2.15 min (MeOH/$H_2O$/0.1% TFA, Waters SunFire $C_{18}$ 2.1×30 mm, 2 min gradient, wavelength=220 nm); MS(ES): m/z=647 [M+1]$^+$; $^1$H NMR (400 MHz, DMSO-$d_6$) δ 9.96 (s, 1H), 8.66 (d, J=7.7 Hz, 1H), 7.67 (s, 1H), 7.54 (d, J=6.8 Hz, 1H), 7.44 (t, J=8.0 Hz, 1H), 7.35-7.26 (m, 1H), 7.24-7.17 (m, 2H), 6.97-6.82 (m, 2H), 4.60-4.50 (m, 1H), 4.09-4.00 (m, 1H), 3.95-3.86 (m, 1H), 2.48-2.40 (m, 2H), 2.25-2.09 (m, 3H), 1.68-1.53 (m, 3H), 1.52-1.40 (m, 1H).

Example 21

(2R,3S)—N-((3S)-6-Chloro-4-oxo-1-(3-(trifluoromethyl)phenyl)-2,3,4,5-tetrahydro-1H-1,5-benzodiazepin-3-yl)-3-(cyclopropylmethyl)-2-(3,3,3-trifluoropropyl)succinamide

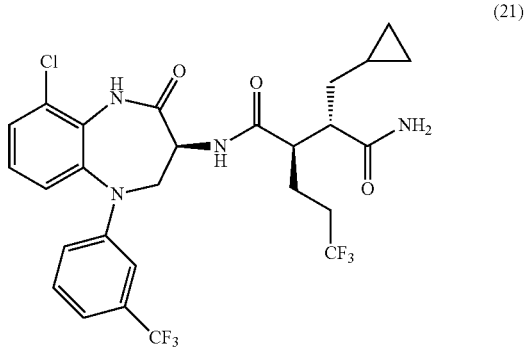 [SMILES: NC(=O)[C@@H](CC1CC1)[C@@H](CCC(F)(F)F)C(=O)N[C@H]1CN(c2cccc(C(F)(F)F)c2)c2cccc(Cl)c2NC1=O]

(21)

Example 21 was prepared from Intermediate B-32 (72 mg, 0.204 mmol) and Intermediate S-2 (73 mg, 0.224 mmol) according to the general procedure shown for Example 1. The product was purified by preparative SFC chromatography (Berger SFC MGII, Chiral ID 25×3 cm ID, 5 μm, 80/20 $CO_2$/MeOH, 85.0 mL/min, Detector Wavelength: 220 nm). Example 21 (43 mg, 34%) was obtained: HPLC: RT=2.14 min (MeOH/$H_2O$/0.1% TFA, Waters SunFire $C_{18}$ 2.1×30 mm, 2 min gradient, wavelength=220 nm); MS(ES): m/z=605 [M+1]$^+$; $^1$H NMR (400 MHz, DMSO-$d_6$) δ 9.91 (s, 1H), 8.52 (d, J=7.7 Hz, 1H), 7.60 (s, 1H), 7.53 (dd, J=8.1, 1.3 Hz, 1H), 7.44 (t, J=7.8 Hz, 1H), 7.30 (t, J=8.0 Hz, 1H), 7.20 (d, J=8.1 Hz, 2H), 7.01-6.87 (m, 3H), 4.55-4.44 (m, 1H), 4.09-4.00 (m, 1H), 3.97-3.88 (m, 1H), 2.46-2.35 (m, 3H), 2.24-2.09 (m, 1H), 1.59 (d, J=6.6 Hz, 2H), 1.50-1.39 (m, 1H), 0.98-0.89 (m, 1H), 0.54 (br. s., 1H), 0.39-0.27 (m, 2H), 0.05-0.04 (m, 1H), −0.13 (d, J=8.4 Hz, 1H).

Example 22

(2R,3R)—N-((3S)-6-Chloro-4-oxo-1-(3-(trifluoromethyl)phenyl)-2,3,4,5-tetrahydro-1H-1,5-benzodiazepin-3-yl)-3-phenyl-2-(3,3,3-trifluoropropyl)succinamide (22)

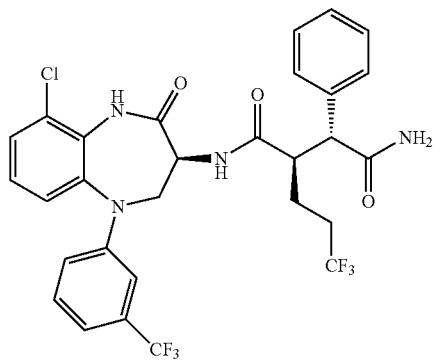

Example 22 was prepared from Intermediate B-32 (72 mg, 0.204 mmol) and Intermediate S-3 (78 mg, 0.224 mmol) according to the general procedure shown for Example 1. The product was purified by preparative SFC chromatography (Berger SFC MGII, Chiral IC 25×3 cm ID, 5 μm, 88/12 $CO_2$/MeOH, 85.0 mL/min, Detector Wavelength: 220 nm). Example 22 (42 mg, 32%) was obtained: HPLC: RT=2.11 min (MeOH/$H_2O$/0.1% TFA, Waters SunFire $C_{18}$ 2.1×30 mm, 2 min gradient, wavelength=220 nm); MS(ES): m/z=627 [M+1]$^+$; $^1$H NMR (400 MHz, DMSO-$d_6$) δ 9.91 (br. s., 1H), 8.28 (d, J=7.7 Hz, 1H), 7.68 (s, 1H), 7.51-7.40 (m, 2H), 7.39-7.34 (m, 2H), 7.33-7.21 (m, 4H), 7.21-7.08 (m, 2H), 6.94 (s, 1H), 6.76-6.68 (m, 2H), 4.22 (dt, J=11.8, 7.4 Hz, 1H), 3.59 (d, J=11.2 Hz, 1H), 3.29-3.12 (m, 3H), 2.45-2.35 (m, 1H), 2.32-2.16 (m, 1H), 1.77-1.62 (m, 2H).

Example 23

(2R,3S)—N-((3S)-6-Chloro-1-(3-cyanophenyl)-4-oxo-2,3,4,5-tetrahydro-1H-1,5-benzodiazepin-3-yl)-2,3-bis(3,3,3-trifluoropropyl)succinamide (23)

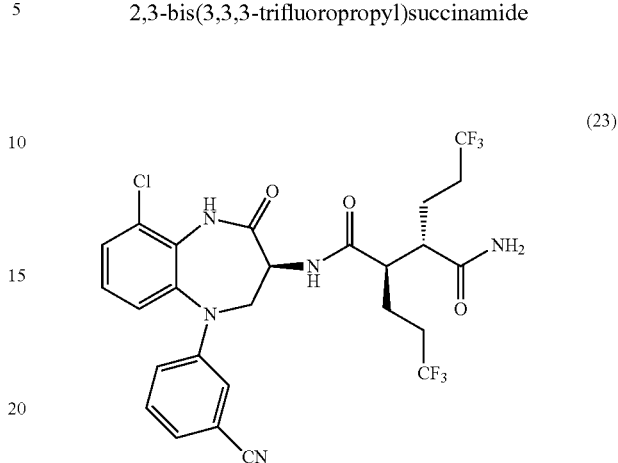

Example 23 was prepared from Intermediate B-33 (108 mg, 0.345 mmol) and Intermediate S-1 (139 mg, 0.380 mmol) according to the general procedure shown for Example 1. The product was purified by preparative SFC chromatography (Berger SFC MGIII, Chiral IC 25×3 cm ID, 5 μm, $CO_2$/MeOH=90/10, 120 mL/min, Detector Wavelength: 220 nm). Example 23 (32 mg, 15%) was obtained: HPLC: RT=1.93 min (MeOH/$H_2O$/0.1% TFA, Waters SunFire $C_{18}$ 2.1×30 mm, 2 min gradient, wavelength=220 nm); MS(ES): m/z=604 [M+1]$^+$; $^1$H NMR (400 MHz, DMSO-$d_6$) δ 10.11 (s, 1H), 8.66 (d, J=7.7 Hz, 1H), 7.66 (s, 1H), 7.49-7.36 (m, 1H), 7.34-7.24 (m, 3H), 7.19-6.89 (m, 4H), 4.63 (dt, J=12.4, 7.2 Hz, 1H), 4.14-4.00 (m, 2H), 3.96-3.79 (m, 1H), 2.48-2.39 (m, 2H), 2.26-2.01 (m, 3H), 1.71-1.53 (m, 3H), 1.52-1.38 (m, 1H).

Example 24

(2R,3R)—N-((3S)-6-Chloro-1-(3-cyanophenyl)-4-oxo-2,3,4,5-tetrahydro-1H-1,5-benzodiazepin-3-yl)-3-phenyl-2-(3,3,3-trifluoropropyl)succinamide (24)

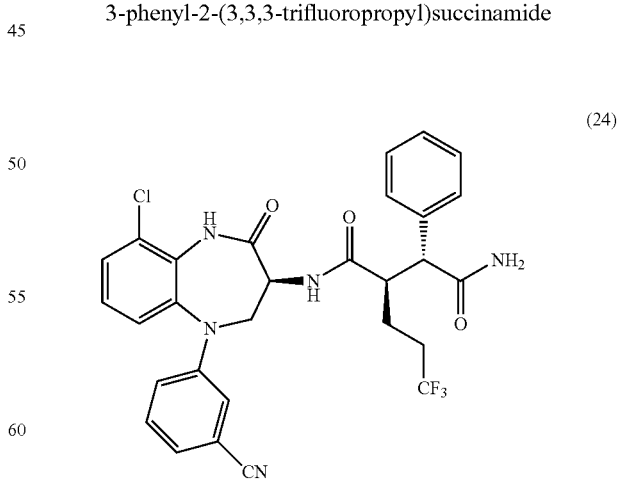

Example 24 was prepared from Intermediate B-33 (108 mg, 0.345 mmol) and Intermediate S-3 (131 mg, 0.380 mmol) according to the general procedure shown for Example 1. The product was purified by preparative SFC chromatography (Berger SFC MGIII, CHIRALPAK® AD-H 25×3 cm, 5 μm, CO$_2$/MeOH=75/25, 150 mL/min, Detector Wavelength: 220 nm). Example 24 (38 mg, 19%) was obtained: HPLC: RT=1.91 min (MeOH/H$_2$O/0.1% TFA, Waters SunFire C$_{18}$ 2.1×30 mm, 2 min gradient, wavelength=220 nm); MS(ES): m/z=584 [M+1]$^+$; $^1$H NMR (400 MHz, DMSO-d$_6$) δ 9.94 (s, 1H), 8.27 (d, J=7.5 Hz, 1H), 7.69 (s, 1H), 7.49 (dd, J=8.0, 1.2 Hz, 1H), 7.42-7.36 (m, 2H), 7.35-7.28 (m, 3H), 7.25 (t, J=8.0 Hz, 1H), 7.11 (d, J=7.0 Hz, 1H), 6.94 (br. s., 1H), 6.84-6.74 (m, 2H), 4.23 (dt, J=11.2, 7.5 Hz, 1H), 3.59 (d, J=11.2 Hz, 1H), 3.29-3.20 (m, 2H), 3.19-3.06 (m, 2H), 2.38 (br. s., 1H), 2.31-2.17 (m, 1H), 1.76-1.59 (m, 2H).

Example 25

(2R,3S)—N-((3S)-6-Chloro-1-(3-cyanophenyl)-4-oxo-2,3,4,5-tetrahydro-1H-1,5-benzodiazepin-3-yl)-3-(cyclopropylmethyl)-2-(3,3,3-trifluoropropyl)succinamide

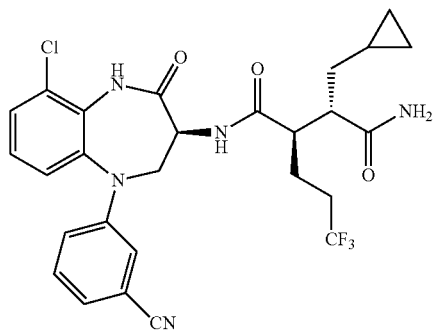

(25)

Example 25 was prepared from Intermediate B-33 (119 mg, 0.382 mmol) and Intermediate S-2 (136 mg, 0.420 mmol) according to the general procedure shown for Example 1. The product was purified by preparative SFC chromatography (Berger SFC MGII, Chiral IC 25×3 cm ID, 5 μm, 82/18 CO$_2$/MeOH, 85.0 mL/min, Detector Wavelength: 220 nm). Example 25 (30 mg, 13%) was obtained: HPLC: RT=1.93 min (MeOH/H$_2$O/0.1% TFA, Waters SunFire C$_{18}$ 2.1×30 mm, 2 min gradient, wavelength=220 nm); MS(ES): m/z=562 [M+1]$^+$; $^1$H NMR (400 MHz, DMSO-d$_6$) δ 9.92 (s, 1H), 8.51 (d, J=7.7 Hz, 1H), 7.60 (br. s., 1H), 7.54 (dd, J=8.1, 1.3 Hz, 1H), 7.46-7.36 (m, 1H), 7.34-7.26 (m, 2H), 7.18 (dd, J=8.0, 1.2 Hz, 1H), 7.09 (s, 1H), 7.01-6.89 (m, 2H), 4.51 (dt, J=12.3, 7.4 Hz, 1H), 4.04-3.96 (m, 1H), 3.95-3.84 (m, 1H), 2.46-2.38 (m, 1H), 2.23-2.07 (m, 1H), 1.67-1.53 (m, 2H), 1.51-1.34 (m, 1H), 1.25 (br. s., 1H), 1.01-0.80 (m, 2H), 0.61-0.45 (m, 1H), 0.40-0.26 (m, 2H), 0.04-0.05 (m, 1H), −0.13 (dt, J=5.3, 2.7 Hz, 1H).

Example 26

(2R,3S)—N-((3S)-6-Chloro-1-(2-cyanophenyl)-4-oxo-2,3,4,5-tetrahydro-1H-1,5-benzodiazepin-3-yl)-3-(cyclopropylmethyl)-2-(3,3,3-trifluoropropyl)succinamide

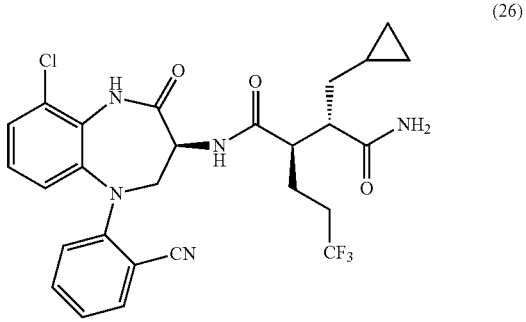 [SMILES: N#Cc1ccccc1N1C[C@H](NC(=O)[C@H](CCC(F)(F)F)[C@H](CC2CC2)C(N)=O)C(=O)Nc2c(Cl)cccc21]

(26)

Example 26 was prepared from Intermediate B-34 (76 mg, 0.242 mmol) and Intermediate S-2 (86 mg, 0.266 mmol) according to the general procedure shown for Example 1. The product was purified by preparative SFC chromatography (Berger SFC MGII, Chiral IC 25×3 cm ID, 5 μm, 80/20 CO$_2$/MeOH, 85.0 mL/min, Detector Wavelength: 220 nm). Example 26 (40 mg, 28%) was obtained: HPLC: RT=1.83 min (MeOH/H$_2$O/0.1% TFA, Waters SunFire C$_{18}$ 2.1×30 mm, 2 min gradient, wavelength=220 nm); MS(ES): m/z=562 [M+1]$^+$; $^1$H NMR (400 MHz, DMSO-d$_6$) δ 10.13 (s, 1H), 8.53 (d, J=7.9 Hz, 1H), 7.76-7.68 (m, 1H), 7.64-7.59 (m, 2H), 7.45 (dd, J=8.0, 1.2 Hz, 1H), 7.36 (d, J=8.4 Hz, 1H), 7.23-7.12 (m, 2H), 6.97 (br. s., 1H), 6.84 (dd, J=8.0, 1.2 Hz, 1H), 4.51 (dt, J=12.2, 7.5 Hz, 1H), 4.21 (dd, J=9.8, 7.4 Hz, 1H), 3.74 (dd, J=12.1, 9.9 Hz, 1H), 2.46-2.39 (m, 2H), 2.24-2.05 (m, 1H), 1.68-1.52 (m, 2H), 1.44 (ddd, J=13.3, 10.0, 6.4 Hz, 1H), 1.00-0.85 (m, 1H), 0.60-0.45 (m, 1H), 0.39-0.25 (m, 2H), 0.08-0.06 (m, 1H), −0.13 (dd, J=7.9, 3.1 Hz, 1H).

Example 27

(2R,3R)—N-((3S)-6-Chloro-1-(3-cyano-5-fluorophenyl)-4-oxo-2,3,4,5-tetrahydro-1H-1,5-benzodiazepin-3-yl)-3-phenyl-2-(3,3,3-trifluoropropyl)succinamide

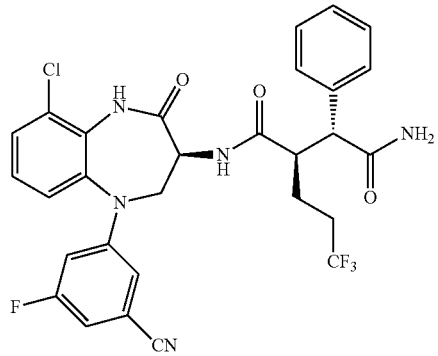

(27)

Example 27 was prepared from Intermediate B-35 (77 mg, 0.232 mmol) and Intermediate S-3 (88 mg, 0.255 mmol) according to the general procedure shown for Example 1. The product was purified by preparative SFC chromatography (Berger SFC MGII, Chiral IB 25×3 cm ID, 5 μm, 80/20 $CO_2$/MeOH, 85.0 mL/min, Detector Wavelength: 220 nm). Example 27 (23 mg, 16%) was obtained: HPLC: RT=1.97 min (MeOH/$H_2O$/0.1% TFA, Waters SunFire $C_{18}$ 2.1×30 mm, 2 min gradient, wavelength=220 nm); MS(ES): m/z=602 [M+1]$^+$; $^1$H NMR (400 MHz, DMSO-$d_6$) δ 9.95 (br. s., 1H), 8.24 (br. s., 1H), 7.68 (br. s., 1H), 7.52 (d, J=8.1 Hz, 1H), 7.43-7.14 (m, 8H), 6.94 (s, 1H), 6.64 (br. s., 1H), 6.53 (d, J=11.9 Hz, 1H), 4.30-4.15 (m, 1H), 3.59 (d, J=11.2 Hz, 1H), 3.28-3.11 (m, 3H), 2.37 (br. s., 1H), 2.32-2.20 (m, 1H), 1.76-1.63 (m, 3H).

Example 28

(2R,3S)—N-((3S)-6-Chloro-1-(3-cyano-5-fluorophenyl)-4-oxo-2,3,4,5-tetrahydro-1H-1,5-benzodiazepin-3-yl)-3-(cyclopropylmethyl)-2-(3,3,3-trifluoropropyl)succinamide

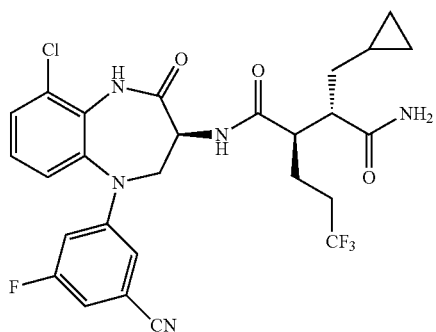

(28)

Example 28 was prepared from Intermediate B-35 (77 mg, 0.232 mmol) and Intermediate S-2 (83 mg, 0.255 mmol) according to the general procedure shown for Example 1. The product was purified by preparative SFC chromatography (Berger SFC MGII, Chiral IB 25×3 cm ID, 5 μm, 82/18 $CO_2$/MeOH, 85.0 mL/min, Detector Wavelength: 220 nm). Example 28 (37 mg, 28%) was obtained: HPLC: RT=1.97 min (MeOH/$H_2O$/0.1% TFA, Waters SunFire $C_{18}$ 2.1×30 mm, 2 min gradient, wavelength=220 nm); MS(ES): m/z=580 [M+1]$^+$; $^1$H NMR (400 MHz, DMSO-$d_6$) δ 9.93 (s, 1H), 8.49 (br. s., 1H), 7.66-7.52 (m, 2H), 7.40-7.16 (m, 3H), 7.02-6.84 (m, 2H), 6.76 (d, J=11.9 Hz, 1H), 4.52 (dt, J=12.2, 7.4 Hz, 1H), 4.07-3.86 (m, 2H), 2.48-2.38 (m, 2H), 2.24-2.05 (m, 1H), 1.67-1.53 (m, 2H), 1.51-1.36 (m, 1H), 1.33-1.20 (m, 1H), 0.94 (dd, J=11.0, 7.7 Hz, 1H), 0.53 (d, J=6.8 Hz, 1H), 0.39-0.24 (m, 2H), 0.05-0.06 (m, 1H), −0.06-0.22 (m, 1H).

Example 29

(2R,3S)—N-((3S)-6-Chloro-1-(3-cyclopropylphenyl)-4-oxo-2,3,4,5-tetrahydro-1H-1,5-benzodiazepin-3-yl)-3-(cyclopropylmethyl)-2-(3,3,3-trifluoropropyl)succinamide

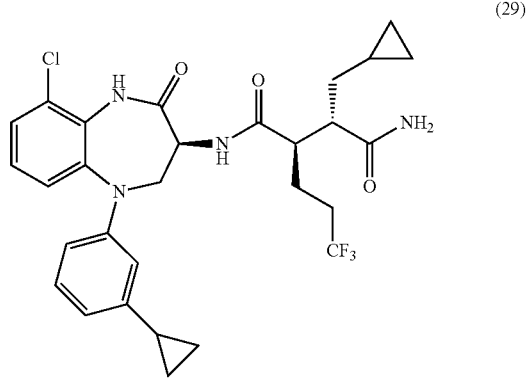

(29)

Example 29 was prepared from Intermediate B-12 (48.8 mg, 0.149 mmol) and Intermediate S-2 (48.4 mg, 0.149 mmol) according to the general procedure shown for Example 1. The product was purified by preparative SFC chromatography (Berger SFC MGII, PHENOMENEX® Lux Cellulose 2 25×3 cm ID, 5 μm, 80/20 $CO_2$/MeOH, 85.0 mL/min, Detector Wavelength: 220 nm). Example 29 (31.2 mg, 36%) was obtained: HPLC: RT=2.145 min (MeOH/$H_2O$/0.1% TFA, Waters SunFire $C_{18}$ 2.1×30 mm, 2 min gradient, wavelength=254 nm); MS(ES): m/z=577 [M+1]$^+$; $^1$H NMR (400 MHz, DMSO-$d_6$) δ 9.83 (s, 1H), 8.49 (d, J=7.70 Hz, 1H), 7.59 (br. s., 1H), 7.43 (dd, J=1.32, 7.92 Hz, 1H), 7.23 (t, J=8.14 Hz, 1H), 7.05-7.12 (m, 2H), 6.96 (s, 1H), 6.56 (d, J=7.70 Hz, 1H), 6.42-6.47 (m, 2H), 4.44 (td, J=7.24, 12.38 Hz, 1H), 3.90-3.97 (m, 1H), 3.83 (dd, J=10.23, 12.43 Hz, 1H), 2.37-2.44 (m, 2H), 2.05-2.24 (m, 1H), 1.78-1.88 (m, 1H), 1.58 (d, J=5.50 Hz, 2H), 1.38-1.49 (m, 1H), 0.85-0.97 (m, 3H), 0.59-0.67 (m, 1H), 0.48-0.58 (m, 2H), 0.26-0.37 (m, 2H), −0.05-0.03 (m, 1H), −0.14 (dd, J=2.86, 7.70 Hz, 1H).

Example 30

(2R,3R)—N-((3S)-6-Chloro-1-(3,4-dichlorophenyl)-4-oxo-2,3,4,5-tetrahydro-1H-1,5-benzodiazepin-3-yl)-3-phenyl-2-(3,3,3-trifluoropropyl)succinamide

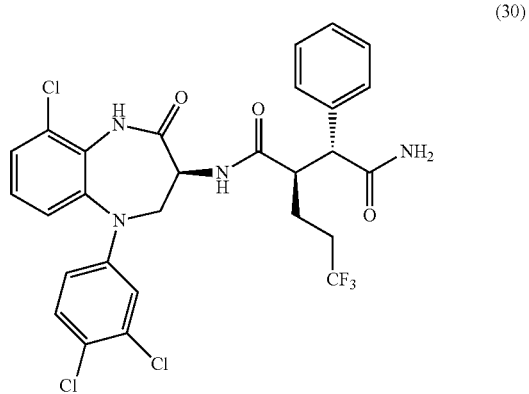 [SMILES: NC(=O)[C@@H](c1ccccc1)[C@@H](CCC(F)(F)F)C(=O)N[C@H]1CN(c2ccc(Cl)c(Cl)c2)c2cccc(Cl)c2NC1=O]

(30)

Example 30 was prepared from Intermediate B-31 (48.5 mg, 0.103 mmol) and Intermediate S-3 (36.3 mg, 0.105 mmol) according to the general procedure shown for Example 1. The product was purified by preparative SFC chromatography (Berger SFC MGII, CHIRALPAK® IC 25×3 cm ID, 5 μm, 80/20 CO$_2$/MeOH, 85.0 mL/min, Detector Wavelength: 220 nm). Example 30 (25.7 mg, 40%) was obtained: HPLC: RT=2.142 min (MeOH/H$_2$O/0.1% TFA, Waters SunFire C$_{18}$ 2.1×30 mm, 2 min gradient, wavelength=254 nm); MS(ES): m/z=627 [M+1]$^+$; $^1$H NMR (400 MHz, DMSO-d$_6$) δ 9.91 (br. s., 1H), 8.23 (d, J=7.70 Hz, 1H), 7.67 (br. s., 1H), 7.47 (dd, J=1.10, 7.92 Hz, 1H), 7.42 (d, J=9.02 Hz, 1H), 7.34-7.38 (m, 2H), 7.28-7.33 (m, 3H), 7.23 (t, J=8.14 Hz, 1H), 7.12 (d, J=7.04 Hz, 1H), 6.93 (s, 1H), 6.63 (d, J=2.64 Hz, 1H), 6.41 (dd, J=2.75, 8.91 Hz, 1H), 4.15-4.24 (m, 1H), 3.57 (d, J=11.44 Hz, 1H), 3.16-3.26 (m, 1H), 3.10 (d, J=9.02 Hz, 2H), 2.15-2.43 (m, 3H), 1.62-1.74 (m, 3H).

Example 31

(2R,3S)—N-((3S)-6-Chloro-1-(3-chlorophenyl)-4-oxo-2,3,4,5-tetrahydro-1H-1,5-benzodiazepin-3-yl)-2,3-bis(3,3,3-trifluoropropyl)succinamide

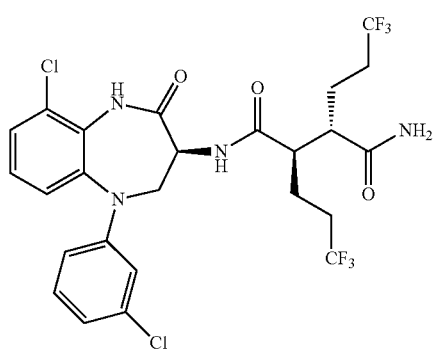

(31)

Example 31 was prepared from Intermediate B-29 (85.0 mg, 0.195 mmol) and Intermediate S-1 (73.6 mg, 0.201 mmol) according to the general procedure shown for Example 1. The product was purified by preparative SFC chromatography (Berger SFC MGII, CHIRALPAK® IC 25×3 cm ID, 5 μm, 85/15 CO$_2$/MeOH, 85.0 mL/min, Detector Wavelength: 220 nm). Example 31 (52.4 mg, 43%) was obtained: HPLC: RT=2.100 min (MeOH/H$_2$O/0.1% TFA, Waters SunFire C$_{18}$ 2.1×30 mm, 2 min gradient, wavelength=254 nm); MS(ES): m/z=613 [M+1]$^+$; $^1$H NMR (400 MHz, DMSO-d$_6$) δ 9.92 (br. s., 1H), 8.63 (d, J=7.70 Hz, 1H), 7.65 (s, 1H), 7.51 (dd, J=1.43, 8.03 Hz, 1H), 7.26-7.32 (m, 1H), 7.23 (t, J=8.14 Hz, 1H), 7.19 (dd, J=1.32, 7.92 Hz, 1H), 7.13 (br. s., 1H), 6.90 (dd, J=1.32, 7.92 Hz, 1H), 6.66 (t, J=2.09 Hz, 1H), 6.58 (dd, J=1.76, 8.36 Hz, 1H), 4.52 (td, J=7.29, 12.27 Hz, 1H), 3.93-4.00 (m, 1H), 3.82-3.90 (m, 1H), 2.39-2.47 (m, 2H), 2.02-2.27 (m, 4H), 1.51-1.68 (m, 4H), 1.37-1.49 (m, 1H).

Example 32

(2R,3S)—N-((3S)-6-Chloro-1-(3,4-dichlorophenyl)-4-oxo-2,3,4,5-tetrahydro-1H-1,5-benzodiazepin-3-yl)-2,3-bis(3,3,3-trifluoropropyl)succinamide

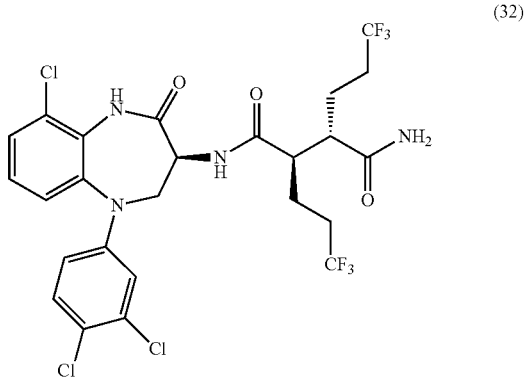 [SMILES: NC(=O)[C@@H](CCC(F)(F)F)[C@@H](CCC(F)(F)F)C(=O)N[C@H]1CN(c2ccc(Cl)c(Cl)c2)c2cccc(Cl)c2NC1=O]

(32)

Example 32 was prepared from Intermediate B-31 (101.9 mg, 0.217 mmol) and Intermediate S-1 (79.5 mg, 0.217 mmol) according to the general procedure shown for Example 1. The product was purified by preparative SFC chromatography (Berger SFC MGII, Chiral IC 25×3 cm ID, 5 μm, 90/10 CO$_2$/MeOH, 85.0 mL/min, Detector Wavelength: 220 nm). Example 32 (60.5 mg, 41%) was obtained: HPLC: RT=2.190 min (MeOH/H$_2$O/0.1% TFA, Waters SunFire C$_{18}$ 2.1×30 mm, 2 min gradient, wavelength=254 nm); MS(ES): m/z=647 [M+1]$^+$; $^1$H NMR (400 MHz, DMSO-d$_6$) δ 9.94 (s, 1H), 8.63 (d, J=7.70 Hz, 1H), 7.65 (s, 1H), 7.52 (dd, J=1.43, 8.03 Hz, 1H), 7.43 (d, J=9.02 Hz, 1H), 7.25-7.34 (m, 1H), 7.19-7.24 (m, 1H), 7.14 (s, 1H), 6.85 (d, J=2.86 Hz, 1H), 6.59 (dd, J=2.75, 8.91 Hz, 1H), 4.52 (td, J=7.26, 12.32 Hz, 1H), 3.93-4.02 (m, 1H), 3.81-3.90 (m, 1H), 2.38-2.48 (m, 2H), 2.01-2.26 (m, 3H), 1.50-1.68 (m, 3H), 1.38-1.49 (m, 1H).

Example 33

(2R,3S)—N-((3S)-6-Chloro-4-oxo-1-(2-pyridinyl)-2,3,4,5-tetrahydro-1H-1,5-benzodiazepin-3-yl)-2,3-bis(3,3,3-trifluoropropyl)succinamide

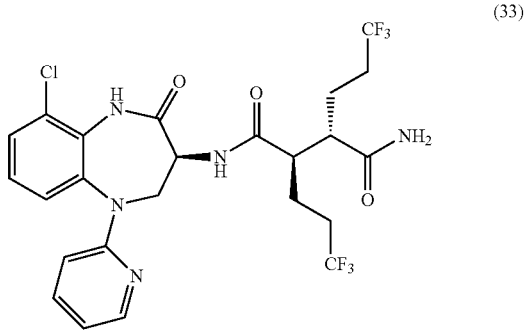 [SMILES: NC(=O)[C@@H](CCC(F)(F)F)[C@@H](CCC(F)(F)F)C(=O)N[C@H]1CN(c2ccccn2)c2cccc(Cl)c2NC1=O]

(33)

Example 33 was prepared from Intermediate B-36 (149.6 mg, 0.518 mmol) and Intermediate S-1 (189.0 mg, 0.516 mmol) according to the general procedure shown for Example 1. The product was purified by preparative SFC chromatography (Berger SFC MGIII, Chiral IC 25×3 cm ID, 5 μm, 88/12 CO$_2$/MeOH, 120.0 mL/min, Detector Wavelength: 220 nm). Example 33 (59.3 mg, 19%) was obtained: HPLC: RT=0.75 min (CH$_3$CN/H$_2$O/0.05% TFA, BEH C$_{18}$ 2.1×50 mm 1.7μ, 1 min gradient, wavelength=254 nm); MS(ES): m/z=580 [M+1]$^+$; $^1$H NMR (400 MHz, methanol-d$_4$) δ 8.17 (ddd, J=0.88, 1.76, 5.06 Hz, 1H), 7.53 (dd, J=2.20, 7.48 Hz, 1H), 7.46 (ddd, J=1.87, 7.04, 8.69 Hz, 1H), 7.24-7.35 (m, 2H), 6.79 (ddd, J=0.66, 5.06, 7.04 Hz, 1H), 6.37 (d, J=8.58 Hz, 1H), 4.77 (dd, J=6.38, 12.76 Hz, 1H), 4.68 (dd, J=10.78, 12.54 Hz, 1H), 3.93 (dd, J=6.38, 10.78 Hz, 1H), 2.61 (dt, J=4.18, 10.30 Hz, 1H), 2.52 (dt, J=3.52, 10.30 Hz, 1H), 2.31-2.47 (m, 1H), 2.01-2.26 (m, 3H), 1.66-1.85 (m, 3H), 1.53-1.65 (m, 1H).

Example 34

(2R,3R)—N-((3S)-6-Chloro-4-oxo-1-(6-(trifluoromethyl)-2-pyridinyl)-2,3,4,5-tetrahydro-1H-1,5-benzodiazepin-3-yl)-3-phenyl-2-(3,3,3-trifluoropropyl)succinamide

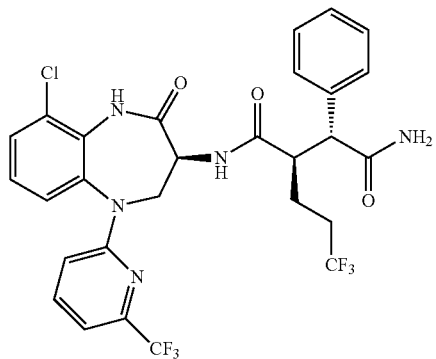

(34)

Example 34 was prepared from Intermediate B-13 (101.8 mg, 0.216 mmol) and Intermediate S-3 (81.4 mg, 0.235 mmol) according to the general procedure shown for Example 1. The product was purified by preparative SFC chromatography (Berger SFC MGII, Whelk-O R,R 25×3 cm ID, 5 μm, 82/18 CO$_2$/MeOH, 85.0 mL/min, Detector Wavelength: 220 nm). Example 34 (59.9 mg, 44%) was obtained: HPLC: RT=0.95 min (CH$_3$CN/H$_2$O/0.05% TFA, BEH C$_{18}$ 2.1×50 mm 1.7μ, 1 min gradient, wavelength=254 nm); MS(ES): m/z=628 [M+1]$^+$; $^1$H NMR (400 MHz, methanol-d$_4$) δ 7.49-7.60 (m, 2H), 7.35-7.42 (m, 2H), 7.19-7.33 (m, 5H), 7.12 (d, J=7.26 Hz, 1H), 6.41 (d, J=8.58 Hz, 1H), 4.28-4.43 (m, 2H), 3.60 (d, J=11.22 Hz, 1H), 3.20 (td, J=7.10, 11.11 Hz, 1H), 3.05 (dd, J=4.84, 10.12 Hz, 1H), 2.14-2.41 (m, 2H), 1.77-1.90 (m, 2H).

Example 35

(2R,3S)—N-((3S)-6-Chloro-4-oxo-1-(6-(trifluoromethyl)-2-pyridinyl)-2,3,4,5-tetrahydro-1H-1,5-benzodiazepin-3-yl)-2,3-bis(3,3,3-trifluoropropyl)succinamide

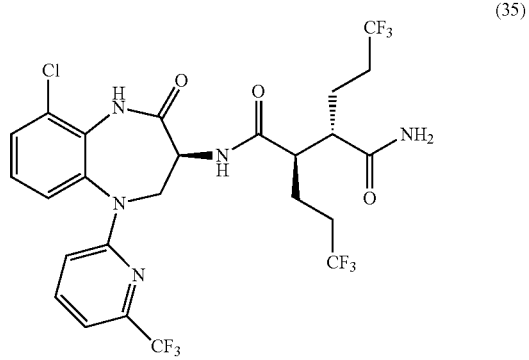

(35)

Example 35 was prepared from Intermediate B-13 (102.6 mg, 0.218 mmol) and Intermediate S-1 (81.6 mg, 0.223 mmol) according to the general procedure shown for Example 1. The product was purified by preparative SFC chromatography (Berger SFC MGII, CHIRALPAK® ID 25×3 cm ID, 5 μm, 88/12 CO$_2$/MeOH, 85.0 mL/min, Detector Wavelength: 220 nm). Example 35 (61.7 mg, 43%) was obtained: HPLC: RT=0.98 min (CH$_3$CN/H$_2$O/0.05% TFA, BEH C$_{18}$ 2.1×50 mm 1.7μ, 1 min gradient, wavelength=254 nm); MS(ES): m/z=648 [M+1]$^+$; $^1$H NMR (400 MHz, DMSO-d$_6$) δ 9.98 (s, 1H), 8.82 (d, J=7.48 Hz, 1H), 7.69 (t, J=7.92 Hz, 1H), 7.64 (dd, J=1.43, 8.03 Hz, 2H), 7.44 (dd, J=1.76, 8.14 Hz, 1H), 7.37 (t, J=8.10 Hz, 1H), 7.24 (d, J=7.26 Hz, 1H), 7.12 (s, 1H), 6.50 (d, J=8.80 Hz, 1H), 4.69-4.80 (m, 1H), 4.51-4.61 (m, 1H), 3.81 (dd, J=6.82, 11.66 Hz, 1H), 2.52-2.60 (m, 1H), 2.37-2.47 (m, 1H), 2.01-2.24 (m, 3H), 1.51-1.68 (m, 3H), 1.37-1.50 (m, 1H), 1.26 (d, J=19.15 Hz, 1H).

Example 36

(2R,3R)—N-((3S)-6-Chloro-4-oxo-1-(4-(trifluoromethyl)-2-pyridinyl)-2,3,4,5-tetrahydro-1H-1,5-benzodiazepin-3-yl)-3-phenyl-2-(3,3,3-trifluoropropyl)succinamide

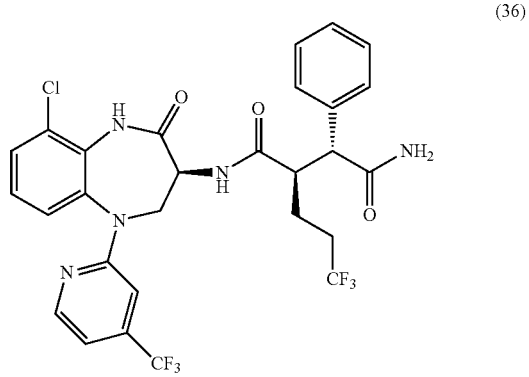

(36)

Example 36 was prepared from Intermediate B-37 (226.6 mg, 0.279 mmol) and Intermediate S-3 (100.0 mg, 0.289 mmol) according to the general procedure shown for Example 1. The product was purified by preparative SFC chromatography (Berger SFC MGII, PHENOMENEX® Lux Cellulose 4 25×3 cm ID, 5 μm, 83/17 $CO_2$/MeOH, 85.0 mL/min, Detector Wavelength: 220 nm). Example 36 (28.8 mg, 16%) was obtained: HPLC: RT=1.03 min ($CH_3CN/H_2O$/0.05% TFA, BEH $C_{18}$ 2.1×50 mm 1.7μ, 1 min gradient, wavelength=254 nm); MS(ES): m/z=628 [M+1]$^+$; $^1$H NMR (400 MHz, DMSO-$d_6$) δ 9.84 (s, 1H), 8.39-8.47 (m, 2H), 7.68 (br. s., 1H), 7.59 (dd, J=2.31, 7.15 Hz, 1H), 7.27-7.37 (m, 4H), 7.14-7.26 (m, 3H), 7.08 (d, J=5.06 Hz, 1H), 6.92 (s, 1H), 6.33 (s, 1H), 4.37-4.49 (m, 1H), 4.18 (td, J=7.29, 12.71 Hz, 1H), 3.59 (d, J=11.44 Hz, 1H), 3.12-3.22 (m, 2H), 2.37-2.48 (m, 1H), 2.16-2.31 (m, 1H), 1.59-1.75 (m, 2H).

Example 37

(2R,3S)—N-((3S)-7-Fluoro-4-oxo-1-phenyl-2,3,4,5-tetrahydro-1H-1,5-benzodiazepin-3-yl)-2,3-bis(3,3,3-trifluoropropyl)succinamide

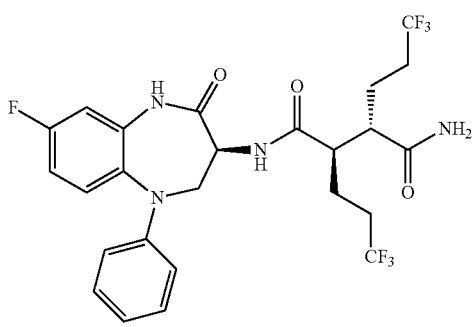

(37)

Example 37 was prepared from Intermediate B-38 (109 mg, 0.401 mmol) and Intermediate S-1 (162 mg, 0.441 mmol) according to the general procedure shown for Example 1. The product was purified by preparative SFC chromatography (Berger SFC MGII, Chiral IC 25×3 cm ID, 5 μm, 85/15 $CO_2$/MeOH, 85.0 mL/min, Detector Wavelength: 220 nm). Example 37 (21 mg, 14%) was obtained: HPLC: RT=2.06 min (MeOH/$H_2O$/0.1% TFA, Waters SunFire $C_{18}$ 2.1×30 mm, 2 min gradient, wavelength=220 nm); MS(ES): m/z=563 [M+1]$^+$; $^1$H NMR (400 MHz, DMSO-$d_6$) δ 10.15 (s, 1H), 8.69 (d, J=7.9 Hz, 1H), 7.65 (br. s., 1H), 7.28-7.11 (m, 4H), 7.10-6.97 (m, 2H), 6.84 (t, J=7.4 Hz, 1H), 6.64 (d, J=7.7 Hz, 2H), 4.61 (dt, J=12.4, 7.3 Hz, 1H), 4.00-3.91 (m, 1H), 3.90-3.78 (m, 1H), 2.48-2.38 (m, 2H), 2.26-1.99 (m, 3H), 1.73-1.53 (m, 4H), 1.47 (dt, J=7.0, 3.7 Hz, 1H).

Example 38

(2R,3S)—N-((3S)-7-Fluoro-4-oxo-1-(3-(trifluoromethyl)phenyl)-2,3,4,5-tetrahydro-1H-1,5-benzodiazepin-3-yl)-2,3-bis(3,3,3-trifluoropropyl)succinamide

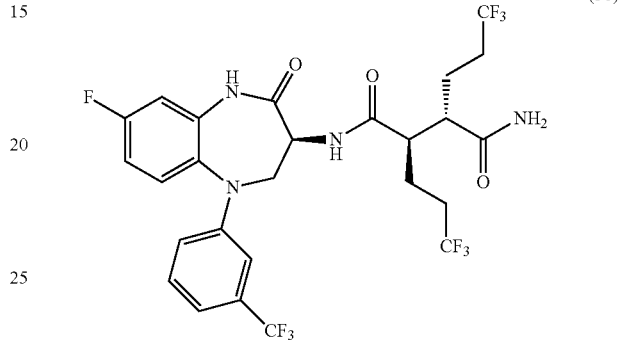

(38)

Example 38 was prepared from Intermediate B-39 (111 mg, 0.328 mmol) and Intermediate S-1 (132 mg, 0.361 mmol) according to the general procedure shown for Example 1. The product was purified by preparative SFC chromatography (Berger SFC MGII, Regis Whelk-O R,R 25×3 cm ID, 5 μm, 88/12 $CO_2$/MeOH, 85.0 mL/min, Detector Wavelength: 220 nm). Example 38 (21 mg, 9%) was obtained: HPLC: RT=2.15 min (MeOH/$H_2O$/0.1% TFA, Waters SunFire $C_{18}$ 2.1×30 mm, 2 min gradient, wavelength=220 nm); MS(ES): m/z=631 [M+1]$^+$; $^1$H NMR (400 MHz, DMSO-$d_6$) δ 10.19 (s, 1H), 8.68 (d, J=7.9 Hz, 1H), 7.66 (br. s., 1H), 7.41 (t, J=8.0 Hz, 1H), 7.28 (dd, J=8.9, 5.8 Hz, 1H), 7.19-7.02 (m, 4H), 6.91-6.77 (m, 2H), 4.63 (dt, J=12.3, 7.3 Hz, 1H), 4.03 (dd, J=10.3, 6.8 Hz, 1H), 3.97-3.85 (m, 1H), 2.47-2.41 (m, 1H), 2.25-1.97 (m, 4H), 1.71-1.53 (m, 4H), 1.52-1.42 (m, 1H).

Comparative Compounds 39 to 42

Comparative Compounds 39 to 42 can be prepared according to the procedures described in U.S. Pat. No. 7,053,084 for Examples 8, 12a, 38, and 45a, respectively.

| Comparative Compound | U.S. Pat. No. 7,053,084 | Structure |
|---|---|---|
| 39 | Ex. 8 | (structure shown) |

-continued

| Comparative Compound | U.S. Pat. No. 7,053,084 | Structure |
|---|---|---|
| 40 | Ex. 12a | 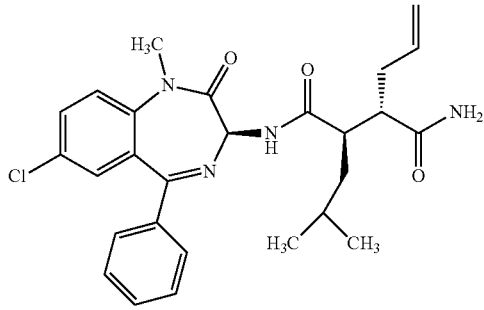 [SMILES: C=CC[C@H](C(N)=O)[C@@H](CC(C)C)C(=O)N[C@H]1N=C(c2ccccc2)c2cc(Cl)ccc2N(C)C1=O] |
| 41 | Ex. 38 | 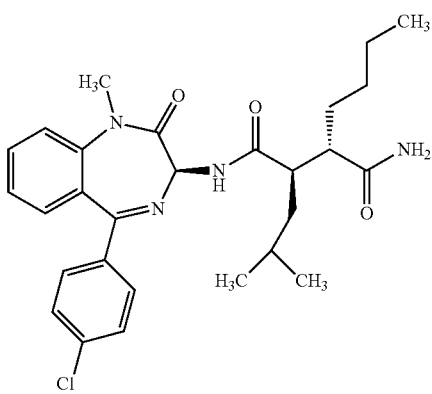 [SMILES: CCCC[C@H](C(N)=O)[C@@H](CC(C)C)C(=O)N[C@H]1N=C(c2ccc(Cl)cc2)c2ccccc2N(C)C1=O] |
| 42 | Ex. 45a | 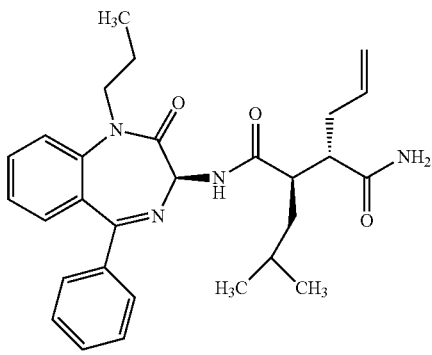 [SMILES: C=CC[C@H](C(N)=O)[C@@H](CC(C)C)C(=O)N[C@H]1N=C(c2ccccc2)c2ccccc2N(CCC)C1=O] |

Biological Assays

The pharmacological properties of the compounds of this invention may be confirmed by a number of biological assays. The exemplified biological assays, which follow, have been carried out with compounds of the invention.

Notch-CBF1 Transactivation Assay

The Notch-CBF1 (C-promoter binding factor I) cell based transactivation assay is based on the ability of the released Notch intracellular domain fragments (NICDs) to function as transcription factors in conjunction with CBF1 and other nuclear factors. Luciferase assays were used to measure the antagonism of Notch-CBF1 transcriptional activity. HeLa cervical cancer cells are transiently co-transfected with pCDNA3.1/Hygro plasmids containing truncated Notch 1, Notch 2, Notch 3, or Notch 4 receptors and a PGL3 luciferase reporter vector containing 4 copies of CBF1 binding site. The cells were then tested for Notch-CBF1 activity in the absence or presence of test compounds. HeLa cells, maintained in DMEM (high glucose with HEPES), 1× glutamine/penicillin/streptomycin and 10% Fetal Bovine serum, were transiently transfected in a T175 Flask ($4.5 \times 10^6$ cells/flask) using the Monster Transfection Kit (Minis #MIR2906) according to manufacturers specifications. Table 12 denotes respective DNA quantity for the transfections.

TABLE 12

|  | DNA (μg) | CBF1 (μg) | Vector (μg) | Total DNA (μg) |
|---|---|---|---|---|
| human Notch 1 | 6 | 14.4 | 15.6 | 36.0 |
| human Notch 2 | 2 | 14.4 | 19.6 | 36.0 |
| human Notch 3 | 0.3 | 14.4 | 21.3 | 36.0 |
| human Notch 4 | 4 | 14.4 | 17.6 | 36.0 |

Six hours post-transfection, cells were trypsinized and plated into a 384-well black Poly-D-lysine coated tissue culture plate at a density of $5 \times 10^3$ cells/well in 95 μL assay media (DMEM (high glucose with HEPES), 1× glutamine/penicillin/streptomycin, 0.0125% BSA, 1× non-essential amino acids). Assay media (5 μL) containing test compounds in final concentrations ranging from 5 μM to 8.4×10$^{-5}$ μM (3 fold serial dilutions) were added to the cells and the cell plates were then incubated for 18 hours at 37° C. and 5% $CO_2$. Control wells contained DMSO vehicle (total counts) or 0.5 μM of an in-house small molecule inhibitor (background counts). Duplicates were used for each sample. Luciferase activity was measured after a 20-minute incubation with 50 μl STEADY-GLO® luciferase reagents according to manufacturer's specifications (Promega, Cat. #E2550) and analyzed by Envision plate reader (PerkinElmer, Boston, Mass.).

The antagonist effect of compounds was expressed as 100× [1−(average sample−average background)/(average total−average background)] where sample is the luciferase activity in the presence of test compound, background is equal to the luciferase activity in the presence of the small molecule inhibitor control and the total is signal induced in DMSO wells. Data was plotted using a four parameter logistic fit equation and the $IC_{50}$ value was defined as the concentration of compound that inhibited 50% of the luciferase activity.

Table 13 below lists the Notch 1 and Notch 3 $IC_{50}$ values for Examples 1-38 of this invention and Comparative Compounds 39-42 measured in the Notch-CBF1 Transactivation Assay hereinabove. In some instances, the value is an average of multiple experiments where N is the number of experiments conducted. The compounds of the present invention, as exemplified by the Examples 1-38 showed Notch 1 values of 22.5 nM or less and Notch 3 $IC_{50}$ values of 46.2 nM or less.

TABLE 13

| Example | Notch 1 $IC_{50}$ (nM) | N | Notch 3 $IC_{50}$ (nM) | N |
| --- | --- | --- | --- | --- |
| 1 | 3.4 | 2 | 4.3 | 2 |
| 2 | 3.8 | 2 | 4.0 | 2 |
| 3 | 3.8 | 2 | 2.5 | 3 |
| 4 | 17.4 | 2 | 7.9 | 3 |
| 5 | 2.2 | 3 | 5.7 | 2 |
| 6 | 13.9 | 2 | 8.3 | 2 |
| 7 | 3.4 | 3 | 4.6 | 3 |
| 8 | 1.9 | 2 | 2.2 | 2 |
| 9 | 3.2 | 2 | 3.9 | 2 |
| 10 | 12.0 | 2 | 15.2 | 2 |
| 11 | 2.8 | 3 | 4.0 | 3 |
| 12 | 2.3 | 2 | 7.6 | 2 |
| 13 | 2.7 | 2 | 2.5 | 1 |
| 14 | 1.5 | 2 | 2.9 | 2 |
| 15 | 1.9 | 2 | 7.2 | 1 |
| 16 | 1.6 | 4 | 8.5 | 4 |
| 17 | 17.6 | 3 | 14.8 | 3 |
| 18 | 1.9 | 2 | 1.3 | 2 |
| 19 | 2.9 | 2 | 8.4 | 2 |
| 20 | 1.0 | 4 | 0.8 | 2 |
| 21 | 1.7 | 2 | 1.0 | 2 |
| 22 | 1.3 | 2 | 2.2 | 2 |
| 23 | 11.6 | 4 | 8.0 | 4 |
| 24 | 1.8 | 3 | 2.3 | 1 |
| 25 | 14.6 | 3 | 12.6 | 2 |
| 26 | 22.5 | 3 | 46.2 | 3 |
| 27 | 5.9 | 2 | 7.9 | 2 |
| 28 | 9.3 | 3 | 14.9 | 2 |
| 29 | 5.3 | 3 | 3.8 | 3 |
| 30 | 3.3 | 3 | 4.7 | 3 |
| 31 | 2.3 | 3 | 4.4 | 3 |
| 32 | 3.8 | 2 | 4.7 | 2 |
| 33 | 9.6 | 3 | 14.1 | 2 |
| 34 | 1.5 | 2 | 2.9 | 2 |
| 35 | 1.9 | 2 | 2.1 | 2 |
| 36 | 9.5 | 4 | 6.5 | 3 |
| 37 | 1.9 | 2 | 1.3 | 2 |
| 38 | 1.8 | 3 | 2.4 | 3 |

TABLE 13-continued

| Example | Notch 1 $IC_{50}$ (nM) | N | Notch 3 $IC_{50}$ (nM) | N |
| --- | --- | --- | --- | --- |
| Comparative Compound 39 | 64 | 1 | 48 | 1 |
| Comparative Compound 40 | 42 | 2 | 75 | 2 |
| Comparative Compound 41 | 5.1 | 3 | 13 | 4 |
| Comparative Compound 42 | 12 | 1 | 12 | 1 |

High Throughput (HT) Metabolic Stability Panel

Compounds administered parenterally enter the blood stream and undergo one or more passes through the liver. Compounds that are not readily metabolized by the liver can be administered at therapeutically effective plasma levels for therapeutically effective periods of time.

Orally administered compounds typically are absorbed through the intestinal walls into the blood stream and undergo a first pass through the liver. Compounds that are not readily metabolized in this first pass through the liver can be distributed to other areas of the body in therapeutically effective amounts.

The metabolic stability assay evaluated CYP-mediated metabolic stability in vitro using human, rat, mouse, dog, and/or monkey microsomes after a ten-minute incubation. Each compound was tested in duplicate.

The results of these assays were expressed as the fraction of parent compound remaining in the reaction mixture after a ten-minute incubation (Percent Remaining) In general, these results were used to evaluate only the extent of CYP-mediated, or NADPH-dependent, metabolism of the test compound. When the compound was significantly metabolized (<40-50% remaining), this indicated high clearance of the compound in vivo due to CYP-mediated metabolism. However, if the compound demonstrated moderate (50-80%) or low (>85%) metabolism in these in vitro assays, high clearance was still possible in vivo via other metabolism and elimination pathways.

The percent remaining results of these assays was predictive of compound clearance in vivo, assuming that CYP-mediated metabolism was a predominant elimination pathway. In different microsomal species, the ranges of results were approximately as shown in Table 14.

TABLE 14

| Metabolic Stability - Result Interpretation Guidelines | | | | | |
| --- | --- | --- | --- | --- | --- |
| CYP-Mediated | Percent Remaining after 10 minutes | | | | |
| Clearance | Human | Rat | Mouse | Dog | Monkey |
| Low | >90 | >85 | >85 | >90 | >85 |
| Medium | 60-90 | 40-85 | 50-85 | 55-90 | 40-85 |
| High | <60 | <40 | <50 | <55 | <40 |

Methods and Materials
Incubation with Liver Microsomes

Test compound was received as a 3.5 mM stock solution in 100 percent DMSO. The test compound was diluted to create a 50 μM acetonitrile (ACN) solution containing 1.4% DMSO, which was then used as a 100× stock for incubation with microsomes. Each compound was tested in duplicate separately in each of three species in the Metabolic Stability-Human, Rat, and Mouse assay suite or as individual species in the Metabolic Stability-Dog or Metabolic Stability-Monkey suites. Compound, NADPH, and liver microsome solutions were combined for incubation in three steps:

1. 152 μl of liver microsome suspension, protein concentration of 1.1 mg/ml in 100 mM NaP$_i$, pH 7.4, 5 mM MgCl$_2$ buffer, was pre-warmed at 37° C.

2. 1.7 μl of 50 μM compound (98.6% ACN, 1.4% DMSO) was added to the same tube and pre-incubated at 37° C. for 5 minutes.

3. The reaction was initiated by the addition of 17 μl of pre-warmed 10 mM NADPH solution in 100 mM NaP$_i$, pH 7.4.

The reaction components were mixed well, and 75 μl of the reaction mixture was immediately transferred into 150 μl quench/stop solution (zero-time point, T$_0$). Reactions were incubated at 37° C. for 10 minutes and then an additional 75 μl aliquot was transferred into 150 μl quench solution. Acetonitrile containing 100 μM DMN (a UV standard for injection quality control), was used as the quench solution to terminate metabolic reactions.

Quenched mixtures were centrifuged at 1500 rpm (~500× g) in an ALLEGRA® X-12 centrifuge, SX4750 rotor (Beckman Coulter Inc., Fullerton, Calif.) for fifteen minutes to pellet denatured microsomes. A volume of 90 μl of supernatant extract, containing the mixture of parent compound and its metabolites, was then transferred to a separate 96-well plate for UV-LC/MS-MS analysis to determine the percent of parent compound that remained in the mixture.

TABLE 15

Metabolic Stability Assay - Reaction Components

| Reaction Components | Final Concentration in the Metabolic Stability Assay |
|---|---|
| Compound (Substrate) | 0.5 μM |
| NaPi Buffer, pH 7.4 | 100 mM |
| DMSO | 0.014% |
| Acetonitrile | 0.986% |
| Microsomes (human, rat, mouse) (BD/Gentest) | 1 mg/ml protein |
| NADPH | 1.0 mM |
| MgCl$_2$ | 5.0 mM |
| 37° C. Incubation time | 0 minutes and 10 minutes |
| Quench/Stop Solution (ACN + 100 μM DMN) | 150 μl |
| Sample of Reaction | 75 μl |
| Sedimentation of Denatured Microsomes | 15 minutes |
| UV-LC/MS analysis of supernatant | 0.17 μM |

Sample Analysis—Instrumentation

HPLC: Pump—Thermo Surveyor; Autosampler—CTC/LEAP HTS; UV detector—Thermo Surveyor PDA plus; Column—VARIAN® C18, 3 μm, 2×20 mm with a 0.5 μm in-line filter; Mobile Phase for structural integrity pre-analysis: (A) 98% water, 2% acetonitrile with 10 mM ammonium acetate; (B) 10% water, 90% acetonitrile with 10 mM ammonium acetate; Mobile Phase for reaction sample analysis: (A) 98% water, 2% acetonitrile with 0.1% formic acid; (B) 2% water, 98% acetonitrile with 0.1% formic acid; (C) 0.1% ammonium hydroxide in water; (D) 0.1% ammonium hydroxide in acetonitrile.

Mass Spectrometer: Thermo TSQ QUANTUM® Ultra triple-quadrupole mass spectrometer.

Sample Analysis—Structural Integrity Pre-Analysis.

The Metabolic Stability structural integrity pre-analysis was used to assess the purity of compounds being assayed. Compounds were received in 96-well plates as 57 μl of a 3.5 mM DMSO solution. The 3.5 mM compound DMSO stock solutions were diluted 18-fold with a solution containing equal volumes of acetonitrile, isopropanol, and MilliQ-H$_2$O. The resulting solutions (200 μM) were analyzed for structural integrity by LC-UV/MS on a Thermo LCQ Deca XP Plus ion trap mass spectrometer, using a Waters XBridge C18, 5 μm, 2×50 mm column with a Waters Sentry 2.1 mm guard column, and the LC conditions described in the table below, with a 5 μl injection and a flow rate of 1 ml/min. The acquired data reflected purity by UV absorbance at 220 nm. Only results for those compounds with purity greater than 50% were reported.

TABLE 16

Metabolic Stability - Structural Integrity Gradient

| Gradient Time (min) | A % | B % |
|---|---|---|
| 0.00 | 100 | 0 |
| 4.00 | 0 | 100 |
| 5.00 | 0 | 100 |
| 5.10 | 100 | 0 |
| 6.00 | 100 | 0 |

Sample Analysis—Incubated Samples

MS/MS condition optimization was conducted on a Thermo TSQ QUANTUM® triple-quadrupole mass spectrometer equipped with a heated-electrospray (H-ESI) source by automated infusion to obtain the SRM transitions and their corresponding collision energy values. Compound solutions at a concentration of 20 μM in 1:1 methanol:water were infused at a flow rate of 90 μL/min, then combined with the mobile phase at a flow rate of 50 μL/min before being introduced into the source. All compounds were optimized first using mobile phase A and B (50% A and 50% B), and if necessary, using mobile phase C and D (also with a 50:50 composition). The optimized parameters, including polarity, SRM transition and collision energy, were stored in a MICROSOFT ACCESS® database.

The mass spectrometric conditions obtained from automated infusion were used to analyze incubation samples from the Metabolic Stability assay. The injection volume was 5 μl and the flow rate was 0.8 ml/min. The gradient used was shown in the table below. All samples were injected with the gradient using mobile phase A and B first. If necessary (for instance, for chromatographic reasons), samples were re-injected with the same gradient, but using mobile phase C and D. All LC-MS/MS analysis parameters were captured electronically in the raw data files.

TABLE 17

Metabolic Stability - Sample Analysis Gradient

| Gradient Time (min) | A % (or C %) | B % (or D %) |
|---|---|---|
| 0.00 | 95 | 5 |
| 0.20 | 95 | 5 |
| 0.30 | 0 | 100 |
| 1.05 | 0 | 100 |
| 1.10 | 95 | 5 |
| 1.50 | 95 | 5 |

Data Analysis

Peak integration was performed with the XCALIBUR® software. The percent remaining calculation was performed by comparing the LC-MS/MS peak areas from the T$_{10 minute}$ samples to those from the T$_{0 minute}$ samples for each compound.

Quality Control

A set of three compounds was tested along with the test compound in each assay plate. Data was accepted and uploaded only if the results for these control compounds fall into the expected ranges shown below.

TABLE 18

Metabolic Stability Assay - Control Compound
Values by Microsome Species

| | Average Percent Remaining ± SD | | | | |
|---|---|---|---|---|---|
| Compound | Human | Rat | Mouse | Dog | Monkey |
| Nefazodone | 0.4 ± 0.4 | 0.7 ± 0.6 | 0.4 ± 0.3 | 0.4 ± 0.4 | 0.6 ± 0.5 |
| Verapamil | 13.3 ± 3.5 | 4.4 ± 2.1 | 13.0 ± 4.2 | 5.6 ± 1.8 | 0.5 ± 0.5 |
| Carbamezepine | 96 ± 6 | 84 ± 9 | 90 ± 10 | 81 ± 7 | 89 ± 13 |

SD = Standard Deviation

Metabolic Stability Half-Life Panel

The rate of metabolism and half-life determined in vitro in human or animal liver microsomes was used to determine intrinsic clearance ($CL_{int}$) and hepatic clearance (CLh,b) of a compound. These parameters were useful for predicting in vivo human clearance, which defines the level of drug exposure in vivo (Obach et al, 1997, 1999).

The metabolic stability half-life assay panel evaluates the time-course and the rate of CYP-mediated (NADPH-dependent) metabolism in vitro in human, rat, mouse, dog and monkey microsomes. The time course spans a 45-minute incubation, and includes 0, 5, 10, 15, 30, and 45 minute time-points, at each of which the amount of test compound remaining in the mixture was measured.

Result Interpretation Guideline

The results of the metabolic stability half-life assay are expressed as a half-life ($T_{1/2}$, min). In general, these results should be used to evaluate only the extent of CYP-mediated, or NADPH-dependent, metabolism of the test compound. When the compound was significantly metabolized ($T_{1/2}$<14 minutes), this indicated high clearance in vivo due to CYP-mediated metabolism. However, if the compound demonstrated moderate (14-70 minutes) or low (>70 minutes) metabolism in these in vitro assays, high clearance was still possible in vivo via other metabolism and elimination pathways.

The results of these assays were predictive of compound clearance in vivo, assuming that CYP-mediated metabolism was a predominant elimination pathway. In human microsomes, the ranges of results were approximately as shown in the following table:

TABLE 19

Metabolic Stability Half-Life-Result Interpretation Guidelines

| CYP-Mediated Clearance | $T_{1/2}$, minutes Human |
|---|---|
| Low | >70 |
| Medium | 14-70 |
| High | <14 |

Methods and Materials

Liver microsomes were purchased from BD Biosciences (Woburn, Mass.) and NADPH from AppliChem Inc; all other reagents were obtained from Sigma.

Incubation with Liver Microsomes

Test compound was received as a 3.5 mM stock solution in 100 percent DMSO. The test compound was diluted to create a 50 μM acetonitrile (ACN) solution containing 1.4% DMSO, which was then used as a 100-fold stock for incubation with microsomes. Each compound was tested in human, rat, mouse, dog and monkey liver microsomes. Compound, NADPH and liver microsome solutions were combined for incubation in three steps:

1. 450 μl of liver microsome suspension, protein concentration of 1.1 mg/ml in 100 mM $NaP_i$, pH 7.4, 5 mM $MgCl_2$ buffer, was pre-warmed at 37° C.

2. 5 μl of 50 μM compound (98.6% ACN, 1.4% DMSO) was added to the same tube and pre-incubated at 37° C. for 5 minutes.

3. The reaction was initiated by the addition of 50 μl of pre-warmed 10 mM NADPH solution in 100 mM $NaP_i$, pH 7.4.

Reaction components were mixed well, and 65 μl were immediately transferred into 130 μl quench/stop solution (zero-time point, $T_0$). Reactions were incubated at 37° C. for 5, 10, 15, 30 and 45 minutes and at each time-point a 65 μl aliquot was transferred into 130 μl of quench solution. Acetonitrile containing Internal Standard (100 ng/ml), was used as the quench solution to terminate metabolic reactions.

Quenched mixtures were centrifuged at 1500 rpm (~500× g) in an ALLEGRA® X-12 centrifuge, SX4750 rotor (Beckman Coulter Inc., Fullerton, Calif.) for fifteen minutes to pellet denatured microsomes. A volume of 90 μl of supernatant extract, containing the mixture of parent compound and its metabolites, was then transferred to a separate 96-well plate for LC/MS-MS analysis to determine the percent of parent compound that was remaining in the mixture.

TABLE 20

Metabolic Stability Half-Life Assays - Reaction Components

| Reaction Components | Final Concentration in the Metabolic Stability Assay |
|---|---|
| Compound (Substrate) | 0.5 μM |
| NaPi Buffer, pH 7.4 | 100 mM |
| DMSO | 0.014% |
| Acetonitrile | 0.986% |
| Microsomes (human, rat, mouse) (BD/Gentest) | 1 mg/ml protein |
| NADPH | 1.0 mM |
| $MgCl_2$ | 5.0 mM |
| 37° C. Incubation time | 0, 5, 10, 15, 30, and 45 minutes |
| Quench/Stop Solution (ACN + 100 μM DMN) | 130 μl |
| Sample of Reaction | 65 μl |
| Sedimentation of Denatured Microsomes | 15 minutes |

Sample Analysis—Instrumentation

HPLC: Pump—Shimadzu LC-20 AD series binary pumps; Autosampler—CTC/LEAP HTS.

Table 21 below lists the CYP-mediated metabolic half life value for Examples 1-38 of this invention and Comparative Compounds 39-42 measured in the human metabolic stability half-life assay. In some instances, the value is an average of multiple experiments where N is the number of experiments conducted. The compounds of the present invention, as exemplified by Examples 1-38 had metabolic stability half life values of 31 minutes or longer. In contrast, Comparative Compounds 39-42 had metabolic stability half life values of 8 minutes or less.

TABLE 21

| Example | HLM $t_{1/2}$ (min) | N |
|---|---|---|
| 1 | 40 | 2 |
| 2 | 103 | 3 |
| 3 | 42 | 3 |
| 4 | 96 | 2 |
| 5 | 32 | 3 |
| 6 | 73 | 2 |

TABLE 21-continued

| Example | HLM $t_{1/2}$ (min) | N |
|---|---|---|
| 7 | 46 | 1 |
| 8 | >120 | 2 |
| 9 | >120 | 2 |
| 10 | 85 | 1 |
| 11 | 92 | 2 |
| 12 | 98 | 3 |
| 13 | 118 | 2 |
| 14 | >120 | 1 |
| 15 | 34 | 1 |
| 16 | 107 | 1 |
| 17 | 93 | 1 |
| 18 | 76 | 2 |
| 19 | >120 | 2 |
| 20 | >120 | 1 |
| 21 | 115 | 2 |
| 22 | >120 | 1 |
| 23 | 118 | 2 |
| 24 | 114 | 1 |
| 25 | 57 | 2 |
| 26 | 31 | 2 |
| 27 | >120 | 2 |
| 28 | 52 | 1 |
| 29 | 35 | 3 |
| 30 | >120 | 1 |
| 31 | 54 | 3 |
| 32 | >120 | 1 |
| 33 | 56 | 1 |
| 34 | 49 | 1 |
| 35 | >120 | 2 |
| 36 | >120 | 2 |
| 37 | 33 | 1 |
| 38 | 120 | 1 |
| Comparative Compound 39 | 8 | 1 |
| Comparative Compound 40 | 6 | 1 |
| Comparative Compound 41 | 6 | 1 |
| Comparative Compound 42 | 3 | 1 |

The exemplified compounds of the invention showed the surprising advantage of low clearance due to CYP-mediated metabolism in the human metabolic stability half life assay. The compounds of the present invention, as exemplified by Examples 1-38, had metabolic half lives of 31 minutes or longer in the human metabolic stability half life assay. In contrast, Comparative Compounds 39-42 had metabolic half lives of 8 minutes or less in the human metabolic stability assay. Comparative Compounds 39-42 showed high clearance in the human metabolic stability assay, indicating that the compounds were removed by liver microsomes.

The compounds of the present invention (Examples 1-38) have been compared to the Comparative Compounds 39-42 disclosed in U.S. Pat. No. 7,456,172, and have been found to be especially advantageous. The compounds of the present invention had the surprising advantage of the combination of activity as inhibitors of Notch 1 and Notch 3 and superior metabolic stability to liver microsomes. As shown in Tables 13 and 21, in the reported tests, Examples 1-38 of this invention had Notch 1 $IC_{50}$ values of 22.5 nM or less and Notch 3 $IC_{50}$ values of 46.2 nM or less; and human metabolic stability half lives of 31 minutes or longer in the human metabolic stability half life assay. In contrast, in similar tests, Comparative Compounds 39-42 had Notch 1 $IC_{50}$ values of in the range of from 5.1 nM to 64.1 nM and Notch 3 $IC_{50}$ values in the range of 12.5 nM to 74.5 nM; and human metabolic stability half lives of 8 minutes or less.

Human Tumor Xenograft Models in Mice

All rodents were obtained from Harlan Sprague Dawley Co. (Indianapolis, Ind.), and maintained in an ammonia-free environment in a defined and pathogen-free colony. All mice were quarantined approximately 1 week prior to their use for tumor propagation and drug efficacy testing. Mice were fed food and water ad libitum. The animal care program of Bristol-Myers Squibb Pharmaceutical Research Institute is fully accredited by the American Association for Accreditation of Laboratory Animal Care (AAALAC). All experiments were performed in accordance with Bristol-Myers Squibb (BMS) animal test methods and guidelines.

Tumor xenografts were grown and maintained subcutaneously (SC) in immunocompromized balb/c nu/nu nude or NOD-SCID mice (Harlan Sprague Dawley). Tumors were propagated as subcutaneous transplants in the appropriate mouse strain (Table 22) using tumor fragments obtained from donor mice.

TABLE 22

Histological Types and Host Mouse Strain/Gender Requirement for the Propagation of Various Human Tumor Xenografts in Mice

| Tumor Type | Histology | Mouse Strain | Sex |
|---|---|---|---|
| TALL-1 | ALL | NOD-SCID | female |
| HPB-ALL | ALL | NOD-SCID | female |
| ALL-SIL | ALL | NOD-SCID | female |
| MDA-MB-157 | breast | NOD-SCID | female |
| MDA-MB-468 | breast | NOD-SCID | female |
| PAT-34 | ovarian | nude | female |
| PAT-50 | ovarian | nude | female |
| PAT-26 | pancreas | nude | female |
| PAT-27 | pancreas | nude | female |

Preclinical Chemotherapy Trials

The required numbers of animals needed to detect a meaningful response were pooled at the start of the experiment and each was given a subcutaneous implant of a tumor fragment (~20 mg) with a 13-gauge trocar. Tumors were allowed to grow to the pre-determined size window (tumors outside the range were excluded) and animals were evenly distributed to various treatment and control groups. There were typically 8 mice per treatment and control groups, with the exception of experiments conducted in the SAL-IGF (this is not included in Table 22) tumor model, in which there were typically 5 mice per treatment and control group. Treatment of each animal was based on individual body weight. Treated animals were checked daily for treatment related toxicity/mortality. Each group of animals was weighed before the initiation of treatment ($Wt_1$) and then again following the last treatment dose ($Wt_2$). The difference in body weight ($Wt_2-Wt_1$) provides a measure of treatment-related toxicity.

Tumor response was determined by measurement of tumors with a caliper twice a week, until the tumors reached a predetermined "target" size of 0.5 gm or 1 gm depending on the tumor type. Tumor weights (mg) were estimated from the formula:

$$\text{Tumor weight} = (\text{length} \times \text{width}^2) \div 2$$

Tumor response criteria are expressed in terms of tumor growth inhibition (% TGI). Tumor growth delay is defined as the difference in time (days) required for the treated tumors (T) to reach a predetermined target size compared to those of the control group (C). For this purpose, the tumor weight of a group is expressed as medium tumor weight (MTW).

Tumor growth inhibition is calculated as follows:

$$\% \text{ Tumor Growth Inhibition} = \frac{\left(1 - \frac{T_t}{T_0} * \frac{C_0}{C_t}\right)}{\left(1 - \frac{C_0}{C_t}\right)}$$

where, $C_t$=Median control tumor size at end of treatment $C_0$=Median control tumor size at treatment initiation $T_t$=Median tumor size of treated group at end of treatment $T_0$=Median tumor size of treated group at treatment initiation Activity is defined as the achievement of durable tumor growth inhibition of 50% or greater (i.e., TGI≥50%) or log cell kill of 0.5 or greater (LCK≥0.5) for a period equivalent to at least 1 tumor volume doubling time and drug treatment must be for a period equivalent to at least 2 tumor volume doubling time.

Tumor response was also expressed in terms of tumor growth delay (TGD value), defined as the difference in time (days) required for the treated tumors (T) to reach a predetermined target size compared to those of the control group (C).

Whenever possible, antitumor activity was determined at a range of dose levels up to the maximum tolerated dose (MTD) which is defined as the dose level immediately below which excessive toxicity (i.e., more than one death) occurred. When death occurred, the day of death was recorded. Treated mice dying prior to having their tumors reach target size were considered to have died from drug toxicity. No control mice died bearing tumors less than target size. Treatment groups with more than one death caused by drug toxicity were considered to have had excessively toxic treatments and their data were not included in the evaluation of a compound's antitumor efficacy.

Potential drug toxicity interaction affecting treatment tolerability is an important consideration in combination chemotherapy trials. Interpretation of combination therapeutic results must be based on comparison of antitumor activity of the best possible response for the single agents versus the combination at comparably tolerated doses. Therefore, therapeutic synergism was defined as a therapeutic effect achieved with a tolerated regimen of the combined agents that exceeded the optimal effect achieved at any tolerated dose of monotherapy. Statistical evaluations of data were performed using Gehan's generalized Wilcoxon test. Statistical significance was declared at P<0.05.

Drug Administration

In in vitro studies, all agents were dissolved in 100% DMSO and serially diluted in media/10% fetal bovine serum. The following excipients were used for administration of the Notch inhibitors to rodents: ETOH/TPGS/PEG300 (10:10:80). Notch inhibitors were typically administered orally on a schedule of QD×15, 10 day-on-2 day-off-5 day-on, although other schedules had also been evaluated and shown to be efficacious. For example, dosing regimen consisting of QD×12, 4 day-on-3 day-off was shown to be equally efficacious as QD×15, 10 day-on-2 day-off-5 day-on. In the BID studies, the second dose was given 6 to 12 hours after the first dose.

What is claimed is:

1. A compound of Formula (I):

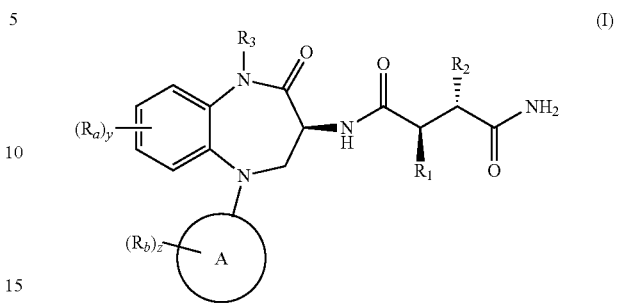

wherein:

$R_1$ is —$CH_2CH_2CF_3$;

$R_2$ is —$CH_2CH_2CF_3$, —$CH_2$(cyclopropyl), or phenyl;

$R_3$ is H or —$CH_3$;

Ring A is phenyl or pyridinyl;

each $R_a$ is independently F, Cl, —CN, —$CHF_2$, or cyclopropyl;

each $R_b$ is independently F, Cl, —CN, —$CH_3$, —$CHF_2$, —$CF_3$, or cyclopropyl;

y is zero, 1, or 2; and z is zero, 1, or 2.

2. The compound according to claim 1 wherein $R_3$ is H.

3. The compound according to claim 1 wherein $R_3$ is —$CH_2CH_2CF_3$.

4. The compound according to claim 1 wherein $R_2$ is —$CH_2$(cyclopropyl).

5. The compound according to claim 4 wherein $R_2$ is phenyl.

6. The compound according to claim 1 wherein Ring A is phenyl.

7. The compound according to claim 1 wherein Ring A is pyridinyl.

8. A compound according to claim 1 selected from: (2R,3S)—N-((3S)-6-chloro-1-(3-cyclopropylphenyl)-4-oxo-2,3,4,5-tetrahydro-1H-1,5-benzodiazepin-3-yl)-2,3-bis(3,3,3-trifluoropropyl)succinamide (1); (2R,3R)—N-((3S)-1-(3-cyanophenyl)-6-(difluoromethyl)-4-oxo-2,3,4,5-tetrahydro-1H-1,5-benzodiazepin-3-yl)-3-phenyl-2-(3,3,3-trifluoropropyl)succinamide(2); (2R,3S)—N-((3S)-1-(3-chlorophenyl)-4-oxo-2,3,4,5-tetrahydro-1H-1,5-benzodiazepin-3-yl)-2,3-bis(3,3,3-trifluoropropyl)succinamide (3); (2R,3S)—N-((3S)-1-(4-chlorophenyl)-4-oxo-2,3,4,5-tetrahydro-1H-1,5-benzodiazepin-3-yl)-2,3-bis(3,3,3-trifluoropropyl)succinamide (4); (2R,3S)—N-((3S)-1-(3-cyclopropylphenyl)-4-oxo-2,3,4,5-tetrahydro-1H-1,5-benzodiazepin-3-yl)-2,3-bis(3,3,3-trifluoropropyl)succinamide (5); (2R,3S)—N-((3S)-1-(4-fluorophenyl)-4-oxo-2,3,4,5-tetrahydro-1H-1,5-benzodiazepin-3-yl)-2,3-bis(3,3,3-trifluoropropyl)succinamide (6); (2R,3S)—N-((3S)-1-(3-chlorophenyl)-6-cyclopropyl-4-oxo-2,3,4,5-tetrahydro-1H-1,5-benzodiazepin-3-yl)-2,3-bis(3,3,3-trifluoropropyl)succinamide (7); (2R,3R)—N-((3S)-6-cyano-4-oxo-1-(3-(trifluoromethyl)phenyl)-2,3,4,5-tetrahydro-1H-1,5-benzodiazepin-3-yl)-3-phenyl-2-(3,3,3-trifluoropropyl)succinamide (8); (2R,3R)—N-((3S)-1-(3-chloro-5-cyanophenyl)-6-(difluoromethyl)-4-oxo-2,3,4,5-tetrahydro-1H-1,5-benzodiazepin-3-yl)-3-phenyl-2-(3,3,3-trifluoropropyl)succinamide (9); (2R,3S)—N-((3S)-1-(3-cyanophenyl)-6-(difluoromethyl)-4-oxo-2,3,4,5-tetrahydro-1H-1,5-benzodiazepin-3-yl)-2,3-bis(3,3,3-trifluoropropyl)

succinamide (10); (2R,3R)—N-((3S)-1-(3-cyano-5-methylphenyl)-6-(difluoromethyl)-4-oxo-2,3,4,5-tetrahydro-1H-1,5-benzodiazepin-3-yl)-3-phenyl-2-(3,3,3-trifluoropropyl)succinamide (11); (2R,3S)—N-((3S)-6-(difluoromethyl)-1-(3-(difluoromethyl)phenyl)-4-oxo-2,3,4,5-tetrahydro-1H-1,5-benzodiazepin-3-yl)-2,3-bis(3,3,3-trifluoropropyl) succinamide (12); (2R,3R)—N-(1-(3-cyano-5-fluorophenyl)-6-(difluoromethyl)-4-oxo-2,3,4,5-tetrahydro-1H-1,5-benzodiazepin-3-yl)-3-phenyl-2-(3,3,3-trifluoropropyl)succinamide (13); (2R,3S)-3-(cyclopropylmethyl)-N-((3S)-6-fluoro-4-oxo-1-(3-(trifluoromethyl)phenyl)-2,3,4,5-tetrahydro-1H-1,5-benzodiazepin-3-yl)-2-(3,3,3-trifluoropropyl)succinamide (14); (2R,3S)-3-(cyclopropylmethyl)-N-((3S)-1-(3-cyclopropylphenyl)-6-fluoro-4-oxo-2,3,4,5-tetrahydro-1H-1,5-benzodiazepin-3-yl)-2-(3,3,3-trifluoropropyl)succinamide (15); (2R,3S)-3-(cyclopropylmethyl)-N-((3S)-1-(3,4-dichlorophenyl)-6-fluoro-4-oxo-2,3,4,5-tetrahydro-1H-1,5-benzodiazepin-3-yl)-2-(3,3,3-trifluoropropyl)succinamide (16); (2R,3S)—N-((3S)-1-(3-cyanophenyl)-6-fluoro-4-oxo-2,3,4,5-tetrahydro-1H-1,5-benzodiazepin-3-yl)-2,3-bis(3,3,3-trifluoropropyl)succinamide (17); (2R,3R)—N-((3S)-1-(3-cyanophenyl)-6-fluoro-4-oxo-2,3,4,5-tetrahydro-1H-1,5-benzodiazepin-3-yl)-3-phenyl-2-(3,3,3-trifluoropropyl)succinamide (18); (2R,3S)—N-((3S)-6-chloro-1-(4-chlorophenyl)-4-oxo-2,3,4,5-tetrahydro-1H-1,5-benzodiazepin-3-yl)-3-(cyclopropylmethyl)-2-(3,3,3-trifluoropropyl) succinamide (19); (2R,3S)—N-((3S)-6-chloro-4-oxo-1-(3-(trifluoromethyl)phenyl)-2,3,4,5-tetrahydro-1H-1,5-benzodiazepin-3-yl)-2,3-bis(3,3,3-trifluoropropyl)succinamide (20); (2R,3S)—N-((3S)-6-chloro-4-oxo-1-(3-(trifluoromethyl)phenyl)-2,3,4,5-tetrahydro-1H-1,5-benzodiazepin-3-yl)-3-(cyclopropylmethyl)-2-(3,3,3-trifluoropropyl)succinamide (21); (2R,3R)—N-((3S)-6-chloro-4-oxo-1-(3-(trifluoromethyl)phenyl)-2,3,4,5-tetrahydro-1H-1,5-benzodiazepin-3-yl)-3-phenyl-2-(3,3,3-trifluoropropyl)succinamide (22); (2R,3S)—N-((3S)-6-chloro-1-(3-cyanophenyl)-4-oxo-2,3,4,5-tetrahydro-1H-1,5-benzodiazepin-3-yl)-2,3-bis(3,3,3-trifluoropropyl)succinamide (23); (2R,3R)—N-((3S)-6-chloro-1-(3-cyanophenyl)-4-oxo-2,3,4,5-tetrahydro-1H-1,5-benzodiazepin-3-yl)-3-phenyl-2-(3,3,3-trifluoropropyl)succinamide (24); (2R,3S)—N-((3S)-6-chloro-1-(3-cyanophenyl)-4-oxo-2,3,4,5-tetrahydro-1H-1,5-benzodiazepin-3-yl)-3-(cyclopropylmethyl)-2-(3,3,3-trifluoropropyl) succinamide (25); (2R,3S)—N-((3S)-6-chloro-1-(2-cyanophenyl)-4-oxo-2,3,4,5-tetrahydro-1H-1,5-benzodiazepin-3-yl)-3-(cyclopropylmethyl)-2-(3,3,3-trifluoropropyl)succinamide (26); (2R,3R)—N-((3S)-6-chloro-1-(3-cyano-5-fluorophenyl)-4-oxo-2,3,4,5-tetrahydro-1H-1,5-benzodiazepin-3-yl)-3-phenyl-2-(3,3,3-trifluoropropyl)succinamide (27); (2R,3S)—N-((3S)-6-chloro-1-(3-cyano-5-fluorophenyl)-4-oxo-2,3,4,5-tetrahydro-1H-1,5-benzodiazepin-3-yl)-3-(cyclopropylmethyl)-2-(3,3,3-trifluoropropyl)succinamide (28); (2R,3S)—N-((3S)-6-chloro-1-(3-cyclopropylphenyl)-4-oxo-2,3,4,5-tetrahydro-1H-1,5-benzodiazepin-3-yl)-3-(cyclopropylmethyl)-2-(3,3,3-trifluoropropyl)succinamide (29); (2R,3R)—N-((3S)-6-chloro-1-(3,4-dichlorophenyl)-4-oxo-2,3,4,5-tetrahydro-1H-1,5-benzodiazepin-3-yl)-3-phenyl-2-(3,3,3-trifluoropropyl)succinamide (30); (2R,3S)—N-((3S)-6-chloro-1-(3-chlorophenyl)-4-oxo-2,3,4,5-tetrahydro-1H-1,5-benzodiazepin-3-yl)-2,3-bis(3,3,3-trifluoropropyl)succinamide (31); (2R,3S)—N-((3S)-6-chloro-1-(3,4-dichlorophenyl)-4-oxo-2,3,4,5-tetrahydro-1H-1,5-benzodiazepin-3-yl)-2,3-bis(3,3,3-trifluoropropyl) succinamide (32); (2R,3S)—N-((3S)-6-chloro-4-oxo-1-(2-pyridinyl)-2,3,4,5-tetrahydro-1H-1,5-benzodiazepin-3-yl)-2,3-bis(3,3,3-trifluoropropyl)succinamide (33); (2R,3R)—N-((3S)-6-chloro-4-oxo-1-(6-(trifluoromethyl)-2-pyridinyl)-2,3,4,5-tetrahydro-1H-1,5-benzodiazepin-3-yl)-3-phenyl-2-(3,3,3-trifluoropropyl) succinamide (34); (2R,3S)—N-((3S)-6-chloro-4-oxo-1-(6-(trifluoromethyl)-2-pyridinyl)-2,3,4,5-tetrahydro-1H-1,5-benzodiazepin-3-yl)-2,3-bis(3,3,3-trifluoropropyl)succinamide (35); (2R,3R)—N-((3S)-6-chloro-4-oxo-1-(4-(trifluoromethyl)-2-pyridinyl)-2,3,4,5-tetrahydro-1H-1,5-benzodiazepin-3-yl)-3-phenyl-2-(3,3,3-trifluoropropyl)succinamide (36); (2R,3S)—N-((3S)-7-fluoro-4-oxo-1-phenyl-2,3,4,5-tetrahydro-1H-1,5-benzodiazepin-3-yl)-2,3-bis(3,3,3-trifluoropropyl) succinamide (37); and (2R,3S)—N-((3S)-7-fluoro-4-oxo-1-(3-(trifluoromethyl)phenyl)-2,3,4,5-tetrahydro-1H-1,5-benzodiazepin-3-yl)-2,3-bis(3,3,3-trifluoropropyl) succinamide (38).

9. A pharmaceutical composition comprising a compound according to claim 1; and a pharmaceutically acceptable carrier.

* * * * *